United States Patent
Copeland et al.

(10) Patent No.: US 11,602,555 B2
(45) Date of Patent: Mar. 14, 2023

(54) TREATMENT OF RESPIRATORY TRACT DISEASES AND INFECTIONS WITH ASCORBIC ACID COMPOSITIONS

(71) Applicant: RENOVION, INC., Durham, NC (US)

(72) Inventors: Dan Copeland, Chapel Hill, NC (US); Carolyn Durham, Chapel Hill, NC (US); Thomas E. Richardson, Chapel Hill, NC (US)

(73) Assignee: RENOVION, INC., Chapel Hill, NC (US)

( * ) Notice: Subject to any disclaimer, the term of this patent is extended or adjusted under 35 U.S.C. 154(b) by 0 days.

(21) Appl. No.: 16/461,671

(22) PCT Filed: Nov. 17, 2017

(86) PCT No.: PCT/US2017/062412
§ 371 (c)(1),
(2) Date: May 16, 2019

(87) PCT Pub. No.: WO2018/094278
PCT Pub. Date: May 24, 2018

(65) Prior Publication Data
US 2019/0351005 A1    Nov. 21, 2019

Related U.S. Application Data

(60) Provisional application No. 62/423,721, filed on Nov. 17, 2016, provisional application No. 62/423,702, filed on Nov. 17, 2016.

(51) Int. Cl.
| | |
|---|---|
| *A61K 38/06* | (2006.01) |
| *A61P 31/04* | (2006.01) |
| *A61P 11/00* | (2006.01) |
| *A01N 37/30* | (2006.01) |
| *A61K 9/00* | (2006.01) |
| *A61K 9/19* | (2006.01) |
| *A61K 45/06* | (2006.01) |
| *A61K 47/02* | (2006.01) |
| *A61K 47/22* | (2006.01) |

(52) U.S. Cl.
CPC ............ *A61K 38/063* (2013.01); *A01N 37/30* (2013.01); *A61K 9/0073* (2013.01); *A61K 9/19* (2013.01); *A61K 45/06* (2013.01); *A61K 47/02* (2013.01); *A61K 47/22* (2013.01); *A61P 11/00* (2018.01); *A61P 31/04* (2018.01)

(58) Field of Classification Search
None
See application file for complete search history.

(56) References Cited

U.S. PATENT DOCUMENTS

| | | |
|---|---|---|
| 2,606,903 A | 8/1952 | Ruskin |
| 4,861,783 A | 8/1989 | Ackernian et al. |
| 4,968,716 A | 11/1990 | Markhani |
| 5,070,085 A | 12/1991 | Markhani |
| 5,238,683 A | 8/1993 | Crystal |
| 5,304,724 A | 4/1994 | Newton et al. |
| 5,626,883 A | 5/1997 | Paul |
| 5,824,693 A | 10/1998 | Goldberg |
| 5,989,521 A | 11/1999 | Crystal |
| 6,228,347 B1 | 5/2001 | Hersh et al. |
| 6,312,734 B1 | 11/2001 | Kozhemyakin et al. |
| 6,423,687 B1 | 7/2002 | Demopoulos |
| 6,723,703 B2 | 4/2004 | Gaston et al. |
| 9,308,234 B2 | 4/2016 | Arnold et al. |
| 10,406,200 B2 | 9/2019 | Arnold et al. |
| 2004/0229815 A1 | 11/2004 | Nagasawa et al. |
| 2006/0018945 A1 | 1/2006 | Britigan et al. |
| 2006/0204557 A1 | 9/2006 | Gupta et al. |
| 2006/0228693 A1 | 10/2006 | Soll |
| 2006/0258599 A1 | 11/2006 | Childers |
| 2007/0049641 A1 | 3/2007 | Tirouvanziam et al. |
| 2009/0214674 A1* | 8/2009 | Barraud ............... A61K 31/197 424/718 |
| 2009/0270310 A1 | 10/2009 | Whyte |
| 2010/0311837 A1 | 12/2010 | Sakai et al. |
| 2012/0021071 A1 | 1/2012 | Bordeau et al. |
| 2012/0093947 A1 | 4/2012 | Britigan et al. |
| 2013/0084336 A1 | 4/2013 | Friedman et al. |
| 2013/0129815 A1 | 5/2013 | Guilford et al. |
| 2015/0010654 A1* | 1/2015 | Arnold ................. A61K 31/375 424/717 |
| 2015/0374626 A1 | 12/2015 | Guilford |

(Continued)

FOREIGN PATENT DOCUMENTS

| | | |
|---|---|---|
| AU | 2004315267 A1 | 8/2005 |
| AU | 2004315267 B2 | 1/2009 |

(Continued)

OTHER PUBLICATIONS

Zhang et al. (Sci China C Life Sci. Jun. 2009;52(6):501-5) (Year: 2009).*
Visscher et al. (Proc Am Thorac Soc vol. 3. pp. 41-47, 2006) (Year: 2006).*
Shields et al. (J Heart Lung Transplant. Nov. 2012;31(11):1199-206, abstract only) (Year: 2012).*
Hayes et al., Semin Respir Crit Care Med. Apr. 2010;31(2):123-38 (Year: 2010).*

(Continued)

*Primary Examiner* — Sergio Coffa

(74) *Attorney, Agent, or Firm* — Sterne, Kessler, Goldstein & Fox P.L.L.C.

(57) ABSTRACT

The application is directed to a method of inhibiting or reducing growth of clinical isolate bacteria comprising contacting the clinical isolate with a composition comprising glutathione, a glutathione derivative, a glutathione conjugate, a pharmaceutically-acceptable salt thereof, or any combination thereof.

11 Claims, No Drawings

(56) References Cited

U.S. PATENT DOCUMENTS

| | | |
|---|---|---|
| 2016/0367620 A1 | 12/2016 | Demopoulos |
| 2016/0367621 A1 | 12/2016 | Demopoulos et al. |

FOREIGN PATENT DOCUMENTS

| | | |
|---|---|---|
| AU | 2005305456 B2 | 5/2011 |
| CA | 2058793 A1 | 7/1992 |
| CA | 2339473 A1 | 2/2000 |
| CA | 2620123 A1 | 3/2007 |
| CA | 2620123 C | 11/2011 |
| CN | 1921876 A | 2/2007 |
| CN | 101175499 B | 12/2010 |
| CN | 101987195 A | 3/2011 |
| CN | 102100904 B | 4/2013 |
| CN | 102329370 B | 7/2015 |
| DE | 2845484 A1 | 4/1980 |
| DE | 19935763 A1 | 2/2001 |
| DE | 102004035113 A1 | 2/2006 |
| EP | 0938331 B1 | 12/2002 |
| EP | 1282416 A2 | 2/2003 |
| EP | 1701732 A2 | 9/2006 |
| EP | 1474158 B1 | 10/2009 |
| EP | 1333823 B1 | 3/2010 |
| JP | 2004514650 A | 5/2004 |
| JP | 4652664 B2 | 3/2011 |
| WO | WO-9819694 A1 | 5/1998 |
| WO | WO-0189520 A2 | 11/2001 |
| WO | WO-01089520 A3 | 11/2001 |
| WO | WO-0232418 A1 | 4/2002 |
| WO | WO-2005074903 A2 | 8/2005 |
| WO | WO-2005074903 A3 | 8/2005 |
| WO | WO-2005120457 A1 | 12/2005 |
| WO | WO-2006054304 A2 | 5/2006 |
| WO | WO-2006060120 A2 | 6/2006 |
| WO | WO-2006060120 A3 | 6/2006 |
| WO | WO-2007024876 A2 | 3/2007 |
| WO | WO-2007024876 A3 | 3/2007 |
| WO | WO-2007134180 A2 | 11/2007 |
| WO | WO-2009001884 A1 | 12/2008 |
| WO | WO-2010033292 A2 | 3/2010 |
| WO | WO-2010086530 A1 | 8/2010 |
| WO | WO-2012017367 A1 | 2/2012 |
| WO | WO-2012027603 A2 | 3/2012 |
| WO | WO-2012085582 A1 | 6/2012 |
| WO | WO-2014070769 A1 | 5/2014 |
| WO | WO-2014127245 A1 | 8/2014 |
| WO | WO-2019099946 A1 | 5/2019 |

OTHER PUBLICATIONS

Avgeri, S.G., et al., "Therapeutic Options for Burkholderia Cepacia Infections Beyond Co-trimoxazole: a Systematic Review of the Clinical Evidence," International Journal of Antimicrobial Agents 33(5):394-404, Elsevier Science Publishers, Netherlands (May 2009).

Bishop, C., et la., "A Pilot Study of the Effect of Inhaled Buffered Reduced Glutathione on the Clinical Status of Patients with Cystic Fibrosis," Chest Journal 127 (1):308-317, Elsevier, Netherlands (2005).

Bjarnsholt,T., et al., "The role of bacterial biofilms in chronic infections," 136:1-51, APMIS Suppl., Blackwell Publishing Ltd., United States (2013).

Bois., et al., "Fundamentals of Otolaryngology," W. B. Saunders Co., Philadelphia, 1989, pp. 184.

Boyanova, et al., "Coadministration of probiotics with antibiotics: why, when and for how long?," Expert Rev Anti Infect Ther 10(4):407-409, Taylor & Francis, United States (2014).

Bray, T.M., and Taylor, C.G., "Tissue Glutathione, Nutrition, and Oxidative Stress," Canadian Journal of Physiology and Pharmacology 71(9):746-751, Canadian Science Publishing, Canada (Sep. 1993).

Cursino, L., et al., "Synergic interaction between ascorbic acid and antibiotics against Pseudomonas aemginosa," Brazilian Archives of Biology and Technology 48(3): 379-384,Brazilian Archives of Biology and Technology, Brazil (2005).

Donnely, L.E., et al., "Defective Phagocytosis in airways and disease," Chest 141(4):1055-1062, Elsevier, Netherlands (2012).

Fitzpatrick, A.M., et al., "Glutathione oxidation is associated with airway macrophage functional impairment in children with severe asthma," Pedatric Res 69(2):154-159, International Pediatric Research Foundation Inc., United States (2011).

International Search Report for Application No. PCT/US2017/062412, dated Jan. 30, 2018, 3 pages.

Klockgether, J., et al., "Genome Diversity of Pseudomonas Aeruginosa Pao1 Laboratory Strains," Journal of Bacteriology, 192(4):1113-1121, American Society for Microbiology, United States (Feb. 2010).

Sanchez, C. et al., "Inter-Subject Variability in Human Atrial Action Potential in Sinus Rhythm versus Chronic Atrial Fibrillation," PLOS One 9(8):e105897, Public Library of Science, United States (2014).

Sass, A.M., et al., "The Unexpected Discovery of a Novel Low-oxygen-activated Locus for the Anoxic Persistence of Burkholderia Cenocepacia," The ISME Journal 7(8):1568-1581, Nature Publishing Group, England (Aug. 2013).

Schwab, U., et al., "Localization of Burkholderia Cepacia Complex Bacteria in Cystic Fibrosis Lungs and Interactions With Pseudomonas Aemginosa in Hypoxic Mucus," Infection and immunity 82(11):4729-4745, American Society for Microbiology, United States (Nov. 2014).

Shields, R.K., et al., "*Staphylococcus aureus* Infections in the Early Period After Lung Transplantation: Epidemiology, Risk Factors, and Outcomes," The Journal of Heart and Lung Transplantation 31(11):1199-1206, Elsevier, United States (Nov. 2012).

Simpson, G.L. and Ortwerth, B.J., "The Non-Oxidative Degradation of Ascorbic Acid at Physiological Conditions", Biochimica et Biophysica Acta, 1501(1):12-24, Elsevier Pub. Co, Netherlands (Apr. 2000).

Taglietti, A., et al., "Antibacterial Activity of Glutathione-Coated Silver Nanoparticles against Gram Positive and Gram Negative Bacteria," Langmuir, 28(21):8140-8148, American Chemical Society, United States (May 2012).

Tong, S.Y., et al., "*Staphylococcus aureus* Infections: Epidemiology, Pathophysiology, Clinical Manifestations, and Management," Clinical Microbiology Reviews 28(3):603-661, American Society for Microbiology, United States (Jul. 2015).

Varga, J.J., et al., "Genotypic and Phenotypic Analyses of a Pseudomonas Aeruginosa Chronic Bronchiectasis Isolate Reveal Differences From Cystic Fibrosis and Laboratory Strains," BMC Genomics 16:883, BioMed Central, England (Oct. 2015).

Visca, A., et al., "Improvement in clinical markers in CF patients using a reduced glutathione regimen: An uncontrolled, observational study," Journal of Cystic Fibrosis 7:433-436, Elsevier, Netherlands (2008).

Wagner, T., et al., "Effects of Azithromycin on Clinical Isolates of Pseudomonas Aeruginosa From Cystic Fibrosis Patients," Chest 128(2):912-919, Elsevier, United States (Aug. 2005).

Zhang, Y and Duan, K., "Glutathione Exhibits Antibacterial Activity and Increases Tetracycline Efficacy against Pseudomonas Aeruginosa," Science China Life Sciences, 52(6):501-505, Science in China Press, co published with Springer-Verlag, China (Jun. 2009).

Zhao, J., et al., "Decade-long Bacterial Community Dynamics in Cystic Fibrosis Airways," Proceedings of the National Academy of Sciences of the United States of America 109(15):5809-5814, National Academy of Sciences, United States (Apr. 2012).

Atkuri et al. "N-Acetylcysteine-a safe antidote for cysteine/glutathione deficiency" Current Opinion in Pharmacology 7(4):355-359 (2007).

Bergamini et al. "Azithromycin Decreases Glutathione-Stransferase T1 (GSTT1) and M1 (GSTM1) Expression and Activity in Cystic Fibrosis Airway Epithelial Cells" Pediatric Pulmonology 42(Suppl. 30):297 Abstract 269 (2007) (1 page).

Bergamini et al. "Effects of Azithromycin on Glutathione S-Transferases in Cystic Fibrosis Airway Cells" American Journal of Respiratory Cell and Molecular Biology 41(2):199-206 (2009).

(56) References Cited

OTHER PUBLICATIONS

Brechbuhl et al. "Glutathione transport is a unique function of the ATP-binding cassette protein ABCG2" Journal of Biological Chemistry 285(22):16582-16587 (2010).
Cantin, AM "Potential for antioxidant therapy of cystic fibrosis" Current Opinion in Pulmonary Medicine 10(6):531-536 (2004).
Caraher et al. "The effect of recombinant human lactoferrin on growth and the antibiotic susceptibility of the cystic fibrosis pathogen Burkholderia cepacia complex when cultured planktonically or as biofilms" Journal of Antimicrobial Chemotherapy 60:546-554 (2007).
Carter, Chris J. "Pathogen and autoantigen homologous regions within the cystic fibrosis transmembrane conductance regulator (CFTR) protein suggest an autoimmune treatable component of cystic fibrosis" FEMS Immunology and Medical Microbiology 62(2):197-214 (2011).
Cheluvappa et al. "Reactions of Pseudomonas aeruginosa pyocyanin with reduced glutathione" Acta Biochimica Polonica 55(3):571-580 (2008).
Cheng et al. "The PDZ domain protein CAL interacts with mGluR5a and modulates receptor expression" Journal of Neurochemistry 112(3):588-598 (2010).
Childers et al. "A new model of cystic fibrosis pathology: Lack of transport of glutathione and its thiocyanate conjugates" Medical Hypotheses 68(1):101-112 (2007).
Ciofu et al. "Respiratory bacterial infections in cystic fibrosis" Current Opinion in Pulmonary Medicine 19:251-258 (2013).
Clunes et al. "Cystic fibrosis: the mechanisms of pathogenesis of an inherited lung disorder" Drug Discovery Today 4(2):63-72 (2007).
Colombo (Curr Opin Pulm Med 9:504-508, 2003) (Year: 2003).
Conner et al. "The lactoperoxidase system links anion transport to host defense in cystic fibrosis" Federation of European Biochemical Societies Letters 581:271-278 (2007).
Dauletbaev et al. "A Phase II Study on Safety and Efficacy of High-Dose N-Acetylcysteine in Patients with Cystic Fibrosis" European Journal of Medical Research 14(8):352-358 (2009).
Day et al. "Role for Cystic Fibrosis Transmembrane Conductance Regulator Protein in a Glutathione Response to Bronchopulmonary Pseudomonas Infection" Infection and Immunity 72(4):2045-2051 (2004).
Day, Brian J. "Glutathione-A Radical Treatment for Cystic Fibrosis Lung Disease?" Chest 127(1):12-14 (2005).
Donnelly et al. "Defective Phagocytosis in Airways Disease" Chest 141(4):1055-1062 (2012).
D'Orazio et al. "Extracellular Glutathione Decreases the Ability of Burkholderia cenocepacia to Penetrate into Epithelial Cells and to Induce an Inflammatory Response" PLOS One 7(10):e47550 (2012).
Elsheikh et al. "Enhanced antigenicity leads to altered immunogenicity in sulfamethoxazole-hypersensitive patients with cystic fibrosis" Journal of Allergy and Clinical Immunology 127(6):1543-U348 (2011).
England et al. (Clin Otolaryngol Allied Sci. Feb. 1999;24(1):67-8).
Feuillet-Fieux et al. "Glutathione S-transferases Related to P. aeruginosa Lung Infection in Cystic Fibrosis Children: Preliminary Study" Clinical Biochemistry 42(1-2):57-63 (2009).
Fischer "Mechanisms and Function of DUOX in Epithelia of the Lung" Antioxidants & Redox Signaling 11(0):2453-2465 (2009).
Fisher et al. (Anesth Analg. Sep.-Oct. 1966;45(5):531-4) (Year: 1966).
Flamant et al. "Glutathione-S-transferase M1 M3, P1 and T1 polymorphisms and severity of lung disease in children with cystic fibrosis" Pharmacogenetics 14(5):295-301 (2004).
Gao et al. "Abnormal glutathione transport in cystic fibrosis airway epithelia" American Journal of Phy siology-Lung Cellular and Molecular Physiology 21:L113-L118 (1999).
Gao et al. "Synthetic chloride channel restores glutathione secretion in cystic fibrosis airway epithelia" American Journal of Physiology-Lung Cellular and Molecular Physiology 281(1):L24-L30 (2001).
Geller "Aerosol Antibiotics in Cystic Fibrosis" Respiratory Care 54(5):658-670 (2009).
Gerson et al. "The Lactoperoxidase System Functions in Bacterial Clearance of Airways" Am J. Respir. Cell Mol. Biol. 22:665-671 (2000).
Gould et al. "Targeting maladaptive glutathione responses in lung disease" Biochemical Pharmacology 81(2):187-193 (2011).
Govindaraju et al. "Analysis of Glutathione in Rat Airway Surface Liquid by Capillary Zone Electrophoresis with Conductivity Detection" Journal of Chromatography B-Analytical Technologies in the Biomedical and Life Sciences 788(2):369-376 (2003).
Griese et al. "Improvement of alveolar glutathione and lung function but not oxidative state in cystic fibrosis" American Journal of Respiratory and Critical Care Medicine 169(7):822-828 (2004).
Griese et al. "Inhalation Treatment with Glutathione in Patients with Cystic Fibrosis" American Journal of Respiratory and Critical Care Medicine 188:83-89 (2013).
Grigoras et al. "Functional Characterization of the Saccharomyces cerevisiae ABC-transporter Yor1p Overexpressed in Plasma Membranes" Biochimica Biophysica Acta-Biomembranes 1778(1):68-78 (2008).
Gukasyan et al. "Glutathione and its transporters in ocular surface defense" The Ocular Surface 5(4):269-279 (2007).
Hartl et al. "Inhaled glutathione decreases PGE(2) and increases lymphocytes in cystic fibrosis lungs" Free Radical Biology and Medicine 39(4):463-472 (2005).
Wood et al. "Biomarkers of lipid peroxidation, airway inflammation and asthma" European Respiratory Journal 21(1):177-186 (2003).
Hector et al. "Glutathione in Airway Neutrophils in Cystic Fibrosis" Pediatric Pulmonology 44(Suppl. 32) Abstract 420:359-360 (2009).
Hector et al. "Novel Method to Process Cystic Fibrosis Sputum for Determination of Oxidative State" Respiration 80(5):393-400 (2010).
Henrion-Caude et al. "Liver disease in pediatric patients with cystic fibrosis is associated with glutathione S-transferase P1 polymorphism" Hepatology 36(4):913-917 (2002).
Howell et al. "ATP hydrolysis by a CFTR domain: Pharmacology and effects of G551D mutation" Biochemical and Biophysical Research Communications 271(2):518-525 (2000).
Huang et al. "Airway Microbiota and Bronchial Hyperresponsiveness in Patients with Sub-optimally Controlled Asthma" Journal of Allergy and Clinical Immunology 127(2):372-381 (2011).
Hudson, Valerie "Differing Compartments of Intracellular Glutathione Have Differing Levels of Glutathione in Cystic Fibrosis" Medical Hypotheses 68(4):919-920 (2007).
Hudson, Valerie "Rethinking cystic fibrosis pathology: The critical role of abnormal reduced glutathione (GSH) transport caused by CFTR mutation" Free Radical Biology and Medicine 30(12):1440-1461 (2001).
Inci et al. "Prevention of primary graft dysfunction in lung transplantation by N-acetylcysteine after prolonged cold ischemia" Journal of Heart and Lung Transplantation 29(11):1293-1301 (2010).
Innis et al. "Choline-related supplements improve altered abnormal plasma methionine-homocysteine and glutathione status in children with cystic fibrosis" American Journal of Clinical Nutrition 85(3):702-708 (2007).
Lehr "Global Markets for Asthma and COPD Drugs" BCC Research Market Forecasting: 1-159 (2012).
Nagavarapu "Pulmonary Drug Delivery Systems: Technologies and Global Markets" BCC Research Market Forecasting: 1-222 (2012).
Jungas et al. "Glutathione levels and BAX activation during apoptosis due to oxidative stress in cells expressing wild-type and mutant cystic fibrosis transmembrane conductance regulator" Journal of Biological Chemistry 277(31):27912-27918 (2002).
Kariya et al. "A role for CFTR in the elevation of glutathione levels in the lung by oral glutathione administration" American Journal of Phy siology-Lung Cellular and Molecular Physiology 292(6):L1590-L1597 (2007).
Kogan et al. "CFTR directly mediates nucleotide-regulated glutathione flux" The EMBO Journal 22(9):1981-1989 (2003).
Korytina, GF "Polymorphism of glutathione S-transferase M1 and P1 in patients with cystic fibrosis and chronic respiratory diseases" Russian Journal of Genetics 40(3):314-320 (2004).
Lands et al. "Lymphocyte Glutathione Levels in Children with Cystic Fibrosis" Chest 116:201-205 (1999).

(56) References Cited

OTHER PUBLICATIONS

Lands et al. "Total Plasma Antioxidant Capacity in Cystic Fibrosis" Pediatric Pulmonology 29(2):81-87 (2000).
Lands, Larry C. "Nutrition in pediatric lung disease" Paediatric Respiratory Reviews 8(4):305-312 (2007).
Laskowska-Klita et al. "Antioxidant status in erythrocytes of cystic fibrosis children" Acta Biochimica Polonica 48(1):283-285 (2001).
Lasry et al. (Nature Immunology, 17, 230-240, 2016).
Li et al. "Spatiotemporal Coupling of cAMP Transporter to CFTR Chloride Channel Function in the Gut Epithelia" Cell 131(5):940-951 (2007).
Lima et al. "Cystic fibrosis transmembrane conductance regulator gene mutations and glutathione S-transferase null genotypes in cystic fibrosis patients in Brazil" Journal Brasileiro De Pneumologia 38(1):50-56 (2012).
Lothian et al. "Effect of whey protein to modulate immune response in children with atopic asthma" International Journal of Food Sciences and Nutrition 57(3-4):204-211 (2006).
Madarasi et al. "Antioxidant Status in Patients with Cystic Fibrosis" Annals of Nutrition and Metabolism 44(5-6):207-211 (2000).
Martin et al. "Host-microbe interactions in distal airways: relevance to chronic airway diseases" European Respiratory Review 24:78-91 (2015).
McKone et al. "Variants in the Glutamate-Cysteine-Ligase Gene Are Associated with Cystic Fibrosis Lung Disease" American Journal of Respiratory and Critical Care Medicine 174(4):415-419 (2006).
Moskwa et al. "A Novel Host Defense System of Airways is Defective in Cystic Fibrosis" American Journal Respir. Crit. Care Med . 175:174-183 (2007).
Murphy, Timothy F. "The role of bacteria in airway inflammation in exacerbations of chronic obstructive pulmonary disease" Current Opinion in Infectious Diseases 19(3):225-230 (2006).
None et al. "Residual Gravimetric Method to Measure Nebulizer Output" Journal of Aerosol Medicine 17(1):63-72 (2004).
O'Brien "Peroxidases" Chemico-Biological Interactions 129:113-139 (2000).
Pedemonte et al. "Thiocyanate Transport in Resting and IL-4 Stimulated Human Bronchial Epithelial Cells; Role of Pendrin and Anion Channels" J Immunol 178:5144-5153 (2007).
Perez-Vilar et al. "Reevaluating Gel-Forming Mucins' Roles in Cystic Fibrosis Lung Disease" Free Radical Biology and Medicine 37(10):1564-1577 (2004).
Pitt, Bruce R. "CFTR trafficking and signaling in respiratory epithelium" American Journal of Physiology-Lung Cellular and Molecular Physiology 281(1): L13-L15 (2001).
Prousky "The Treatment of Pulmonary Diseases and Respiratory-Related Conditions with inhaled (Nebulized or Aerosolized) Glutathione" eCAM 5(1):27-35 (2008).
Rada "The Pseudomonas Toxin Pyocyanin Inhibits the Dual Oxidase-Based Antimicrobial System as It Imposes Oxidative Stress on Airway Epithelial Cells" J Immunol 181:4883-4893 (2008).
Remund et al. "Infections Relevant to Lung Transplantation" Proceedings of the American Thoracic Society 6:94-100 (2009).
Rogan et al. "Loss of Microbicidal Activity and increased Formation of Biofilm Due to Decreased Lactoferrin Activity in Patients with Cystic Fibrosis" JID 190:1245-1253 (2004).
Roux et al. "*Mycobacterium abscessus*, pathogène émergent dans la mucoviscidose" Immuno-analyse et biologie specialisee 25(1):26-33 (2010) English Abstract Only.
Schwarzer et al. "Organelle redox of CF and CFTR-corrected airway epithelia" Free Radical Biology and Medicine 43(2):300-316 (2007).
Schwarzer et al. "Oxidative Stress Caused by Pyocyanin Impairs CFFR C1-Transport in Human Bronchial Epithelial Cells" Free Radical Biology and Medicine 45(12):1653-1662 (2008).
Sidlova et al. "Serum alpha-glutathione S-transferase as a sensitive marker of hepatocellular damage in patients with cystic fibrosis" Physiological Research 52(3):361-365 (2003).
Snyder et al. "Acute effects of aerosolized S-nitrosoglutathione in cystic fibrosis" American Journal of Respiratory and Critical Care Medicine 165(7):922-926 (2002).
Speich et al. "Epidemiology and Management of Infections after Lung Transplantation" Clinical Infectious Diseases 33(Suppl 1):S58-S65 (2001).
Szentpetery et al. "Functional Studies on the MRP1 Multidrug Transporter: Characterization of ABC-Signature Mutant Variants" Anticancer Research 24(2A):449-455 (2004).
Thomas et al. "Lactoperoxidase, peroxide, thiocyanate antimicrobial system: correlation of sulfhydryl oxidation with antimicrobial action" Infect. Immun. 20(2):456-483 (1978).
Thome et al. "Novel SIN-1 Reactive Intermediates Modulate Chloride Secretion Across Murine Airway Cells" Free Radical Biology and Medicine 35(6):662-675 (2003).
Tirouvanziam et al. "High-dose oral N-acetylcysteine, a glutathione prodrug, modulates inflammation in cystic fibrosis" Proceedings of the National Academy of Sciences of the United States of America 103(12):4628-4633 (2006).
Toumoud et al. "Structural equations to model relationships between pulmonary function, fatty acids and oxidation in cystic fibrosis" Scandinavian Journal of Clinical & Laboratory Investigation 69(1):36-44 (2009).
Vasu et al. "Evaluation of thiol-based antioxidant therapeutics in cystic fibrosis sputum: Focus on myeloperoxidase" Free Radical Research 45(2):165-176 (2011).
Velsor et al. "Antioxidant imbalance in the lungs of cystic fibrosis transmembrane conductance regulator protein mutant mice" American Journal of Physiology-Lung Cellular and Molecular Physiology 281(1):L31-L38 (2001).
Venglarik et al. "Hypochlorous acid alters bronchial epithelial cell membrane properties and prevention by extracellular glutathione" Journal of Applied Physiology 95(6):2444-2452.
Vilela et al. "High hydrostatic pressure enhances whey protein digestibility to generate whey peptides that improve glutathione status in CFTR-deficient lung epithelial cells" Molecular Nutrition & Food Research 50(11): 1013-1029 (2006).
Vilela et al. "Inhibition of IL-8 release from CFTR-deficient lung epithelial cells following pre-treatment with femetinide" International Immunopharmacology 6(11):1651-1664 (2006).
Visca et al. "Improvement in clinical markers in CF patients using a reduced glutathione regimen: An uncontrolled, observational study" Journal of Cystic Fibrosis 7:433-436 (2008).
Wang et al. "Reversible silencing of CFTR chloride channels by glutathionylation" Journal of General Physiology 125(2):127-141 (2005).
Ward et al. "Lactoferrin and host defense" Biochem. Cell Biol. 80:95-102 (2002).
Willing et al. "Shifting the balance: antibiotic effects on host-microbiota mutualism" Nature Reviews Microbiology 9(4):233-243 (2011) (Abstract Only).
Dewan "Advanced Drug Delivery Systems: Technologies and Global Markets" BCC Research Market Forecasting: 1-278 (2011).
Dewan "Global Markets for Orphan Drugs" BCC Research Market Forecasting: 1-212 (2013).
Highsmith "Biologic Therapeutic Drugs: Technoiogies and Global Markets" BCC Research Market Forecasting: 1-168 (2013).
De Villiers, B.L., et al., "Optimizing MCPA (K-salt) activity with adjuvants," *South African Journal of Plant and Soil* 17(2):63-65, Taylor and Francis Ltd., United Kingdom (2000).
Klare, W., et al., "Glutathione-Disrupted Biofilms of Clinical Pseudomonas aeruginosa Strains Exhibit an Enhanced Antibiotic Effect and a Novel Biofilm Transcriptome," Antimicrobial Agents and Chemotherapy, 60(8): 4539-4551, American Society for Microbiology, United States (Aug. 2016).
Páez, P.L., et al., "Effect of the association of reduced glutathione and ciprofloxacin on the antimicrobial activity in *Staphylococcus aureus*," *FFMS Microbiology Letters*, 303(1): 101-105, Blackwell Publishing Ltd., United Kingdom (2010).
Sonni, F., et al., "Antioxidant action of glutathione and the ascorbic acid/gluthatione pair in a model white wine," *Journal of Agriculture and Food Chemistry* 59: 3940-3949, American Chemical Society, United States (2011).

(56) References Cited

OTHER PUBLICATIONS

Webassign, "Lab 10—Electrochemical Cells," General Chemistry II Labs, accessed at www.webassign.net/question_assets/ncsugenchem2021abv1/lab_10/manual.html, downloaded on Sep. 2, 2020, 8 pages.

Vasilenko, A., "Antibacterial activity of glutathione in carbapenemase-producing Klebsiella pneumoniae and Pseudomonas aeruginosa," a Master's Thesis submitted to the Faculty of Richard L. Conolly College, Long Island University in fulfillment of the requirements for the degree of Masters of Science, May 2013, 52 pages.

Aliberti, S., et al., "Criteria and definitions for the radiological and clinical diagnosis of bronchiectasis in adults for use in clinical trials: international consensus recommendations," *Lancet Respir Med* 2600(21):1-9, Elsevier, Netherlands (Sep. 2021).

Chalmers, J. D., and Hill, A. T., "Mechanisms of immune dysfunction and bacterial persistence in non-cystic fibrosis bronchiectasis," *Molecular Immunology* 55(1):27-34, Elsevier, Netherlands (Aug. 2013).

Chalm Ers, J. D., et al., "Bronchiectasis," *Nature Reviews Disease Primers* 4:45, 18 pages, Nature Publishing Group, United Kingdom (Nov. 2018).

King, P. T., "The pathophysiology of bronchiectasis," *Int J Chron Obstruct Pulmon Dis* 4:411-419, Dove Press, New Zealand (Nov. 2009).

Nosotti, M., et al., "Infections after lung transplantation," *Journal of Thoracic Disease* 10(6):3849-3868, Pioneer Bioscience Publishing Company, Hong Kong (Jun. 2018).

Okamoto, K., and Santos, C. A. Q., "Management and prophylaxis of bacterial and mycobacterial infections among lung transplant recipients," *Ann Transl Med* 8(6):413, 12 pages, AME Publishing Company, China (Mar. 2020).

Schäfer, J., et al., "Pathogenesis, imaging and clinical characteristics of CF and non-CF bronchiectasis," *BMC Pulm Med* 18(1):79, 11 pages, BioMed Central Ltd., United Kingdom (May 2018).

Fux, C.A., et al., "Can laboratory reference strains mirror 'real-world' pathogenesis?," Trends Microbiol. 13(2):58-63, Elsevier, Netherlands (2005).

Grosso-Becerra, M-V., et al., "Pseudomonas aeruginosa clinical and environmental isolates constitute a single population with high phenotypic diversity," BMC Genomics 15(318):1-14, BioMed Central, United Kingdom (2014).

Hanberger, H., et al., "Antibiotic Susceptibility Among Aerobic Gram-negative Bacilli in Intensive Care Units in 5 European Countries," JAMA 281 (1): 67-71, American Medical Association, United States (1999).

\* cited by examiner

TREATMENT OF RESPIRATORY TRACT DISEASES AND INFECTIONS WITH ASCORBIC ACID COMPOSITIONS

CROSS-REFERENCE TO RELATED APPLICATIONS

This application is a 35 U.S.C. § 371 national stage of International Patent Application No. PCT/US2017/062412, filed Nov. 17, 2017; which claims the priority benefit of U.S. Provisional Application No. 62/423,702, filed Nov. 17, 2016; and U.S. Provisional Application No. 62/423,721, filed Nov. 17, 2016, each of which is hereby incorporated in its entirety.

FIELD OF THE INVENTION

The present disclosure relates to compositions comprising glutathione, a glutathione derivative, a glutathione conjugate, a pharmaceutically-acceptable salt thereof, or any combination thereof and their use against clinically isolated bacteria.

BACKGROUND

Upper and lower respiratory tract diseases and infections constitute a major global health burden. Upper respiratory tract infections usually describe infections involving the nose, paranasal sinuses, pharynx, larynx, trachea, and bronchi; and lower respiratory infections affect the trachea, bronchial tubes, the bronchioles, and the lungs. Respiratory infections are the leading causes of death among all communicable diseases in the developed world. These diseases affect hundreds of millions of people, and each year, over four million people die from respiratory infections. European Centre for Disease Prevention and Control. Annual epidemiological report 2014—Respiratory tract infections. Stockholm: ECDC; 2014.

Lower respiratory infections from chronic inflammatory airway diseases present in multiple airway disorders and diseases, including, for example, lung transplant patients and patients with cystic fibrosis (CF). An underlying issue in chronic inflammatory airway diseases is bacterial infection. Many different bacterial strains, including *Pseudomonas aeruginosa*, are associated with respiratory bacterial infection. Sanchez et al., PLoS One. 2014; 9(10); Varga et al., BMC Genomics. 2015; 16:883; Wagner et al. Chest. 2005; 128(2):912-9. In addition to *Pseudomonas aeruginosa*, clinical isolates from samples of bacterial infections include both Gram negative and Gram positive bacteria, e.g., *Burkholderia cepacia* (Schwab et al. Infect Immun. 82(11): 4729-45 (2014)), *Staphylococcus aureus* (Zhao et al., Proc Natl Acad Sci USA. 2012 Apr. 10; 109(15):5809-14; Shields et al., J Heart Lung Transplant. 2012 November; 31(11): 1199-206), and Methicillin-resistant *Staphylococcus aureus* (Shields et al. J Heart Lung Transplant. 2012 November; 31(11):1199-206). Co-infection of multiple species of bacteria in pulmonary airways has also been reported. Schwab et al., Infect Immun. 2014; 82(11):4729-45; Zhao et al., Proc Natl Acad Sci USA. 2012 Apr. 10; 109(15):5809-14.

Models for evaluating in vivo efficacy of antimicrobials typically rely on in vitro testing of a *Pseudomonas* lab isolate (PAO1), and focus on bacterial biofilm formation after plating. The original PAO1 isolate was obtained in the 1980s from a burn lesion, but there are now many subtypes of PAO1 (also called "lab-based" *Pseudomonas aeruginosa*) that have been isolated by different laboratories. Klockgether et al. (2010) 192(4):1113-21. There are a number of issues with PAO1 as a surrogate for in vivo efficacy against clinical isolates (CIs). For example, PAO1 differs from clinical isolates of *Pseudomonas aeruginosa* in a number of ways. Genetically, CIs have a hypermutated genome and increased resistance to certain drugs compared to PAO1. Varga et al., BMC Genomics 16:883 (2015). CIs respond differently to a co-culture environment. See, e.g., Schwab et al., Infect Immun. 82(11):4729-45 (2014). And, CIs exhibit phenotypic differences such as cell motility and metabolic expression patterns compared to PAO1. Varga et al., BMC Genomics 16:883 (2015). Because of at least these issues, PAO1 is not an adequate surrogate for clinical *Pseudomonas aeruginosa* isolates from respiratory samples.

Thus, there remains a need in the art for in vivo treatment of clinical isolates associated with respiratory tract infections.

BRIEF SUMMARY

The present disclosure provides a method of inhibiting or reducing growth of a clinical isolate bacteria comprising contacting the clinical isolate with a composition comprising glutathione, a glutathione derivative, a glutathione conjugate, a pharmaceutically-acceptable salt thereof, or any combination thereof.

In another embodiment, the present disclosure also provides a method of inhibiting or reducing formation of a clinical isolate bacteria biofilm comprising contacting the clinical isolate with a composition comprising glutathione, a glutathione derivative, a glutathione conjugate, a pharmaceutically-acceptable salt thereof, or any combination thereof.

In another embodiment, the present disclosure provides a method of treating or reducing symptoms in a subject suffering from or at risk for a clinical isolate bacterial infection comprising contacting the clinical isolate with a composition comprising glutathione, a glutathione derivative, a glutathione conjugate, a pharmaceutically-acceptable salt thereof, or any combination thereof.

In some embodiments, the clinical isolate comprises two or more clinical isolates.

In some embodiments, the clinical isolate is Gram negative. In some embodiments, the Gram negative clinical isolate is selected from the group consisting of *Burkholderia cepacia*, mucoid *Pseudomonas aeruginosa*, nonmucoid *Pseudomonas aeruginosa*, and any combination thereof.

In other embodiments, the clinical isolate is Gram positive. In some embodiments, the Gram positive clinical isolate is *Staphylococcus aureus*, Methicillin-resistant *Staphylococcus aureus* (MRSA), or both.

In some embodiments, two or more clinical isolates of the disclosure comprise a combination of Gram negative and Gram positive clinical isolates.

In some embodiments, the clinical isolate is mucoid. In some embodiments, the clinical isolate is clinical mucoid *Pseudomonas aeruginosa*.

In some embodiments, the clinical isolate is non-mucoid. In some embodiments, the clinical isolate is clinical non-mucoid *Pseudomonas aeruginosa*.

In some embodiments, the clinical isolate is aerobic. In some embodiments, the aerobic clinical isolate is selected from the group consisting of *Pseudomonas aeruginosa*, *Burkholderia cepacia*, *Staphylococcus aureus*, Methicillin-resistant *Staphylococcus aureus* (MRSA), and any combination thereof.

In other embodiments, the clinical isolate is anaerobic or aerotolerant. In some embodiments, the clinical isolate is selected from the group consisting of *Burkholderia cepacia, Pseudomonas aeruginosa, Staphylococcus aureus*, Methicillin-resistant *Staphylococcus aureus* (MRSA), *Klebsiella pneumoniae*, and any combination thereof.

In some embodiments the clinical isolate can grow under the aerobic conditions with nitrate. In some embodiments, the clinical isolate can grow under anaerobic or aerotolerant conditions with nitrate.

In some embodiments, the clinical isolate lives extracellularly. In some embodiments, the extracellular clinical isolate is selected from the group consisting of *Burkholderia cepacia, Pseudomonas aeruginosa, Staphylococcus aureus*, Methicillin-resistant *Staphylococcus aureus* (MRSA), and any combination thereof.

In some embodiments, the clinical isolate is multidrug resistant. In some embodiments, the clinical isolate is selected from the group consisting of mucoid *Pseudomonas aeruginosa*, non-mucoid *Pseudomonas aeruginosa, Staphylococcus aureus*, Methicillin-resistant *Staphylococcus aureus, Burkholderia cepacia*, or any combination thereof.

In some embodiments, the composition of the disclosure further comprises a bicarbonate and/or a pH modifier. In some embodiments, the bicarbonate is selected from the group consisting of sodium bicarbonate or potassium bicarbonate. In some embodiments, the pH modifier is selected from the group consisting of ascorbic acid, citric acid, sodium citrate, sodium bicarbonate, potassium bicarbonate, dibasic sodium phosphate, magnesium oxide, calcium carbonate, magnesium hydroxide, buffers (e.g., acetate buffers, citrate buffers, phosphate buffers, lactic acid buffers, and borate buffers, and any combination thereof), fat-soluble fatty acid esters of ascorbic acid (vitamin C) (e.g., alone or in combination with a-hydroxy acids), oxidation resistant saturated fatty acid esters of ascorbic acid (e.g., ascorbyl laurate, ascorbyl myristate, ascorbyl palmitate, ascorbyl stearate, and ascorbyl behenate, and any combination thereof), and any combination thereof. In a preferred embodiment, the pH modifier is ascorbic acid. In some embodiments, the composition has a pH between about 3.0 to 14.0.

In some embodiments, contacting the clinical isolate with the composition thereby inhibits or reduces growth of a clinical isolate bacteria.

In some embodiments, the clinically efficacious MIC range of the composition is about 1%-50%, about 1%-40%, about 5%-50%, about 5%-40%, about 5%-35%, about 10%-50%, about 10%-40%, about 10%-35%, or about 12%-32%.

In some embodiments of the present disclosure, the growth of at least two, at least three, at least four, at least five, or at least six clinical isolates is reduced. In some embodiments, the growth of the clinical isolate is reduced in the presence of nitrate. In some embodiments, the clinical isolate is sensitized to an antibiotic to which the clinical isolate was tolerant or resistant prior to contact with the composition. In some embodiments, the antibiotic is selected from the group consisting of tobramycin, Colistin, ceftazidime, cefepime, meropenem, minocycline, trimethoprim-sulfamethoxazole, ticarcillin-clavulanate, ciprofloxacin, and cayston.

In some embodiments, the clinical isolate is resistant to cationic protein treatment. In some embodiments, the clinical isolate that is resistant to cationic protein treatment is *Staphylococcus aureus*, Methicillin-resistant *Staphylococcus aureus* (MRSA), *Pseudomonas aeruginosa, Burkholderia cepacia*, or any combination thereof.

In some embodiments, the growth reduction is at least 50%. In some embodiments, the growth is reduced in vitro. In some embodiments, the growth is reduced in vivo.

In some embodiments, the subject has a pulmonary or airway disease or disorder. In some embodiments, the pulmonary or airway disorder is selected from the group consisting of chronic inflammatory lung disease, pulmonary fibrosis, pulmonary vasculitis, pulmonary sarcoidosis, inflammation and/or infection associated with lung transplantation, acute or chronic lung rejection and/or dysfunction, pulmonary artery hypertension, bronchitis, sinusitis, asthma, cystic fibrosis, bacterial infection, fungal infection, parasite infection, viral infection, chronic obstructive pulmonary disease (COPD), bronchiolitis obliterans syndrome (BOS), primary ciliary dyskinesia (PCD), alveolar protienosis, idiopathic pulmonary fibrosis, eosinophilic pneumonia, eosinophilic bronchitis, acute respiratory distress syndrome (ARDS), inflammation and/or infection associated with mechanical ventilation, ventilator-associated pneumonia, asbestos-related airway disorder or disease, dust-related airway disorder or disease, silicosis, and radiation or chemical agent-related airway disease or disorder, and any combination thereof.

In some embodiments, the pulmonary or airway disease or disorder is selected from the group consisting of chronic inflammatory lung disease, an inflammation and/or infection associated with lung transplantation, acute or chronic lung rejection or dysfunction, asthma, cystic fibrosis, or chronic obstructive pulmonary disease (COPD), or any combination thereof. In another embodiment, the pulmonary or airway disease or disorder is cystic fibrosis. In another embodiment, the subject is a lung transplant patient. In another embodiment, the subject is infected with a biofilm producing bacteria.

In some embodiments, the disclosure provides administering an additional therapeutic agent to the subject. In some embodiments, the additional therapeutic agent is an antibiotic. In another embodiment, administration of the composition with the antibiotic produces a synergistic reduction in growth. In some embodiments, one or more therapeutic agents are administered, and are selected from the group consisting of Fluticasone, Budesonide, Mometasone, Ciclesonide, Flunisolide, Beclomethasone, Albuterol, Levalbuterol, Ipratropium, Tiotropium, Formoterol, Arformoterol, Indacaterol, Aclidinium, Cayston, and Pirbuterol, and any combination thereof.

In some embodiments, the composition is administered in the presence of or in combination with nitrate, nitric oxide, and nitrosoglutathione.

In some embodiments, the compositions for use according to the methods herein comprises: (a) glutathione, a glutathione derivative, a glutathione conjugate, a pharmaceutically-acceptable salt thereof, or any combination thereof; and (b) an organic acid, wherein the molar ratio of (a) to (b) is about 0.5-1:1 and the pH of the formulation is at least 5.5. In some embodiments, the composition further comprises (c) a bicarbonate salt (e.g., sodium bicarbonate). In some embodiments, the composition does not include a bicarbonate salt.

In some embodiments, the molar ratio of (a):(b):(c) is about 0.1-0.5:0.5-1:1. In some embodiments, the molar ratio of (a):(b):(c) is about 0.4-0.5:0.5-1:1. In some embodiments, the molar ratio of (a):(b):(c) is about 0.4-0.5:0.5:1 or 0.4-0.5:1:1.

In some embodiments, the reduced glutathione in the composition is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the composition after storage of the composition for 4 weeks at about 5° C.

In some embodiments, the oxidized glutathione in the composition is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the composition after storage of the composition for 4 weeks (e.g., at 5° C. in a $N_2$ atmosphere and/or ambient atmosphere).

In some embodiments, the reduced ascorbic acid is more than about 80%, more than about 85%, more than about 86%, more than about 87%, more than about 88%, more than about 89%, or more than about 90% by weight of the total ascorbic acid in the composition after storage of the composition after storage of the composition for 4 weeks at about 5° C.

In some embodiments, the oxidized ascorbic acid in the composition is less than about 20%, less than about 18%, less than about 16%, less than about 15%, less than about 12%, less than about 10%, or less than about 9% by weight of the total ascorbic acid in the composition after storage of the composition for 4 weeks at about 5° C.

In some embodiments, the composition is stored under ambient conditions, e.g., without nitrogen sparging. In some embodiments, the composition is stored with nitrogen sparging.

In some embodiments, the pH of the composition is about 5.5 to about 10, about 5.5 to about 8, about 6 to about 10, or about 6 to about 8. In some embodiments, the pH is about 5.5, about 6.5, about 7.0, or about 7.5. In some embodiments, the pH of the composition is 7±1.5. In some embodiments, the pH of the composition is about 6.

In some embodiments, the composition is an aqueous solution, a dry powder, or lyophilized.

DETAILED DESCRIPTION

Definitions

To facilitate an understanding of the present invention, a number of terms and phrases are defined below.

As used in the present disclosure and claims, the singular forms "a," "an," and "the" include plural forms unless the context clearly dictates otherwise.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein means approximately ±10%. When the term "about" is used in conjunction with a numerical value or range, it modifies that value or range by extending the boundaries above and below the numerical values set forth. In general, the term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.)

"Clinical isolate bacteria" as used herein means a bacterial strain that has been isolated from a human subject or from a tissue sample taken from a human subject.

"Minimum inhibitory concentration" or "MIC" as used herein means the lowest concentration of an agent (e.g., an antibiotic and/or composition of the application) that will inhibit the visible growth of a bacteria species.

"Minimum bactericidal concentration" or "MBC" as used herein means the lowest concentration at which an agent (e.g., an antibiotic and/or composition of the application) will kill a bacteria species.

"Minimum biofilm eradication concentration" or "MBEC" as used herein means the lowest concentration of an agent (e.g., an antibiotic and/or composition of the application) that will inhibit the visible growth of a biofilm.

"Pharmaceutically acceptable" as used herein means safe and effective for use in humans. For example, a "pharmaceutically acceptable salt", as used herein, means those salts of the compounds disclosed herein that are safe and effective for use in a subject and that possess the desired biological activity of the compound.

"Biofilm" as used herein means a group of microorganisms, e.g., clinical isolate bacteria, in which cells of the microorganism stick to each other and often these cells adhere to a surface. In some embodiments, these adherent cells are embedded within a self-produced matrix of extracellular polymeric substance (EPS). In some embodiments, the biofilm comprises a single bacterial species. In other embodiments, the biofilm is a mixture of two or more species of bacteria.

"Mucoid bacteria" as used herein means alginate-producing bacteria.

"Nonmucoid bacteria" as used herein means bacteria that do not produce alginate.

"Aerobic" as used herein means an organism, e.g., bacteria that can survive and grow in an oxygenated environment.

"Anaerobic" or "anaerobe" as used herein means an organism, e.g., bacteria that do not require oxygen for growth. In some embodiments, the organism is an "obligate anaerobe", which means it is harmed by the presence of oxygen; an "aerotolerant organism", which means it cannot use oxygen for growth but tolerates its presence; or a "facultative anaerobe", which means it can grow without oxygen but will use oxygen if it is present.

"Extracellular" as used herein means outside a cell.

"Antibiotic resistance" refers to bacteria possessing a mechanism that makes an antibiotic ineffective at killing the bacteria. Exemplary mechanisms include, e.g., destruction of the antibiotic, antibiotic-target modification, and restricted penetration and/or efflux of the antibiotic. In some embodiments, the bacteria become antibiotic resistant due to a mutation.

"Multidrug resistance" (also referred to as "multiple drug resistance", "MDR", "multiresistance") as used herein means antimicrobial resistance shown by a species of microorganism, e.g., a species of bacteria, to multiple antimicrobial drugs, e.g., antibiotics.

"Antibiotic Tolerance" refers to specialized survivor (or persister) cells within a population of bacterial cells that are phenotypic variants (not mutants) that are non-growing dormant cells. Persisters are killed only slowly, if at all, by antibiotics and resume growth when antibiotic concentrations are lowered or stopped.

"Sensitized" as used herein means susceptibility of a microorganism, e.g., a bacteria, to an antimicrobial drug, e.g., an antibiotic.

"Synergistic effect" as used herein means an effect arising between two or more therapeutic agents, e.g., a composition disclosed herein and an antibiotic that produces an effect greater than the sum of the two or more therapeutic agent's individual effects.

"Inhibiting" as used herein means blocking or stopping, e.g., stopping bacterial growth.

"Reducing" as used herein means decreasing or lowering the amount of, e.g., lowering the amount of bacterial growth (e.g., as compared to a starting point or as compared between two or more groups).

"Treating" or "treatment" as used herein refers to partially or completely alleviating, ameliorating, improving, relieving, delaying onset of, inhibiting progression of, reducing severity of, and/or reducing incidence of one or more signs, symptoms or features of a disease.

By "subject" or "patient" is meant any subject, particularly a mammalian subject, for whom diagnosis, prognosis, or therapy is desired. In certain embodiments, the mammal is a human subject. In other embodiments, a subject is a human patient. In a particular embodiment, a subject is a human patient in need of treatment.

Administration "in combination with" one or more further therapeutic agents includes simultaneous (concurrent) or consecutive administration in any order.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes.

The term "pharmaceutical formulation" refers to a preparation which is in such form as to permit the biological activity of the active ingredient or active ingredients to be effective, and which contains no additional components which are unacceptably toxic to a subject to which the formulation would be administered. The formulation can be sterile.

An "effective amount" of a composition or active agent as disclosed herein is an amount sufficient to carry out a specifically stated purpose. An "effective amount" can be determined empirically and in a routine manner, in relation to the stated purpose.

The term "therapeutically effective amount" refers to an amount of composition or active agent as disclosed herein effective to "treat" a disease or disorder in a subject.

Clinical Isolates

In certain aspects, clinical isolate of the application can comprise a single bacterial strain or a combination (i.e., two or more) of bacterial strains. In certain embodiments, the clinical isolate is selected from the group consisting of *Pseudomonas aeruginosa, Staphylococcus aureus*, Methicillin-resistant *Staphylococcus aureus* (MRSA), *Actinobacter baumannii, Burkholderia pseudomallei, Burkholderia cepacia*, or any combination thereof.

In some embodiments, the clinical isolate is gram negative. In certain embodiments, the gram negative clinical isolate is selected from the group consisting of *Burkholderia cepacia, Pseudomonas aeruginosa, Actinobacter baumannii, Burkholderia pseudomallei*, or any combination thereof.

In some embodiments, the *Pseudomonas aeruginosa* is mucoidy or nonmucoid, or combination thereof.

In some embodiments, the clinical isolate is gram positive. In certain embodiments, the gram positive clinical isolate is selected from the group consisting of *Enterococcus, Streptococcus, Pneumococcus, Staphylococcus* (e.g., *Staphylococcus aureus* or Methicillin-resistant *Staphylococcus aureus* (MRSA)), and any combination thereof. In some embodiments, the Gram positive clinical isolate is *Staphylococcus aureus* or Methicillin-resistant *Staphylococcus aureus* (MRSA) or a combination thereof.

In some embodiments, the clinical isolate is mucoid. In certain embodiments, the mucoid clinical isolate is *Pseudomonas aeruginosa, Burkholderia cepacia*, and any combination thereof.

In some embodiments, the clinical isolate is non-mucoid. In certain embodiments, the clinical isolate is clinical non-mucoid *Pseudomonas aeruginosa*.

In some embodiments, the clinical isolate is aerobic. In certain embodiments, the aerobic clinical isolate is *Pseudomonas aeruginosa, Burkholderia cepacia, Staphylococcus aureus*, and Methicillin-resistant *Staphylococcus aureus* (MRSA), and any combination thereof. In certain embodiments, the aerobic condition is with nitrate. In certain embodiments, the aerobic condition is without nitrate.

In some embodiments, the clinical isolate is anaerobic or aerotolerant. In certain embodiments, the anaerobic or aerotolerant clinical isolate is selected from the group consisting of *Staphylococcus aureus*, Methicillin-resistant *Staphylococcus aureus* (MRSA), *Burkholderia cepacia, Pseudomonas aeruginosa, Staphylococcus aureus*, and any combination thereof. In certain embodiments, the anaerobic or aerotolerant condition is with nitrate. In certain embodiments, the anaerobic or aerotolerant condition is without nitrate.

In some embodiments, the clinical isolate can live extracellularly. In certain embodiments, the clinical isolate that can live extracellularly is *Burkholderia cepacia, Pseudomonas aeruginosa, Staphylococcus aureus*, and Methicillin-resistant *Staphylococcus aureus* (MRSA), and any combination thereof.

In some embodiments, the clinical isolate is multidrug resistant. In certain embodiments, the multidrug resistant clinical isolate is selected from the group consisting of *Staphylococcus aureus*, Methicillin-resistant *Staphylococcus aureus* (MRSA), *Pseudomonas aeruginosa, Burkholderia cepacia*, and any combination thereof.

In some embodiments, the clinical isolate is resistant to cationic protein treatment. In certain embodiments, the cationic protein treatment resistant clinical isolate is selected from the group consisting of *Pseudomonas aeruginosa, Burkholderia cepacia*, and any combination thereof.

*Pseudomonas aeruginosa*

In one embodiment, the clinical isolate bacteria are *Pseudomonas aeruginosa*.

*Pseudomonas aeruginosa* is a gram-negative bacterium that can cause infection, especially in patients with compromised host defense mechanisms. It is the most common pathogen isolated from patients who have been hospitalized longer than 1 week, and it is a frequent cause of nosocomial infections. Pseudomonal infections can be life-threatening.

*Pseudomonas aeruginosa* is a metabolically versatile bacterium that can cause a wide range of severe opportunistic infections in patients with compromised natural defenses. Predisposing conditions can include, e.g., a disrupted epithelial barrier (as found in burn wound patients), a depletion of neutrophils (for example, in a cancer patient receiving chemotherapy), the presence of a foreign body (a patient with a central venous catheter), and altered mucociliary clearance (e.g., in individuals with cystic fibrosis). *Pseudomonas aeruginosa* is intrinsically resistant to a large number of antibiotics and can acquire resistance to others, making treatment difficult. The propensity of *Pseudomonas aeruginosa* to form biofilms further protects it from antibiotics and from a host immune system. In some embodiments, the clinical isolate is the mucoid *Pseudomonas aeruginosa*. In some embodiments, the clinical isolate is the non-mucoid *Pseudomonas aeruginosa*.

*Pseudomonas aeruginosa* is commonly isolated from the respiratory tracts of individuals with cystic fibrosis and is associated with an accelerated decline in lung function in these patients. Chronic lung colonization and infection also occurs in bronchiectasis, a disease characterized by irreversible dilation of the bronchial tree, and in chronic obstructive pulmonary disease, a disease characterized by narrowing of the airways and abnormalities in air flow. In addition, *Pseudomonas aeruginosa* is one of the most common causes of hospital acquired pneumonia, especially in mechanically ventilated patients; it is associated with a particularly high mortality rate.

Exposure to various in vivo environments results in activation of a variety of metabolic patterns in *Pseudomonas aeruginosa* to defend itself against reactive nitrogen species. This can result in host mucoidy production.

Burkholderia cepacia

In another embodiment, the clinical isolate bacteria are *Burkholderia cepacia*.

*Burkholderia cepacia* is an aerobic gram-negative *bacillus* found in various aquatic environments. *Burkholderia cepacia* is an organism of low virulence and is a frequent colonizer of fluids used in the hospital (e.g., irrigation solutions, intravenous fluids). *Burkholderia cepacia* rarely causes infection in healthy hosts. Based on phenotypic and genotypic analyses, *Burkholderia cepacia* is one of the divided into 9 genovars that constitute the *Burkholderia cepacia* complex (BCC).

BCC is an important group of pathogens affecting patients with cystic fibrosis and chronic granulomatous disease as well as immunocompromised and hospitalized patients. Avgeri et al. Int J Antimicrob Agents. 2009 May; 33(5):394-404. BCC mutates frequently and acquires high levels of resistance to many antimicrobial agents. These bacteria are associated with clinical decline and mortality in chronic inflammatory airways diseases and even could develop multi-drug resistance. Although they generally are thought to be aerobic, some exhibit fermentation and nitrate respiration. Sass et al. ISME J. 2013 August; 7(8):1568-81.

*Staphylococcus aureus* and Methicillin-Resistant *Staphylococcus aureus* (MRSA)

In another embodiment, the clinical isolate bacteria are *Staphylococcus aureus* or methicillin-resistant *Staphylococcus aureus* (MRSA), both of which are Gram positive cocci.

*Staphylococcus aureus* is an important cause of pneumonia. These bacteria are specifically implicated in the development of pleuropulmonary infections, and generally co-localize with *Pseudomonas aeruginosa* or *Burkholderia cepacia* in chronic inflammatory airways diseases. Tong et al. Clin Microbiol Rev. 2015 July; 28(3):603-61. In one embodiment, *Staphylococcus aureus* is identified in lung transplant patients with acute and chronic rejection.

MRSA infection is caused by *Staphylococcus aureus* that has become resistant to many of the antibiotics used to treat ordinary staph infections. HA-MRSA infections typically are associated with invasive procedures or devices, such as surgeries, intravenous tubing or artificial joints. Community-associated MRSA (CA-MRSA) is another type of MRSA infection that has occurred in the wider community often among otherwise healthy people. This form, often begins as a painful skin boil. It is spread by skin-to-skin contact. At-risk populations include groups such as high school wrestlers, child care workers and people who live in crowded conditions.

Glutathione and Glutathione Conjugate Compositions

In certain aspects, the compositions of the application comprise glutathione, a glutathione derivative, a glutathione conjugate, a pharmaceutically-acceptable salt thereof, or any combination thereof.

In some embodiments, the composition comprises glutathione or a pharmaceutically-acceptable salt thereof.

Glutathione or "GSH" refers to a compound having the Formula A:

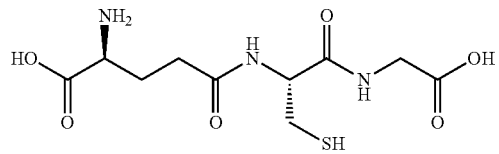 [SMILES: N[C@@H](CCC(=O)N[C@@H](CS)C(=O)NCC(=O)O)C(=O)O]

or a zwitterionic form thereof, e.g., a compound having the Formula B:

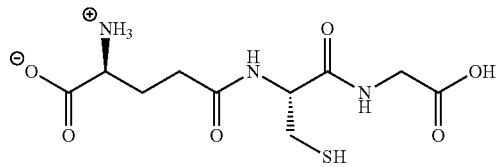 [SMILES: [NH3+][C@@H](CCC(=O)N[C@@H](CS)C(=O)NCC(=O)O)C(=O)[O-]]

Glutathione is the most abundant non-protein thiol in mammalian cells. It plays a role in the detoxification of xenobiotic compounds and in the antioxidation of reactive oxygen species and free radicals. See, e.g., Bray and Taylor, Canadian Journal of Physiology and Pharmacology 71:746-751 (1993).

In healthy individuals, there are high concentrations of GSH in the airway. However, in individuals with chronic inflammatory airway diseases, such as lung transplant patients, glutathione reserves are depleted.

In some embodiments, the composition comprises a glutathione-containing conjugate or a pharmaceutically-acceptable salt thereof. In certain embodiments, the glutathione-containing conjugate is metabolized to release glutathione, or a derivative thereof, upon administration to a subject. In some embodiments, the glutathione-containing conjugate is referred to herein as a "Conjugate Compound of the Disclosure" or "glutathione conjugate."

In one embodiment, a Conjugate Compound of the Disclosure is a compound having Formula I:

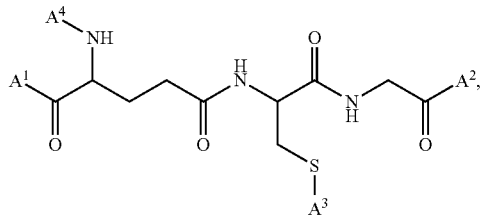

I and the pharmaceutically acceptable salts and solvates thereof, wherein, $A^1$ is —$OR^1$; $A^2$ is $Z^1$; $A^3$ is hydrogen; and $A^4$ is $R^{3a}$; or $A^1$ is $Z^1$; $A^2$ is —$OR^2$; and $A^3$ is hydrogen; and $A^4$ is $R^{3a}$; or $A^1$ is —$OR^1$; $A^2$ is —$OR^2$; and $A^3$ is $Z^3$; and $A^4$ is $R^{3a}$; or $A^1$ is $Z^2$; $A^2$ is —$OR^2$; and $A^3$ is hydrogen; and $A^4$ is $R^{3a}$; or $A^1$ is —$OR^1$; $A^2$ is $Z^2$; and $A^3$ is hydrogen; and $A^4$ is $R^{3a}$; or $A^1$ is —$OR^1$; $A^2$ is —$OR^2$; $A^3$ is hydrogen; and $A^4$ is $Z^3$; or $A^1$ and $A^2$ are each $Z^1$, and $A^3$ is hydrogen;

$Z^1$ is selected from the group consisting of:

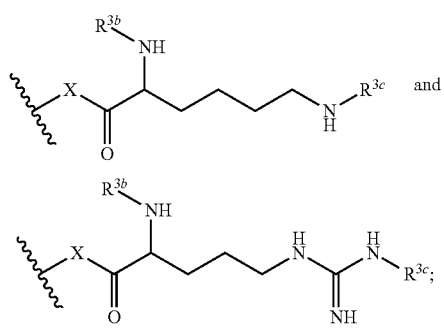

$Z^2$ is selected from the group consisting of:

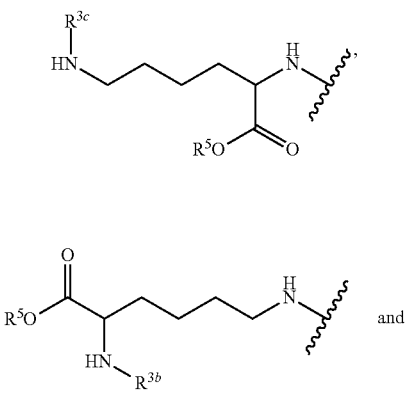

$Z^3$ is selected from the group consisting of:

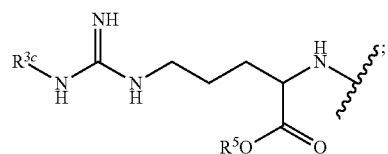

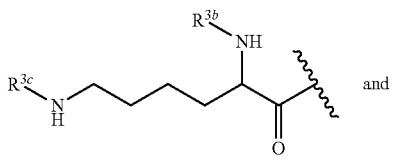

and

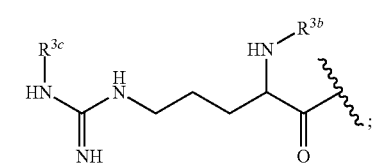

;

$R^1$ is selected from the group consisting of hydrogen and optionally substituted alkyl;

$R^2$ is selected from the group consisting of hydrogen and optionally substituted alkyl;

$R^{3a}$, $R^{3b}$, and $R^{3c}$ are each independently selected from the group consisting of hydrogen and protecting group;

X is selected from the group consisting of:

—O—;

—$O(CH_2)_mO$—;

—$OCH_2CH(R^4)O$—;

—$OCH(R^4)CH_2O$—; and

—$O(CH_2CH_2O)_n$—;

$R^4$ is:

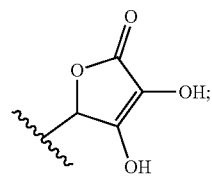 [SMILES: *C1OC(=O)C(O)=C1O]

m is 1, 2, 3, 4, 5, 6, 7, or 8;

n is 2, 3, 4, 5, 6, 7, or 8; and $R^5$ is selected from the group consisting of hydrogen and optionally substituted alkyl.

In another embodiment, a Conjugate Compound of the Disclosure is a compound having Formula I, and the pharmaceutically acceptable salts and solvates thereof, wherein m is 2, 3, 4, 5, 6, 7, or 8.

In another embodiment, a Conjugate Compound of the Disclosure is a compound having Formula II:

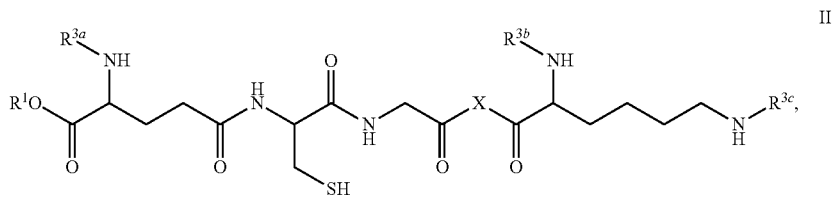

II or a pharmaceutically acceptable salt or solvate thereof, wherein R1, R3a, R3b, R3c, and X are as defined in connection with Formula I.

In another embodiment, a Conjugate Compound of the Disclosure is an enantiomerically enriched compound having any one or more of formulae of Table 1, and the pharmaceutically acceptable salts and solvates thereof, wherein $R^1$, $R^{3a}$, $R^{3b}$, $R^{3c}$, and X are as defined in connection with Formula I.

TABLE 1

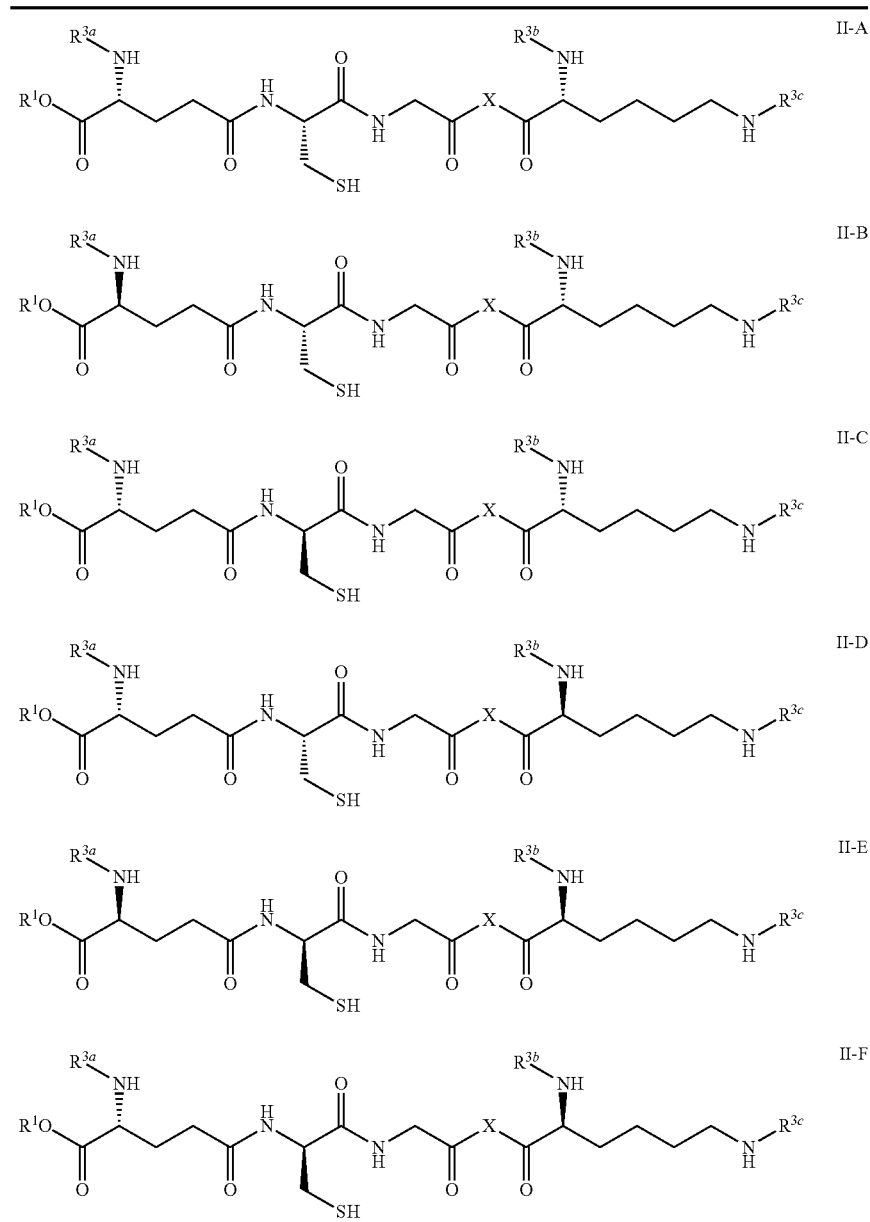

TABLE 1-continued

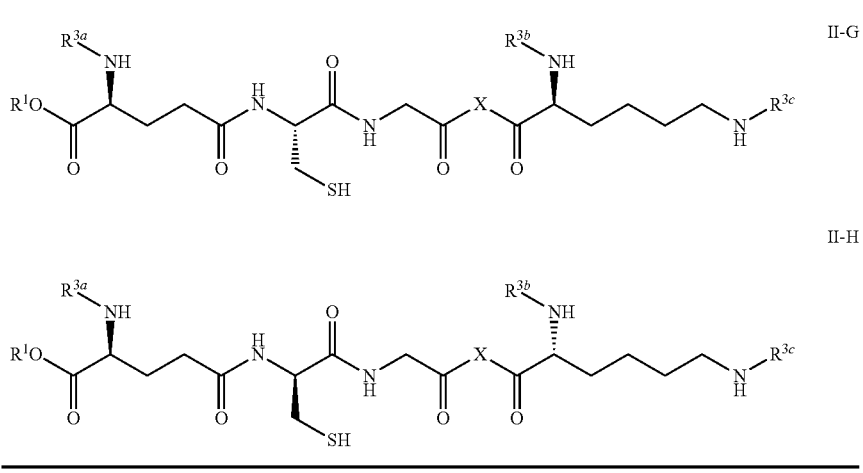

In another embodiment, a Conjugate Compound of the Disclosure is a compound having Formula II-A, and the pharmaceutically acceptable salts and solvates thereof. In another embodiment, a Conjugate Compound of the Disclosure is a compound having Formula II-B, and the pharmaceutically acceptable salts and solvates thereof. In another embodiment, a Conjugate Compound of the Disclosure is a compound having Formula II-C, and the pharmaceutically acceptable salts and solvates thereof. In another embodiment, a Conjugate Compound of the Disclosure is a compound having Formula II-D, and the pharmaceutically acceptable salts and solvates thereof. In another embodiment, a Conjugate Compound of the Disclosure is a compound having Formula II-E, and the pharmaceutically acceptable salts and solvates thereof. In another embodiment, a Conjugate Compound of the Disclosure is a compound having Formula II-F, and the pharmaceutically acceptable salts and solvates thereof. In another embodiment, a Conjugate Compound of the Disclosure is a compound having Formula II-G, and the pharmaceutically acceptable salts and solvates thereof. In another embodiment, a Conjugate Compound of the Disclosure is a compound having Formula II-H, and the pharmaceutically acceptable salts and solvates thereof.

In another embodiment, a Conjugate Compound of the Disclosure is a compound having Formula III:

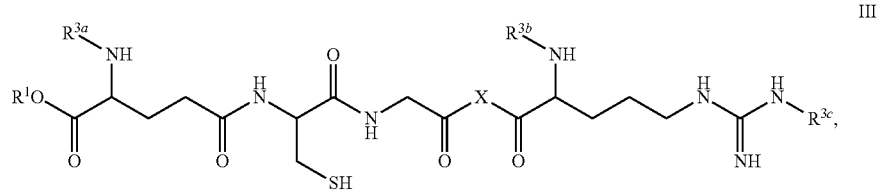

and the pharmaceutically acceptable salts and solvates thereof, wherein $R^1$, $R^{3a}$, $R^{3b}$, $R^{3c}$, and X are as defined in connection with Formula I.

In another embodiment, a Conjugate Compound of the Disclosure is an enantiomerically enriched compound having any one or more of the formulae of Table 2, and the pharmaceutically acceptable salts and solvates thereof, wherein $R^1$, $R^{3a}$, $R^{3b}$, $R^{3c}$, and X are as defined in connection with Formula I.

TABLE 2

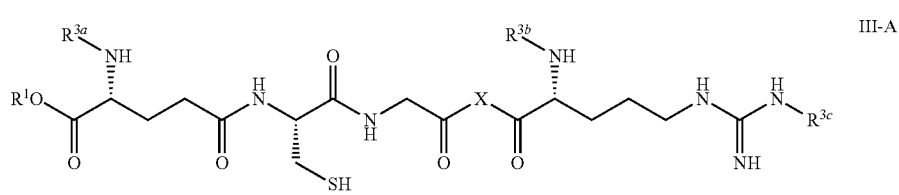

TABLE 2-continued

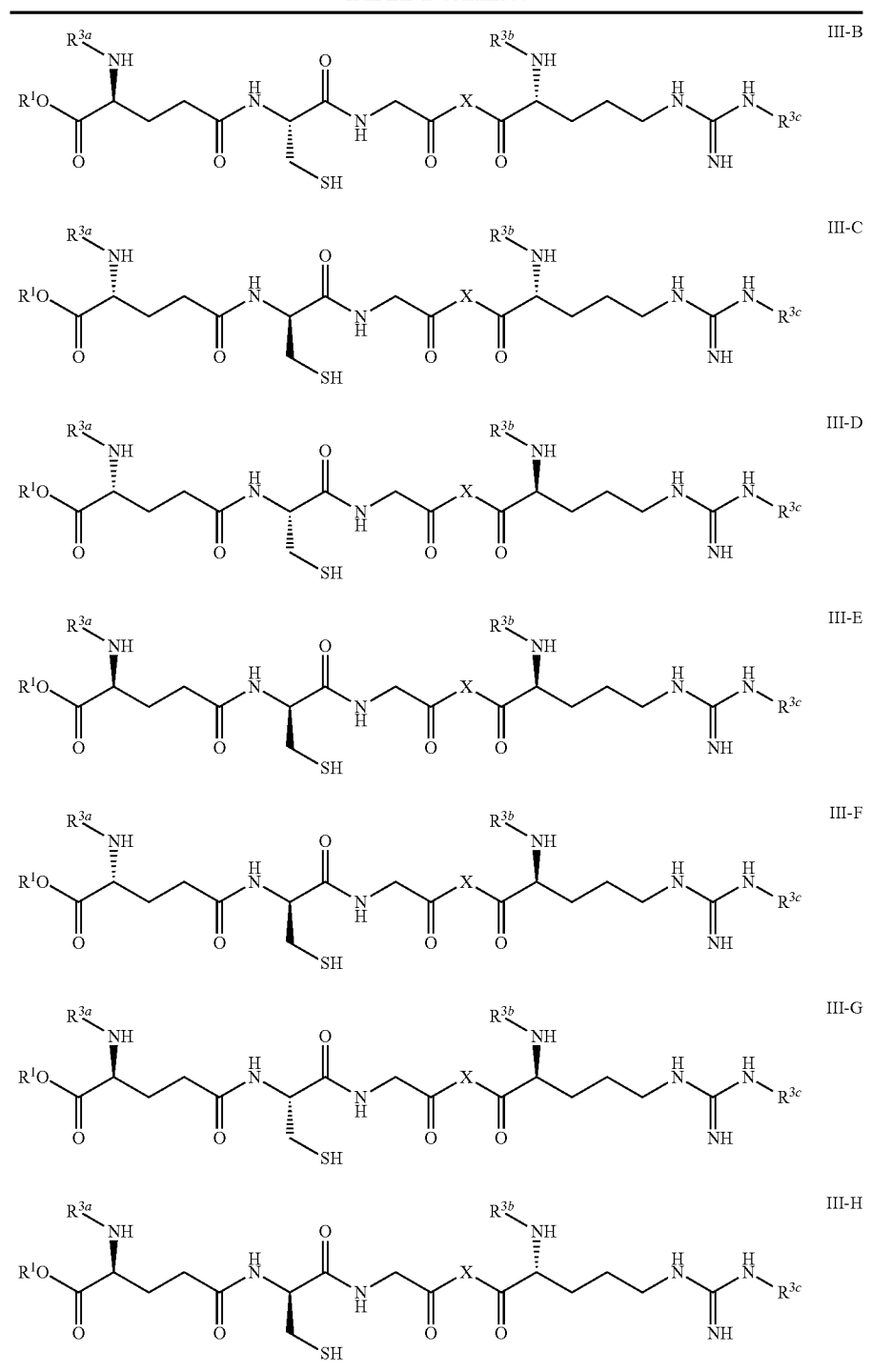

In another embodiment, a Conjugate Compound of the Disclosure is a compound having Formula III-A, and the pharmaceutically acceptable salts and solvates thereof. In another embodiment, a Conjugate Compound of the Disclosure is a compound having Formula III-B, and the pharmaceutically acceptable salts and solvates thereof. In another embodiment, a Conjugate Compound of the Disclosure is a compound having Formula III-C, and the pharmaceutically acceptable salts and solvates thereof. In another embodiment, a Conjugate Compound of the Disclosure is a compound having Formula III-D, and the pharmaceutically acceptable salts and solvates thereof. In another embodiment, a Conjugate Compound of the Disclosure is a compound having Formula III-E, and the pharmaceutically acceptable salts and solvates thereof. In another embodiment, a Conjugate Compound of the Disclosure is a compound having Formula III-F, and the pharmaceutically acceptable salts and solvates thereof. In another embodiment, a Conjugate Compound of the Disclosure is a compound having Formula III-G, and the pharmaceutically acceptable salts and solvates thereof. In another embodiment, a Conjugate Compound of the Disclosure is a compound having Formula III-H, and the pharmaceutically acceptable salts and solvates thereof.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein $R^1$ is hydrogen, and $R^{3a}$, $R^{3b}$, $R^{3c}$, and X are as defined in connection with Formula I. In another embodiment, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein $R^{3a}$, $R^{3b}$, and $R^{3c}$ are each independently selected from the group consisting of hydrogen, BOC, FMOC, and CBZ, and $R^1$ and X are as defined in connection with Formula I. In another embodiment, $R^1$ is hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein $R^{3a}$, $R^{3b}$, and $R^{3c}$ are each hydrogen, and $R^1$ and X are as defined in connection with Formula I. In another embodiment, $R^1$ is hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is —O—, and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is —O(CH$_2$)$_m$O— and m is 2 or 3, and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is —OCH$_2$CH(R$^4$)O—, and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is:

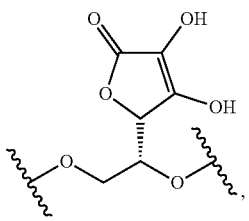 [SMILES: *OC[C@@H](O*)C1OC(=O)C(O)=C1O]

and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is:

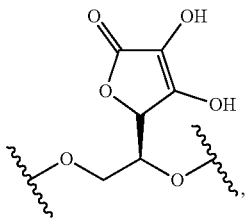 [SMILES: *OC[C@H](O*)C1OC(=O)C(O)=C1O]

and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is —OCH(R$^4$)CH$_2$O—, and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is:

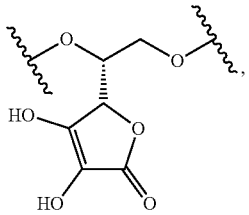 [SMILES: *OC[C@@H](O*)C1OC(=O)C(O)=C1O]

and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is:

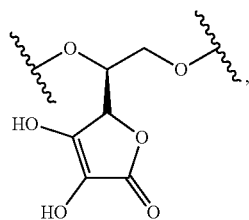 [SMILES: *OC[C@H](O*)C1OC(=O)C(O)=C1O]

and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having any one or more of Formulae I, II, II-A, II-B, II-C, II-D, II-E, II-F, II-G, II-H, III, III-A, III-B, III-C, III-D, III-E, III-F, III-G, or III-H, and the pharmaceutically acceptable salts and solvates thereof, wherein X is —O(CH$_2$CH$_2$O)$_n$— and n is 2 or 3, and $R^1$, $R^{3a}$, $R^{3b}$, and $R^{3c}$ are as defined in connection with Formula I. In another embodiment, $R^1$, $R^{3a}$, $R^{3b}$, and $R^{3c}$ are each hydrogen.

In another embodiment, a Conjugate Compound of the Disclosure is a compound having Formula IV:

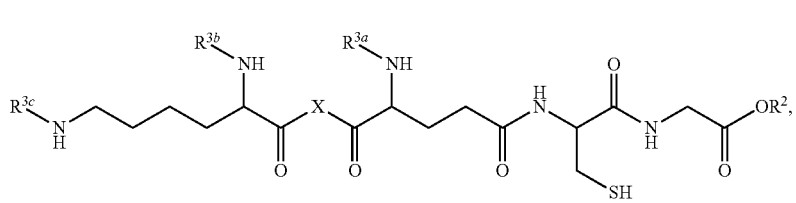

IV and the pharmaceutically acceptable salts and solvates thereof, wherein $R^2$, $R^{3a}$, $R^{3b}$, $R^{3c}$, and X are as defined in connection with Formula I.

In another embodiment, a Conjugate Compound of the Disclosure is an enantiomerically enriched compound having any one or more of the formulae of Table 3, and the pharmaceutically acceptable salts and solvates thereof, wherein $R^2$, $R^{3a}$, $R^{3b}$, $R^{3c}$, and X are as defined in connection with Formula I.

TABLE 3

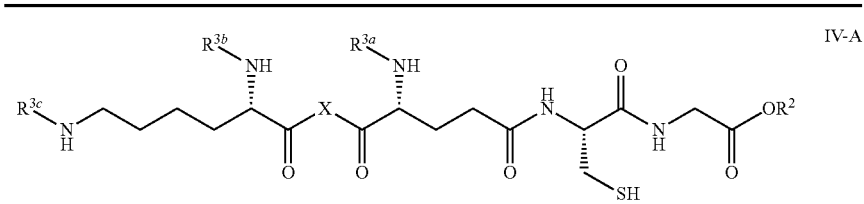

IV-A

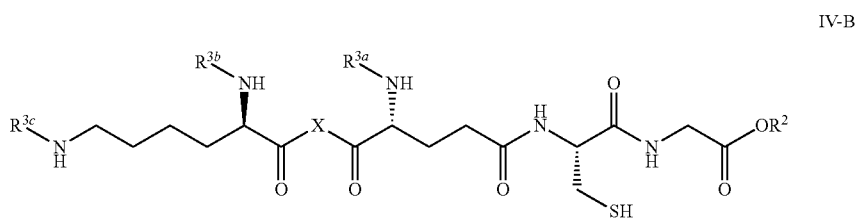

IV-B

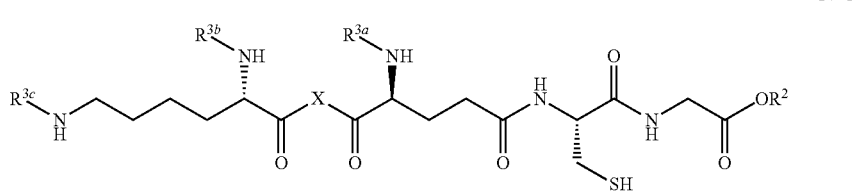

IV-C

TABLE 3-continued

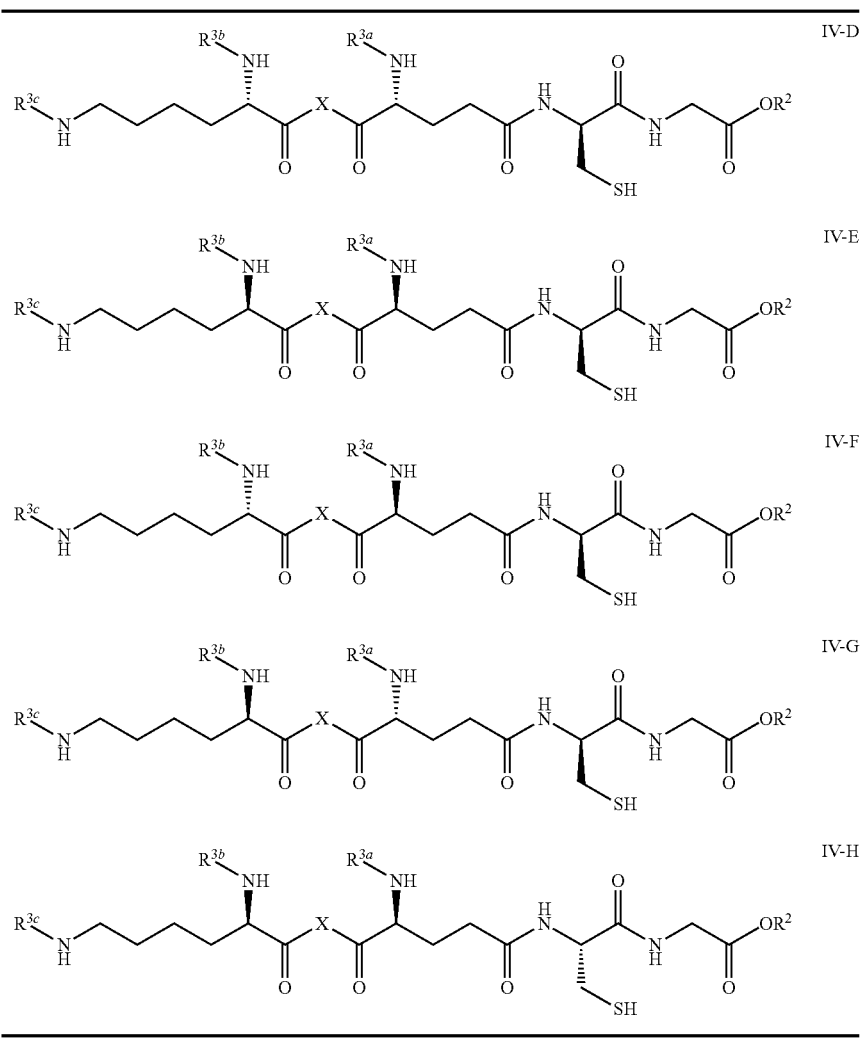

IV-D

IV-E

IV-F

IV-G

IV-H

In another embodiment, a Conjugate Compound of the Disclosure is a compound having Formula IV-A, and the pharmaceutically acceptable salts and solvates thereof. In another embodiment, a Conjugate Compound of the Disclosure is a compound having Formula IV-B, and the pharmaceutically acceptable salts and solvates thereof. In another embodiment, a Conjugate Compound of the Disclosure is a compound having Formula IV-C, and the pharmaceutically acceptable salts and solvates thereof. In another embodiment, a Conjugate Compound of the Disclosure is a compound having Formula IV-D, and the pharmaceutically acceptable salts and solvates thereof. In another embodiment, a Conjugate Compound of the Disclosure is a compound having Formula IV-E, and the pharmaceutically acceptable salts and solvates thereof. In another embodiment, a Conjugate Compound of the Disclosure is a compound having Formula IV-F, and the pharmaceutically acceptable salts and solvates thereof. In another embodiment, a Conjugate Compound of the Disclosure is a compound having Formula IV-G, and the pharmaceutically acceptable salts and solvates thereof. In another embodiment, a Conjugate Compound of the Disclosure is a compound having Formula IV-H, and the pharmaceutically acceptable salts and solvates thereof.

In another embodiment, a Conjugate Compound of the Disclosure is a compound having Formula V:

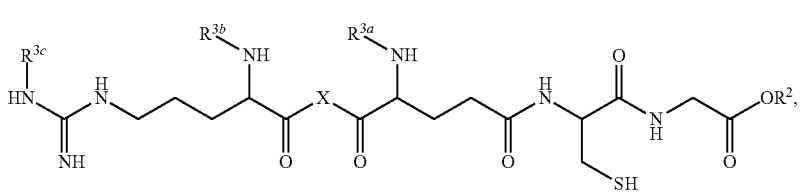

V and the pharmaceutically acceptable salts and solvates thereof, wherein $R^2$, $R^{3a}$, $R^{3b}$, $R^{3c}$, and X are as defined in connection with Formula I.

In another embodiment, a Conjugate Compound of the Disclosure is an enantiomerically enriched compound having any one or more of formulae of Table 4, and the pharmaceutically acceptable salts and solvates thereof, wherein $R^2$, $R^{3a}$, $R^{3b}$, $R^{3c}$, and X are as defined in connection with Formula I.

TABLE 4

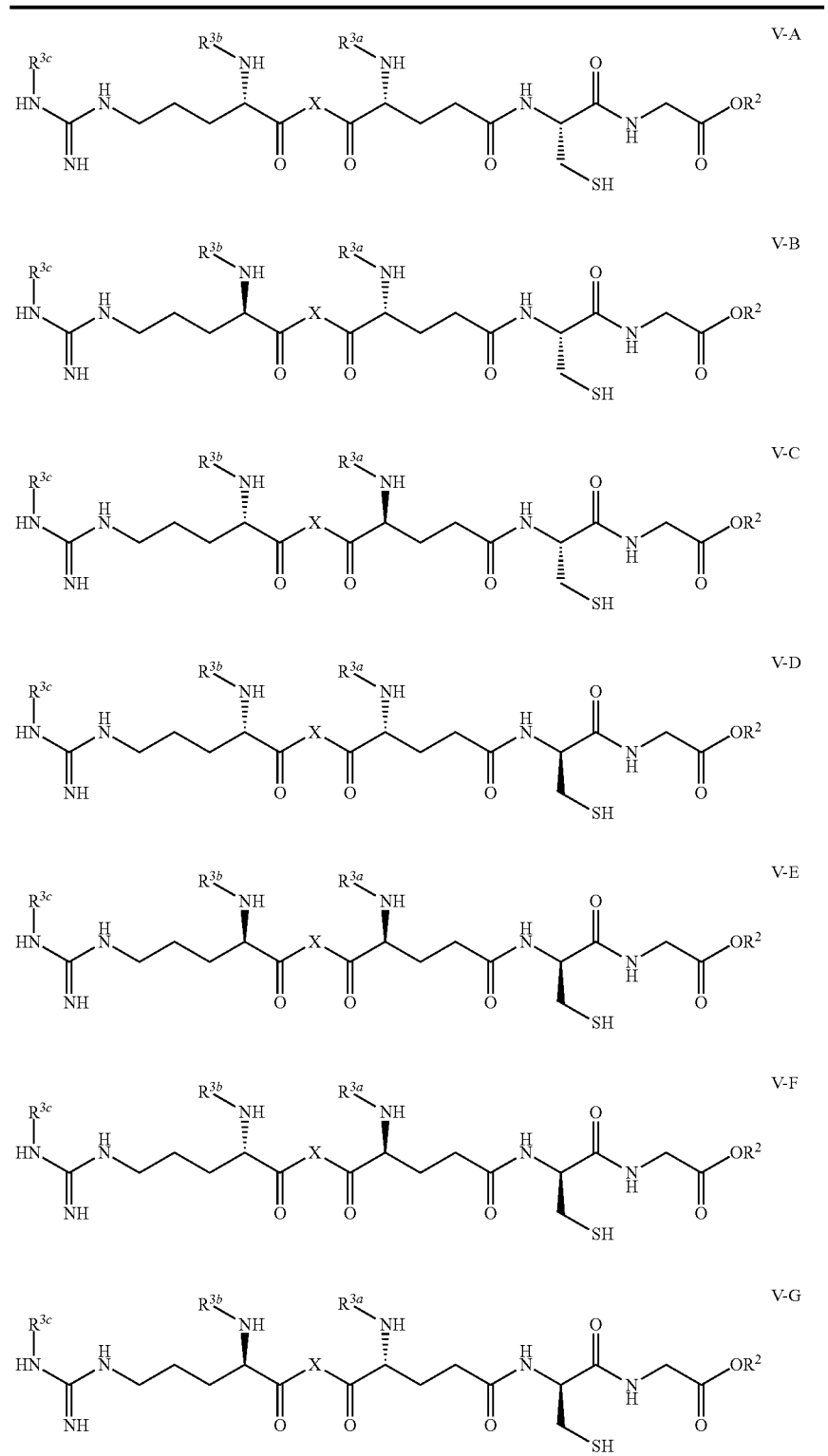

TABLE 4-continued

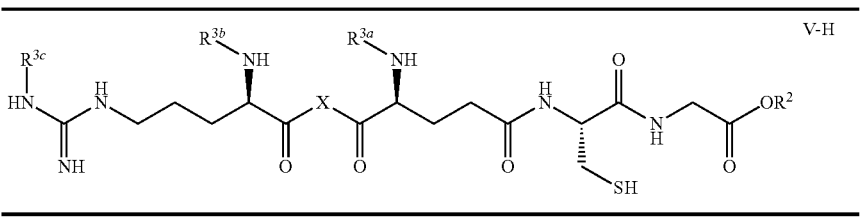

V-H

In another embodiment, a Conjugate Compound of the Disclosure is a compound having Formula V-A, and the pharmaceutically acceptable salts and solvates thereof. In another embodiment, a Conjugate Compound of the Disclosure is a compound having Formula V-B, and the pharmaceutically acceptable salts and solvates thereof. In another embodiment, a Conjugate Compound of the Disclosure is a compound having Formula V-C, and the pharmaceutically acceptable salts and solvates thereof. In another embodiment, a Conjugate Compound of the Disclosure is a compound having Formula V-D, and the pharmaceutically acceptable salts and solvates thereof. In another embodiment, a Conjugate Compound of the Disclosure is a compound having Formula V-E, and the pharmaceutically acceptable salts and solvates thereof. In another embodiment, a Conjugate Compound of the Disclosure is a compound having Formula V-F, and the pharmaceutically acceptable salts and solvates thereof. In another embodiment, a Conjugate Compound of the Disclosure is a compound having Formula V-G, and the pharmaceutically acceptable salts and solvates thereof. In another embodiment, a Conjugate Compound of the Disclosure is a compound having Formula V-H, and the pharmaceutically acceptable salts and solvates thereof.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, wherein $R^2$ is hydrogen, and $R^{3a}$, $R^{3b}$, $R^{3c}$, and X are as defined in connection with Formula I. In another embodiment, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is —O—, and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is —O(CH$_2$)$_m$O— and m is 2 or 3, and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is —OCH$_2$CH(R$^4$)O—, and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is:

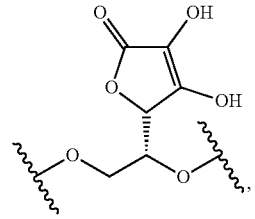 [SMILES: *OC[C@@H](O*)C1OC(=O)C(O)=C1O]

and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is:

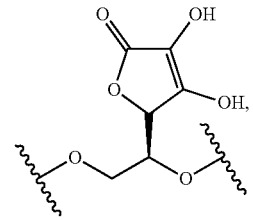 [SMILES: *OC[C@H](O*)C1OC(=O)C(O)=C1O]

and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is —OCH(R$^4$)CH$_2$O—, and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is:

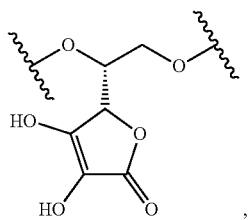 [SMILES: *OC[C@@H](O*)C1OC(=O)C(O)=C1O]

and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is:

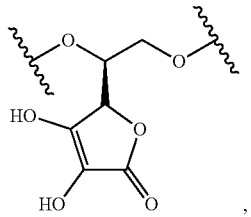 [SMILES: *OC[C@H](O*)C1OC(=O)C(O)=C1O]

and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having any one or more of Formulae I, IV, IV-A, IV-B, IV-C, IV-D, IV-E, IV-F, IV-G, IV-H, V, V-A, V-B, V-C, V-D, V-E, V-F, V-G, or V-H, and the pharmaceutically acceptable salts and solvates thereof, wherein X is $-O(CH_2CH_2O)_n-$ and n is 2 or 3, and $R^2$, $R^{3a}$, $R^{3b}$, and $R^{3c}$ are as defined in connection with Formula I. In another embodiment, $R^2$, $R^{3a}$, $R^{3b}$, and $R^{3c}$ are each hydrogen.

In another embodiment, a Conjugate Compound of the Disclosure is a compound having Formula VI:

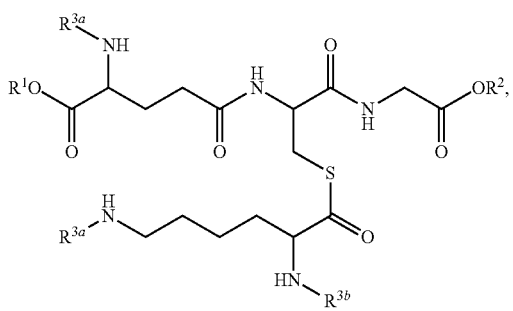

VI and the pharmaceutically acceptable salts and solvates thereof, wherein $R^1$, $R^2$, $R^{3a}$, $R^{3b}$, and $R^{3c}$ are as defined in connection with Formula I.

In another embodiment, a Conjugate Compound of the Disclosure is an enantiomerically enriched compound having any one or more of the formulae of Table 5, and the pharmaceutically acceptable salts and solvates thereof, wherein $R^1$, $R^2$, $R^{3a}$, $R^{3b}$, and $R^{3c}$, are as defined in connection with Formula I.

TABLE 5

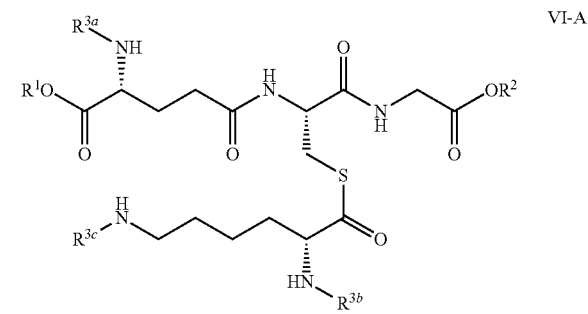

VI-A

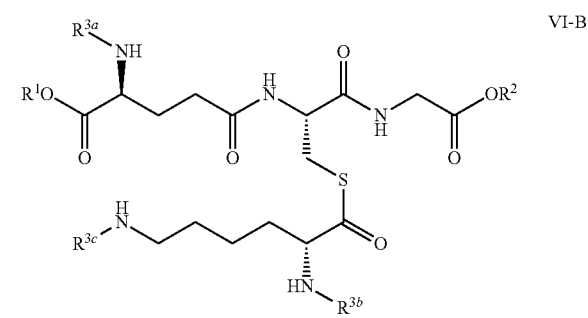

VI-B

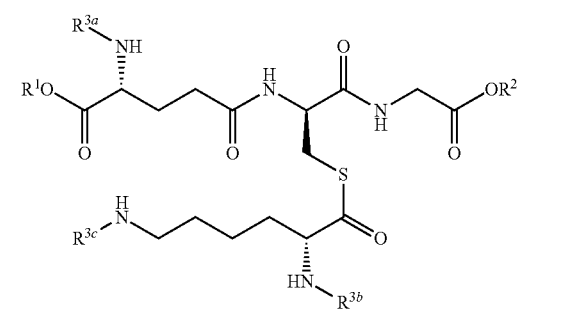

VI-C

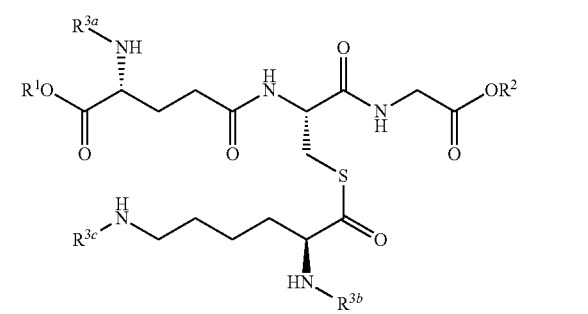

VI-D

TABLE 5-continued

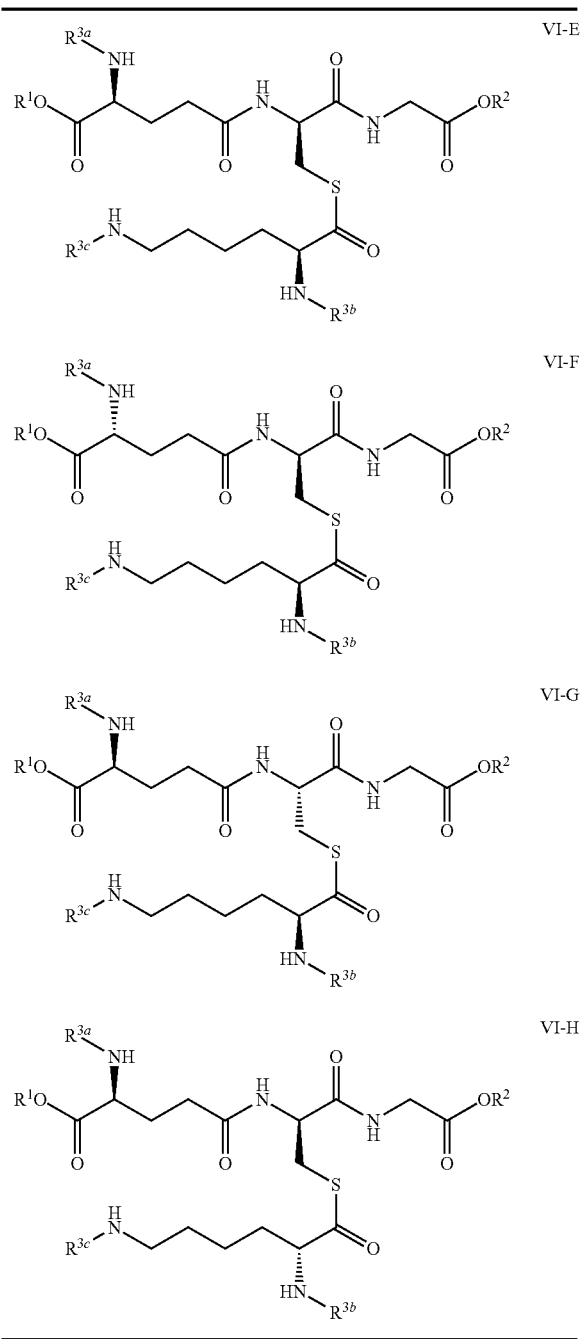

In another embodiment, a Conjugate Compound of the Disclosure is a compound having Formula VI-A, and the pharmaceutically acceptable salts and solvates thereof. In another embodiment, a Conjugate Compound of the Disclosure is a compound having Formula VI-B, and the pharmaceutically acceptable salts and solvates thereof. In another embodiment, a Conjugate Compound of the Disclosure is a compound having Formula VI-C, and the pharmaceutically acceptable salts and solvates thereof. In another embodiment, a Conjugate Compound of the Disclosure is a compound having Formula VI-D, and the pharmaceutically acceptable salts and solvates thereof. In another embodiment, a Conjugate Compound of the Disclosure is a compound having Formula VI-E, and the pharmaceutically acceptable salts and solvates thereof. In another embodiment, a Conjugate Compound of the Disclosure is a compound having Formula VI-F, and the pharmaceutically acceptable salts and solvates thereof. In another embodiment, a Conjugate Compound of the Disclosure is a compound having Formula VI-G, and the pharmaceutically acceptable salts and solvates thereof. In another embodiment, a Conjugate Compound of the Disclosure is a compound having Formula VI-H, and the pharmaceutically acceptable salts and solvates thereof.

In another embodiment, a Conjugate Compound of the Disclosure is a compound having Formula VII:

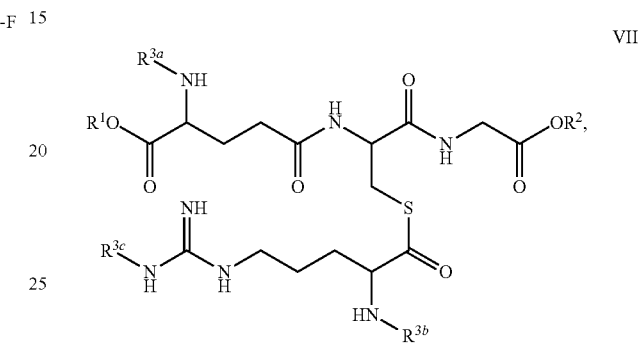

and the pharmaceutically acceptable salts and solvates thereof, wherein $R^1$, $R^2$, $R^{3a}$, $R^{3b}$, and $R^{3c}$ are as defined in connection with Formula I.

In another embodiment, a Conjugate Compound of the Disclosure is an enantiomerically enriched compound having any one or more of the formulae of Table 6, and the pharmaceutically acceptable salts and solvates thereof, wherein $R^1$, $R^2$, $R^{3a}$, $R^{3b}$, and $R^{3c}$, are as defined in connection with Formula I.

TABLE 6

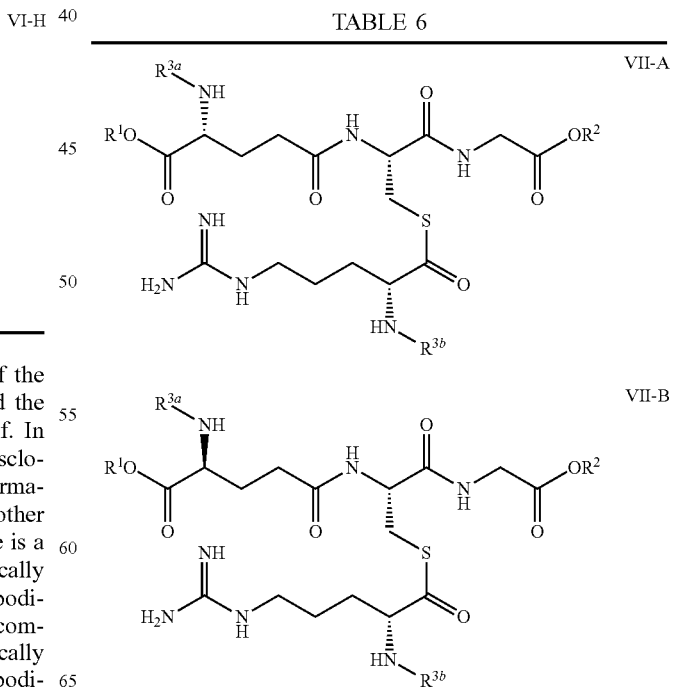

TABLE 6-continued

VII-C

VII-D

VII-E

VII-F

VII-G

VII-H

In another embodiment, a Conjugate Compound of the Disclosure is a compound having Formula VII-A, and the pharmaceutically acceptable salts and solvates thereof. In another embodiment, a Conjugate Compound of the Disclosure is a compound having Formula VII-B, and the pharmaceutically acceptable salts and solvates thereof. In another embodiment, a Conjugate Compound of the Disclosure is a compound having Formula VII-C, and the pharmaceutically acceptable salts and solvates thereof. In another embodiment, a Conjugate Compound of the Disclosure is a compound having Formula VII-D, and the pharmaceutically acceptable salts and solvates thereof. In another embodiment, a Conjugate Compound of the Disclosure is a compound having Formula VII-E, and the pharmaceutically acceptable salts and solvates thereof. In another embodiment, a Conjugate Compound of the Disclosure is a compound having Formula VII-F, and the pharmaceutically acceptable salts and solvates thereof. In another embodiment, a Conjugate Compound of the Disclosure is a compound having Formula VII-G, and the pharmaceutically acceptable salts and solvates thereof. In another embodiment, a Conjugate Compound of the Disclosure is a compound having Formula VII-H, and the pharmaceutically acceptable salts and solvates thereof.

In another embodiment, a Conjugate Compound of the Disclosure is a compound having any one or more of Formulae I, VI, VI-A, VI-B, VI-C, VI-D, VI-E, VI-F, VI-G, VI-H, VII, VII-A, VII-B, VII-C, VII-D, VII-E, VII-F, VII-G, or VII-H, wherein $R^1$ is hydrogen, and $R^2$, $R^{3a}$, $R^{3b}$, and $R^{3c}$ are as defined in connection with Formula I. In another embodiment, $R^2$ is hydrogen.

In another embodiment, a Conjugate Compound of the Disclosure is a compound having any one or more of Formulae I, VI, VI-A, VI-B, VI-C, VI-D, VI-E, VI-F, VI-G, VI-H, VII, VII-A, VII-B, VII-C, VII-D, VII-E, VII-F, VII-G, or VII-H, wherein $R^1$ and $R^2$ are each hydrogen, and $R^{3a}$, $R^{3b}$, and $R^{3c}$ are as defined in connection with Formula I. In another embodiment, $R^{3a}$, $R^{3b}$, and $R^{3c}$ are each independently selected from the group consisting of hydrogen, BOC, FMOC, and CBZ. In another embodiment, $R^{3a}$, $R^{3b}$, and $R^{3c}$ are each hydrogen.

In another embodiment, a Conjugate Compound of the Disclosure is a compound having Formula VIII:

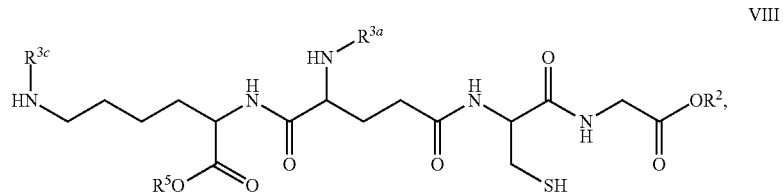

VIII and the pharmaceutically acceptable salts and solvates thereof, wherein $R^2$, $R^{3a}$, $R^{3c}$, and $R^5$ are as defined in connection with Formula I.

In another embodiment, a Conjugate Compound of the Disclosure is an enantiomerically enriched compound having any one or more of the formulae of Table 7, and the pharmaceutically acceptable salts and solvates thereof, wherein $R^2$, $R^{3a}$, $R^{3c}$, and $R^5$ are as defined in connection with Formula I.

TABLE 7

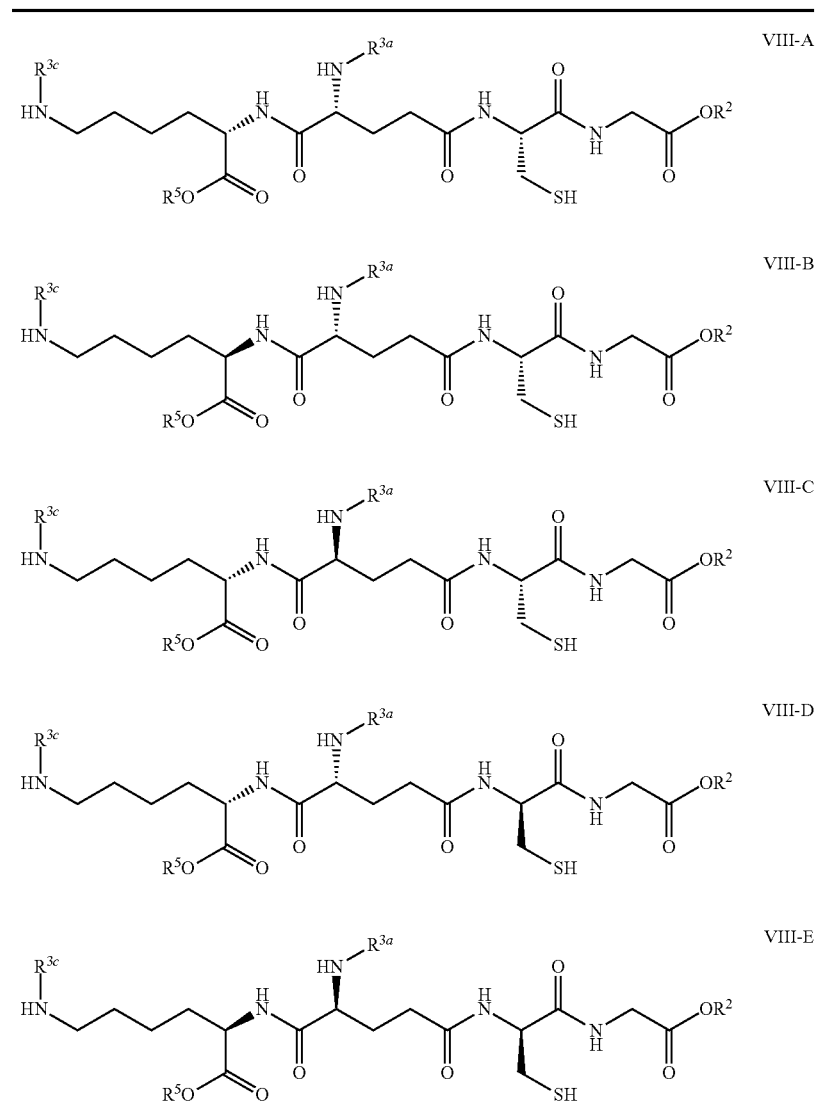

TABLE 7-continued

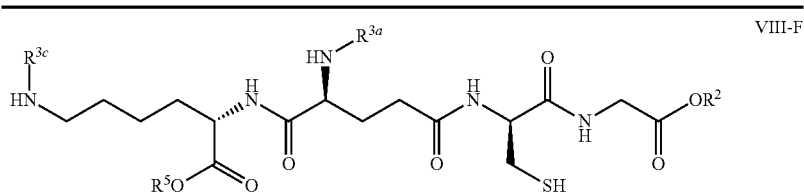

VIII-F

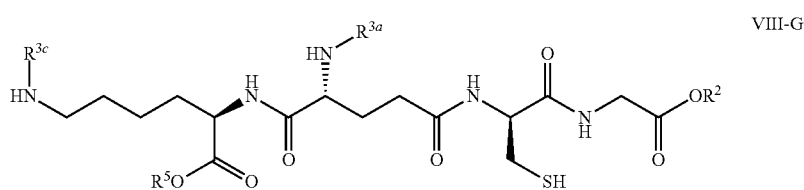

VIII-G

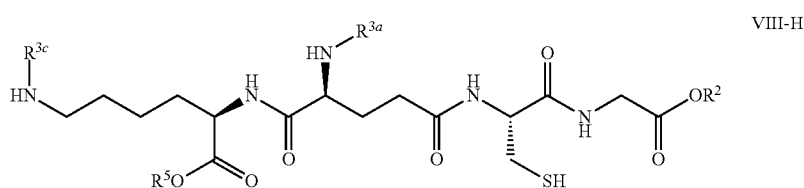

VIII-H

In another embodiment, a Conjugate Compound of the Disclosure is a compound having Formula VIII-A, and the pharmaceutically acceptable salts and solvates thereof. In another embodiment, a Conjugate Compound of the Disclosure is a compound having Formula VIII-B, and the pharmaceutically acceptable salts and solvates thereof. In another embodiment, a Conjugate Compound of the Disclosure is a compound having Formula VIII-C, and the pharmaceutically acceptable salts and solvates thereof. In another embodiment, a Conjugate Compound of the Disclosure is a compound having Formula VIII-D, and the pharmaceutically acceptable salts and solvates thereof. In another embodiment, a Conjugate Compound of the Disclosure is a compound having Formula VIII-E, and the pharmaceutically acceptable salts and solvates thereof. In another embodiment, a Conjugate Compound of the Disclosure is a compound having Formula VIII-F, and the pharmaceutically acceptable salts and solvates thereof. In another embodiment, a Conjugate Compound of the Disclosure is a compound having Formula VIII-G, and the pharmaceutically acceptable salts and solvates thereof. In another embodiment, a Conjugate Compound of the Disclosure is a compound having Formula VIII-H, and the pharmaceutically acceptable salts and solvates thereof.

In another embodiment, a Conjugate Compound of the Disclosure is a compound having Formula IX:

IX and the pharmaceutically acceptable salts and solvates thereof, wherein $R^2$, $R^{3a}$, $R^{3c}$, and $R^5$ are as defined in connection with Formula I.

In another embodiment, a Conjugate Compound of the Disclosure is an enantiomerically enriched compound having any one or more of the formulae of Table 8, and the pharmaceutically acceptable salts and solvates thereof, wherein $R^2$, $R^{3a}$, $R^{3c}$, and $R^5$ are as defined in connection with Formula I.

TABLE 8

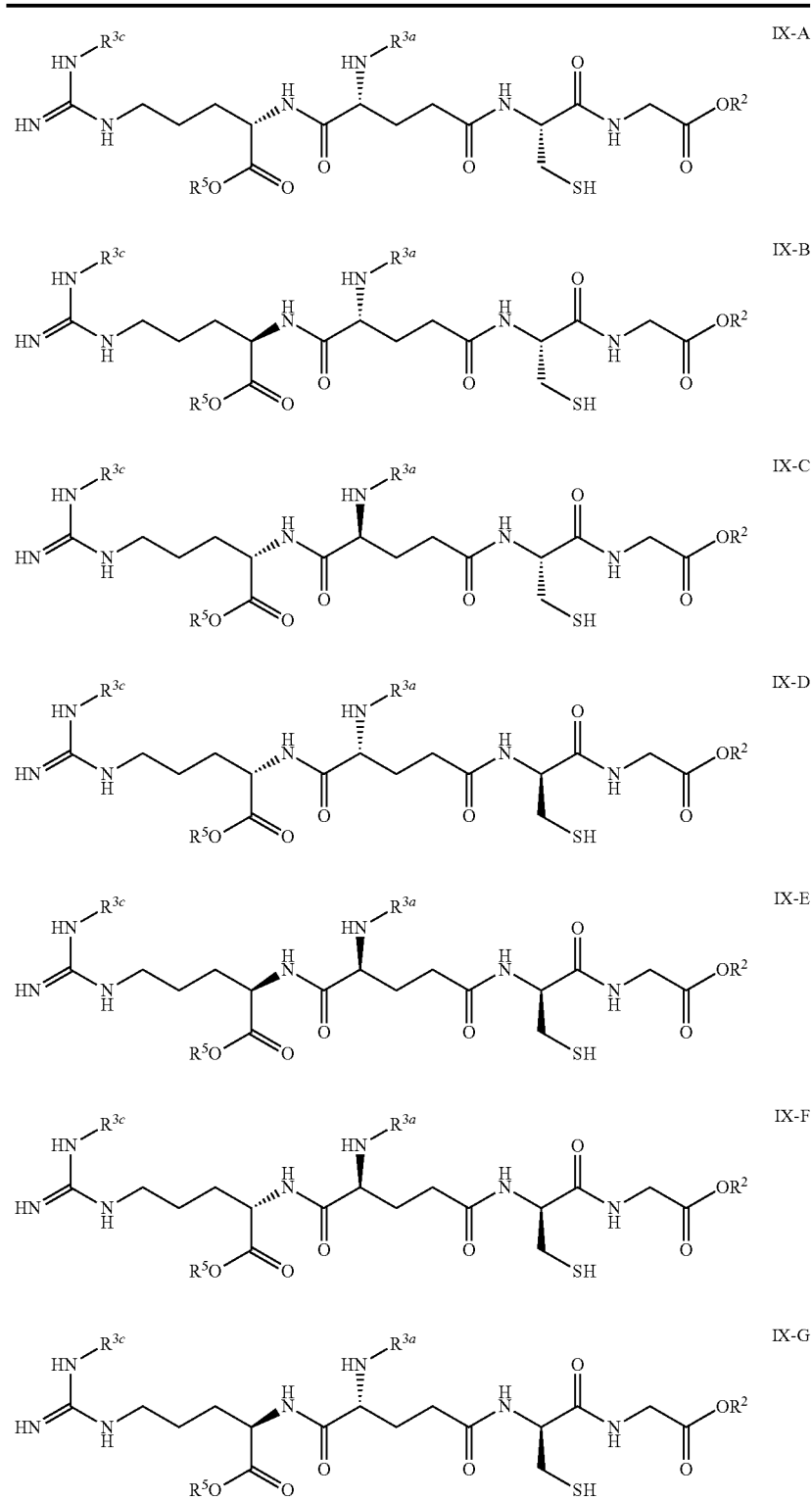

TABLE 8-continued

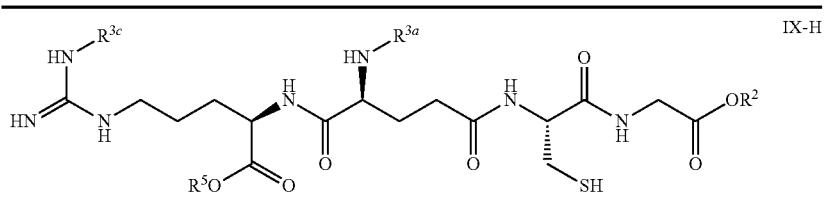

IX-H

In another embodiment, a Conjugate Compound of the Disclosure is a compound having Formula IX-A, and the pharmaceutically acceptable salts and solvates thereof. In another embodiment, a Conjugate Compound of the Disclosure is a compound having Formula IX-B, and the pharmaceutically acceptable salts and solvates thereof. In another embodiment, a Conjugate Compound of the Disclosure is a compound having Formula IX-C, and the pharmaceutically acceptable salts and solvates thereof. In another embodiment, a Conjugate Compound of the Disclosure is a compound having Formula IX-D, and the pharmaceutically acceptable salts and solvates thereof. In another embodiment, a Conjugate Compound of the Disclosure is a compound having Formula IX-E, and the pharmaceutically acceptable salts and solvates thereof. In another embodiment, a Conjugate Compound of the Disclosure is a compound having Formula IX-F, and the pharmaceutically acceptable salts and solvates thereof. In another embodiment, a Conjugate Compound of the Disclosure is a compound having Formula IX-G, and the pharmaceutically acceptable salts and solvates thereof. In another embodiment, a Conjugate Compound of the Disclosure is a compound having Formula IX-H, and the pharmaceutically acceptable salts and solvates thereof.

In another embodiment, a Conjugate Compound of the Disclosure is a compound having any one or more of Formulae I, VIII, VIII-A, VIII-B, VIII-C, VIII-D, VIII-E, VIII-F, VIII-G, VIII-H, IX, IX-A, IX-B, IX-C, IX-D, IX-E, IX-F, IX-G, or IX-H, wherein $R^2$ is hydrogen, and $R^{3a}$, $R^{3c}$, and $R^5$ are as defined in connection with Formula I. In another embodiment, $R^5$ is hydrogen.

In another embodiment, a Conjugate Compound of the Disclosure is a compound having any one or more of Formulae I, VIII, VIII-A, VIII-B, VIII-C, VIII-D, VIII-E, VIII-F, VIII-G, VIII-H, IX, IX-A, IX-B, IX-C, IX-D, IX-E, IX-F, IX-G, or IX-H, wherein $R^5$ is hydrogen, and $R^{3a}$, $R^{3c}$, and $R^2$ are as defined in connection with Formula I. In another embodiment, $R^2$ is hydrogen In another embodiment, a Conjugate Compound of the Disclosure is a compound having any one or more of Formulae I, VIII, VIII-A, VIII-B, VIII-C, VIII-D, VIII-E, VIII-F, VIII-G, VIII-H, IX, IX-A, IX-B, IX-C, IX-D, IX-E, IX-F, IX-G, or IX-H, wherein $R^2$ and $R^5$ are each hydrogen, and $R^{3a}$ and $R^{3c}$ are as defined in connection with Formula I. In another embodiment, $R^{3a}$ and $R^{3c}$ are each independently selected from the group consisting of hydrogen, BOC, FMOC, and CBZ. In another embodiment, $R^{3a}$ and $R^{3c}$ are each hydrogen.

In another embodiment, a Conjugate Compound of the Disclosure is a compound having Formula X:

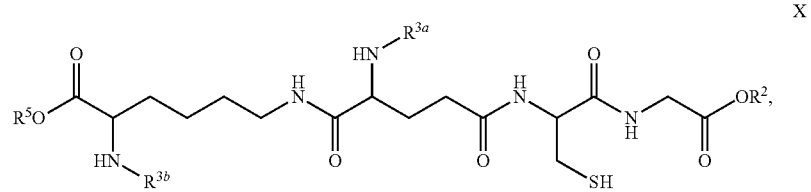

X and the pharmaceutically acceptable salts and solvates thereof, wherein $R^2$, $R^{3a}$, $R^{3b}$, and $R^5$ are as defined in connection with Formula I.

In another embodiment, a Conjugate Compound of the Disclosure is an enantiomerically enriched compound having any one or more of the formulae of Table 9, and the pharmaceutically acceptable salts and solvates thereof, wherein $R^2$, $R^{3a}$, $R^{3b}$, and $R^5$ are as defined in connection with Formula I.

TABLE 9

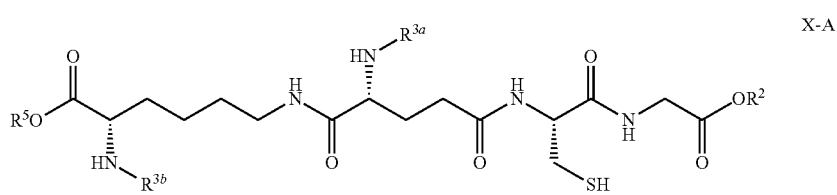

X-A

TABLE 9-continued

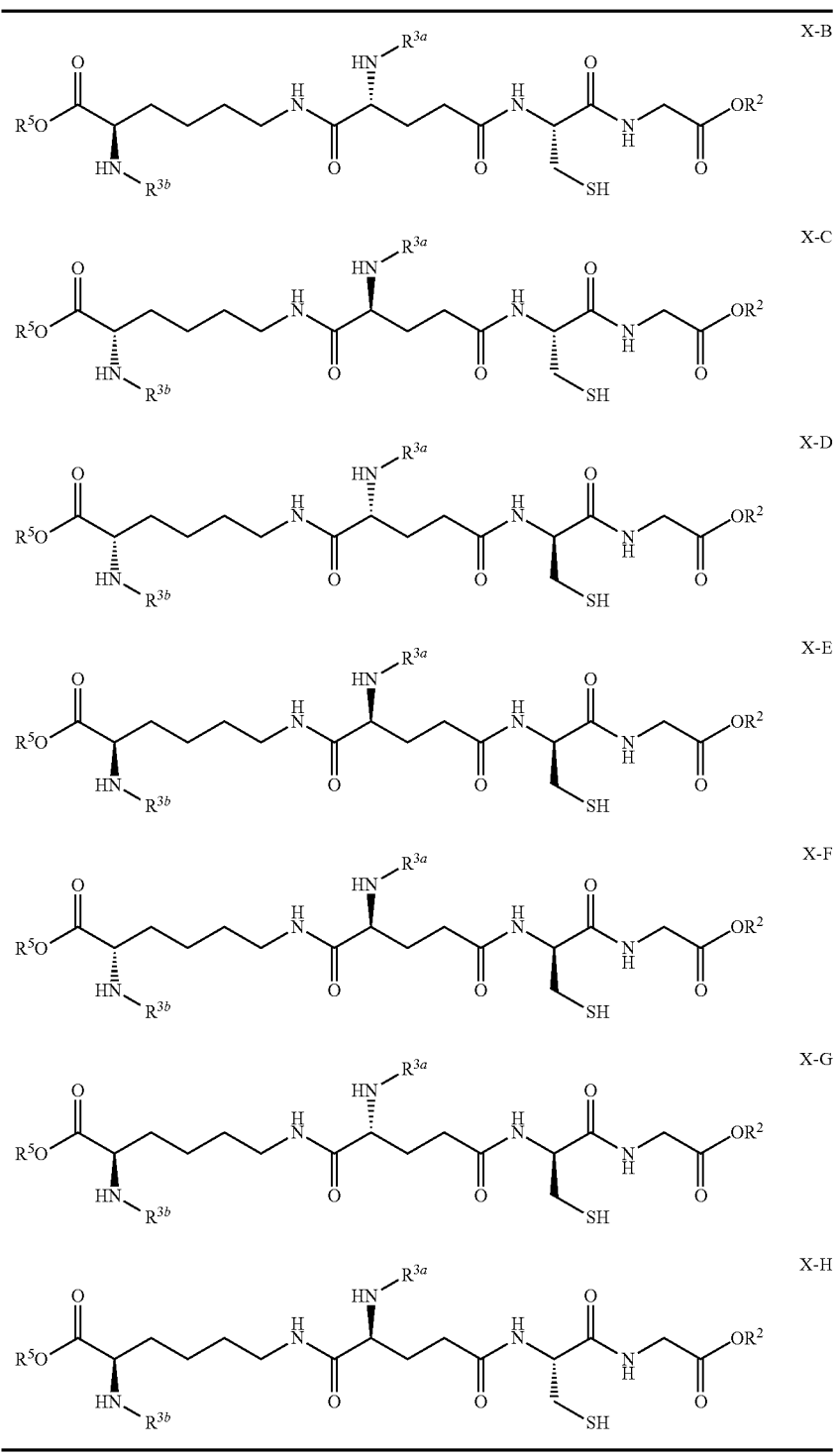

In another embodiment, a Conjugate Compound of the Disclosure is a compound having Formula X-A, and the pharmaceutically acceptable salts and solvates thereof. In another embodiment, a Conjugate Compound of the Disclosure is a compound having Formula X-B, and the pharmaceutically acceptable salts and solvates thereof. In another embodiment, a Conjugate Compound of the Disclosure is a compound having Formula X-C, and the pharmaceutically acceptable salts and solvates thereof. In another embodiment, a Conjugate Compound of the Disclosure is a compound having Formula X-D, and the pharmaceutically acceptable salts and solvates thereof. In another embodiment, a Conjugate Compound of the Disclosure is a compound having Formula X-E, and the pharmaceutically acceptable salts and solvates thereof. In another embodiment, a Conjugate Compound of the Disclosure is a compound having Formula X-F, and the pharmaceutically acceptable salts and solvates thereof. In another embodiment, a Conjugate Compound of the Disclosure is a compound having Formula X-G, and the pharmaceutically acceptable salts and solvates thereof. In another embodiment, a Conjugate Compound of the Disclosure is a compound having Formula X-H, and the pharmaceutically acceptable salts and solvates thereof.

In another embodiment, a Conjugate Compound of the Disclosure is a compound having any one or more of Formulae I, X, X-A, X-B, X-C, X-D, X-E, X-F, X-G, or X-H, wherein $R^2$ is hydrogen, and $R^{3a}$, $R^{3b}$, and $R^5$ are as defined in connection with Formula I. In another embodiment, $R^5$ is hydrogen.

In another embodiment, a Conjugate Compound of the Disclosure is a compound having any one or more of Formulae I, X, X-A, X-B, X-C, X-D, X-E, X-F, X-G, or X-H, wherein $R^5$ is hydrogen, and $R^{3a}$, $R^{3b}$, and $R^2$ are as defined in connection with Formula I. In another embodiment, $R^2$ is hydrogen.

In another embodiment, a Conjugate Compound of the Disclosure is a compound having any one or more of Formulae I, X, X-A, X-B, X-C, X-D, X-E, X-F, X-G, or X-H, wherein $R^2$ and $R^5$ are each hydrogen, and $R^{3a}$ and $R^{3b}$ are as defined in connection with Formula I. In another embodiment, $R^{3a}$ and $R^{3b}$ are each independently selected from the group consisting of hydrogen, BOC, FMOC, and CBZ. In another embodiment, $R^{3a}$ and $R^{3b}$ are each hydrogen.

In another embodiment, a Conjugate Compound of the Disclosure is a compound having Formula XI:

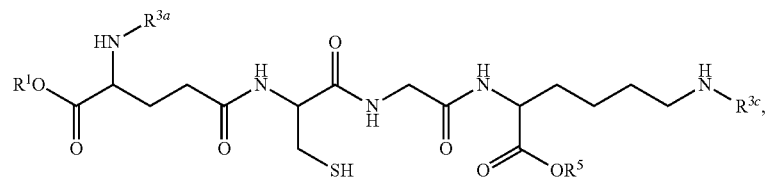

XI and the pharmaceutically acceptable salts and solvates thereof, wherein $R^1$, $R^{3a}$, $R^{3c}$, and $R^5$ are as defined in connection with Formula I.

In another embodiment, a Conjugate Compound of the Disclosure is an enantiomerically enriched compound having any one or more of the formula of Table 10, and the pharmaceutically acceptable salts and solvates thereof, wherein $R^1$, $R^{3a}$, $R^{3c}$, and $R^5$ are as defined in connection with Formula I.

TABLE 10

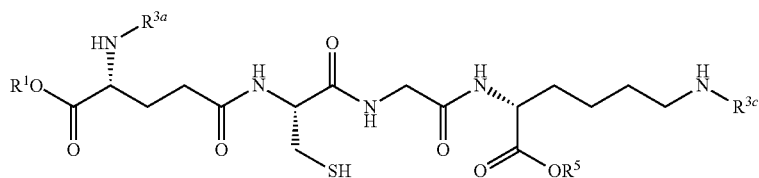

XI-A

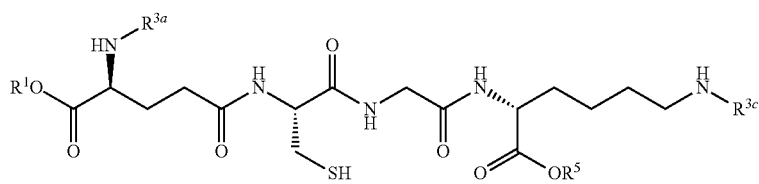

XI-B

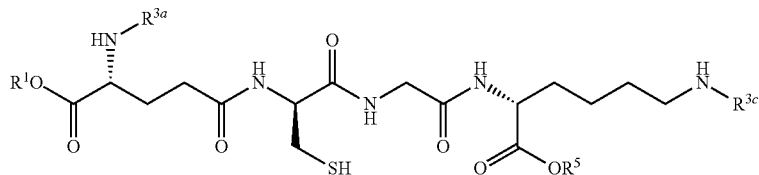

XI-C

TABLE 10-continued

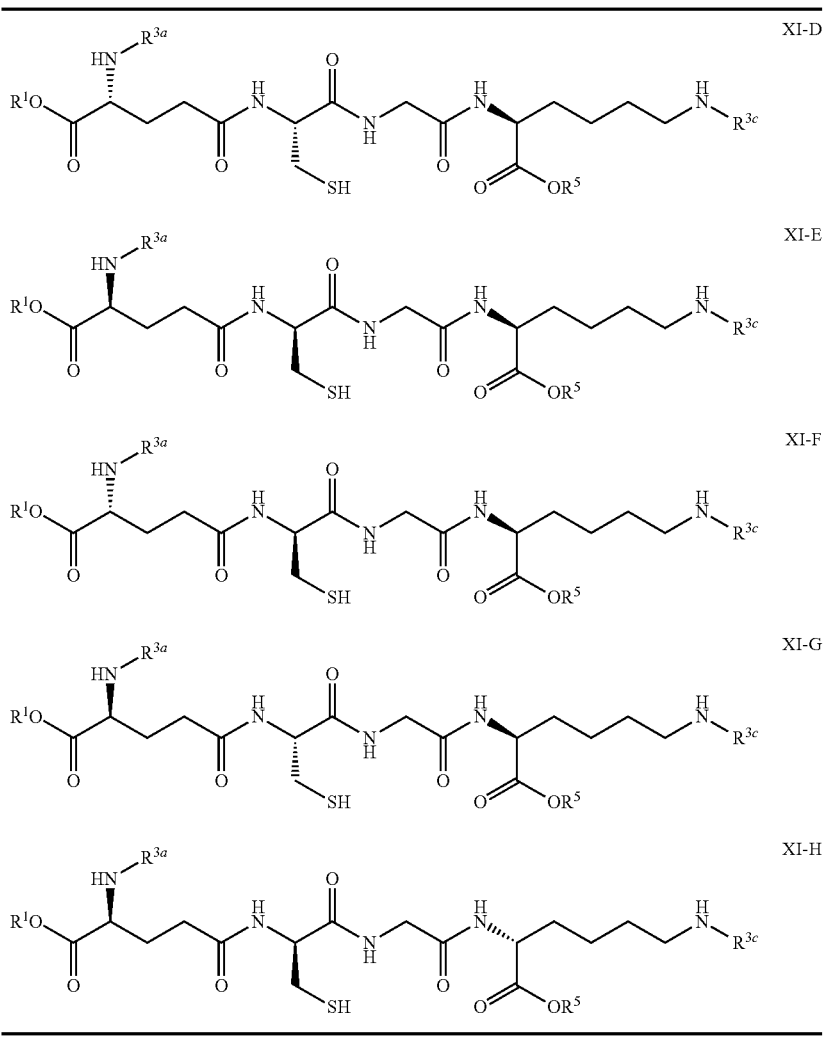

In another embodiment, a Conjugate Compound of the Disclosure is a compound having Formula XI-A, and the pharmaceutically acceptable salts and solvates thereof. In another embodiment, a Conjugate Compound of the Disclosure is a compound having Formula XI-B, and the pharmaceutically acceptable salts and solvates thereof. In another embodiment, a Conjugate Compound of the Disclosure is a compound having Formula XI-C, and the pharmaceutically acceptable salts and solvates thereof. In another embodiment, a Conjugate Compound of the Disclosure is a compound having Formula XI-D, and the pharmaceutically acceptable salts and solvates thereof. In another embodiment, a Conjugate Compound of the Disclosure is a compound having Formula XI-E, and the pharmaceutically acceptable salts and solvates thereof. In another embodiment, a Conjugate Compound of the Disclosure is a compound having Formula XI-F, and the pharmaceutically acceptable salts and solvates thereof. In another embodiment, a Conjugate Compound of the Disclosure is a compound having Formula XI-G, and the pharmaceutically acceptable salts and solvates thereof. In another embodiment, a Conjugate Compound of the Disclosure is a compound having Formula XI-H, and the pharmaceutically acceptable salts and solvates thereof.

In another embodiment, a Conjugate Compound of the Disclosure is a compound having Formula XII:

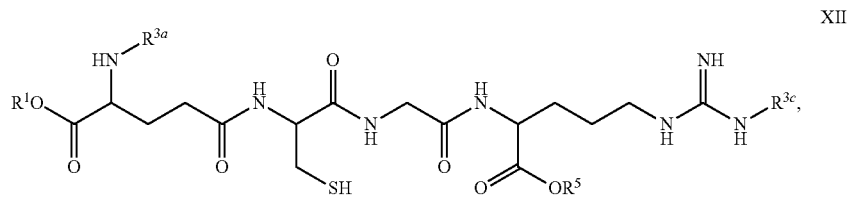

and the pharmaceutically acceptable salts and solvates thereof, wherein $R^1$, $R^{3a}$, $R^{3c}$, and $R^5$ are as defined in connection with Formula I.

In another embodiment, a Conjugate Compound of the Disclosure is an enantiomerically enriched compound having any one or more of the formulae of Table 11, and the pharmaceutically acceptable salts and solvates thereof, wherein $R^1$, $R^{3a}$, $R^{3c}$, and $R^5$ are as defined in connection with Formula I.

TABLE 11

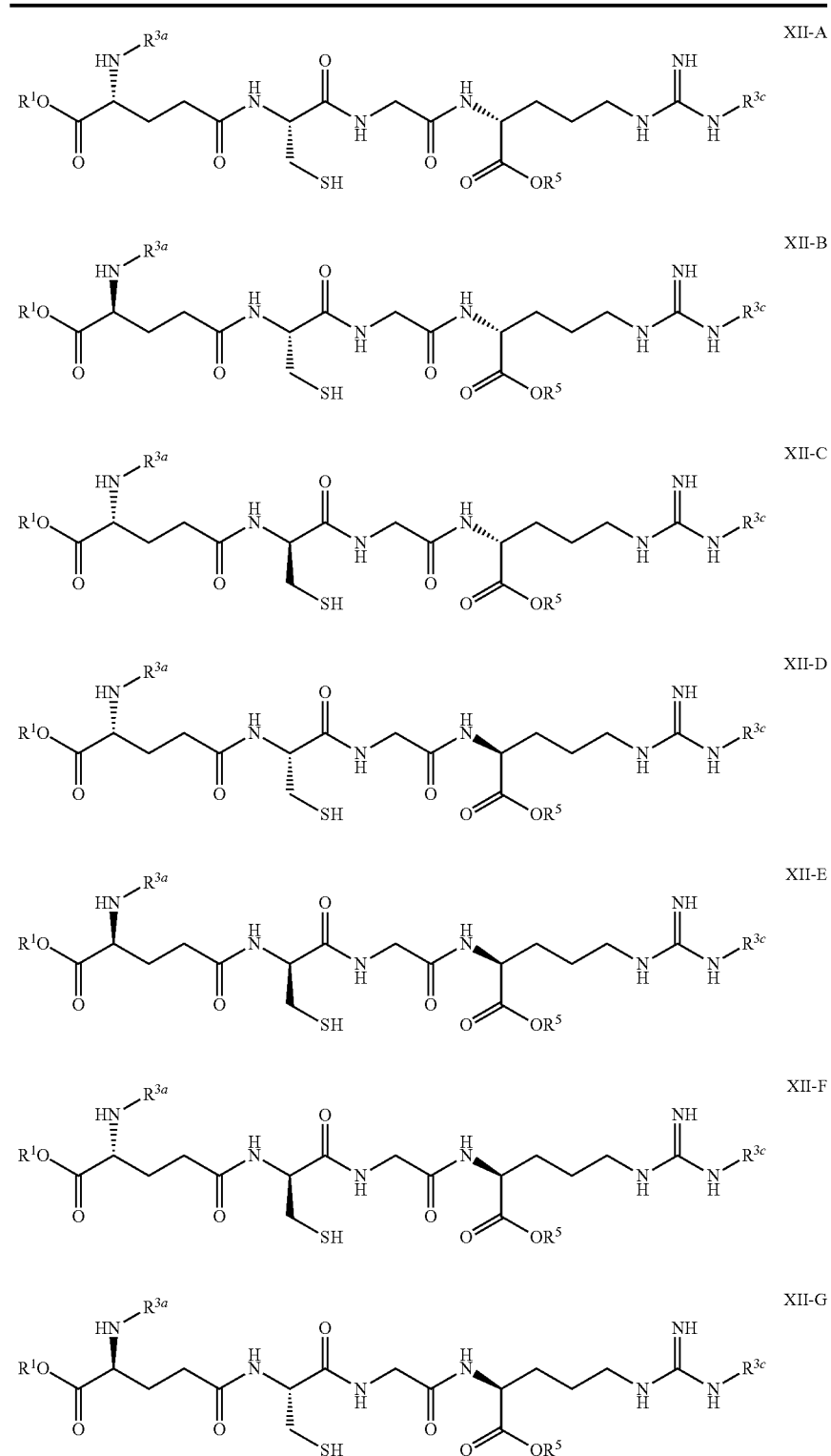

TABLE 11-continued

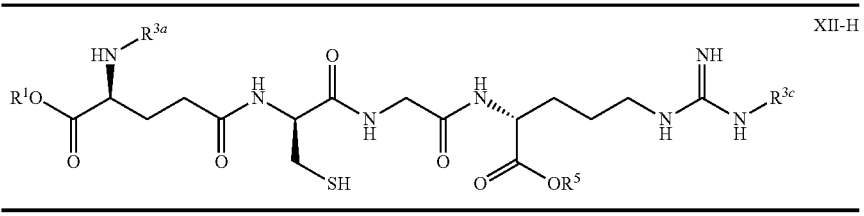

XII-H

In another embodiment, a Conjugate Compound of the Disclosure is a compound having Formula XII-A, and the pharmaceutically acceptable salts and solvates thereof. In another embodiment, a Conjugate Compound of the Disclosure is a compound having Formula XII-B, and the pharmaceutically acceptable salts and solvates thereof. In another embodiment, a Conjugate Compound of the Disclosure is a compound having Formula XII-C, and the pharmaceutically acceptable salts and solvates thereof. In another embodiment, a Conjugate Compound of the Disclosure is a compound having Formula XII-D, and the pharmaceutically acceptable salts and solvates thereof. In another embodiment, a Conjugate Compound of the Disclosure is a compound having Formula XII-E, and the pharmaceutically acceptable salts and solvates thereof. In another embodiment, a Conjugate Compound of the Disclosure is a compound having Formula XII-F, and the pharmaceutically acceptable salts and solvates thereof. In another embodiment, a Conjugate Compound of the Disclosure is a compound having Formula XII-G, and the pharmaceutically acceptable salts and solvates thereof. In another embodiment, a Conjugate Compound of the Disclosure is a compound having Formula XII-H, and the pharmaceutically acceptable salts and solvates thereof.

In another embodiment, a Conjugate Compound of the Disclosure is a compound having any one or more of Formulae I, XI, XI-A, XI-B, XI-C, XI-D, XI-E, XI-F, XI-G, XI-H, XII, XII-A, XII-B, XII-C, XII-D, XII-E, XII-F, XII-G, or XII-H, wherein $R^1$ is hydrogen, and $R^{3a}$, $R^{3c}$, and $R^5$ are as defined in connection with Formula I. In another embodiment, $R^5$ is hydrogen.

In another embodiment, a Conjugate Compound of the Disclosure is a compound having any one or more of Formulae I, XI, XI-A, XI-B, XI-C, XI-D, XI-E, XI-F, XI-G, XI-H, XII, XII-A, XII-B, XII-C, XII-D, XII-E, XII-F, XII-G, or XII-H, wherein $R^5$ is hydrogen, and $R^{3a}$, $R^{3c}$, and $R^1$ are as defined in connection with Formula I. In another embodiment, $R^1$ is hydrogen.

In another embodiment, a Conjugate Compound of the Disclosure is a compound having any one or more of Formulae I, XI, XI-A, XI-B, XI-C, XI-D, XI-E, XI-F, XI-G, XI-H, XII, XII-A, XII-B, XII-C, XII-D, XII-E, XII-F, XII-G, or XII-H, wherein $R^1$ and $R^5$ are each hydrogen, and $R^{3a}$ and $R^{3c}$ are as defined in connection with Formula I. In another embodiment, $R^{3a}$ and $R^{3b}$ are each independently selected from the group consisting of hydrogen, BOC, FMOC, and CBZ. In another embodiment, $R^{3a}$ and $R^{3c}$ are each hydrogen.

In another embodiment, a Conjugate Compound of the Disclosure is a compound having Formula XIII:

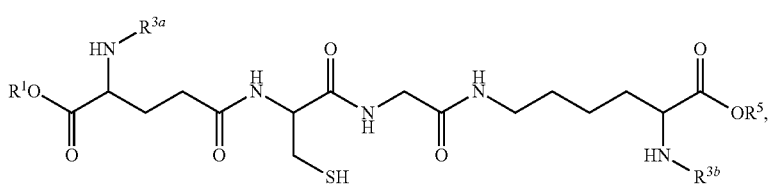

XIII and the pharmaceutically acceptable salts and solvates thereof, wherein $R^1$, $R^{3a}$, $R^{3b}$, and $R^5$ are as defined in connection with Formula I.

In another embodiment, a Conjugate Compound of the Disclosure is an enantiomerically enriched compound having any one or more of the formulae of Table 12, and the pharmaceutically acceptable salts and solvates thereof, wherein $R^1$, $R^{3a}$, $R^{3b}$, and $R^5$ are as defined in connection with Formula I.

TABLE 12

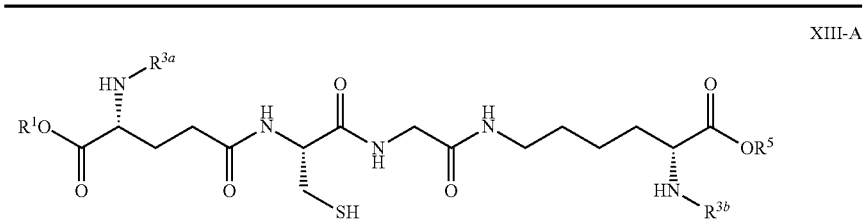

XIII-A

TABLE 12-continued

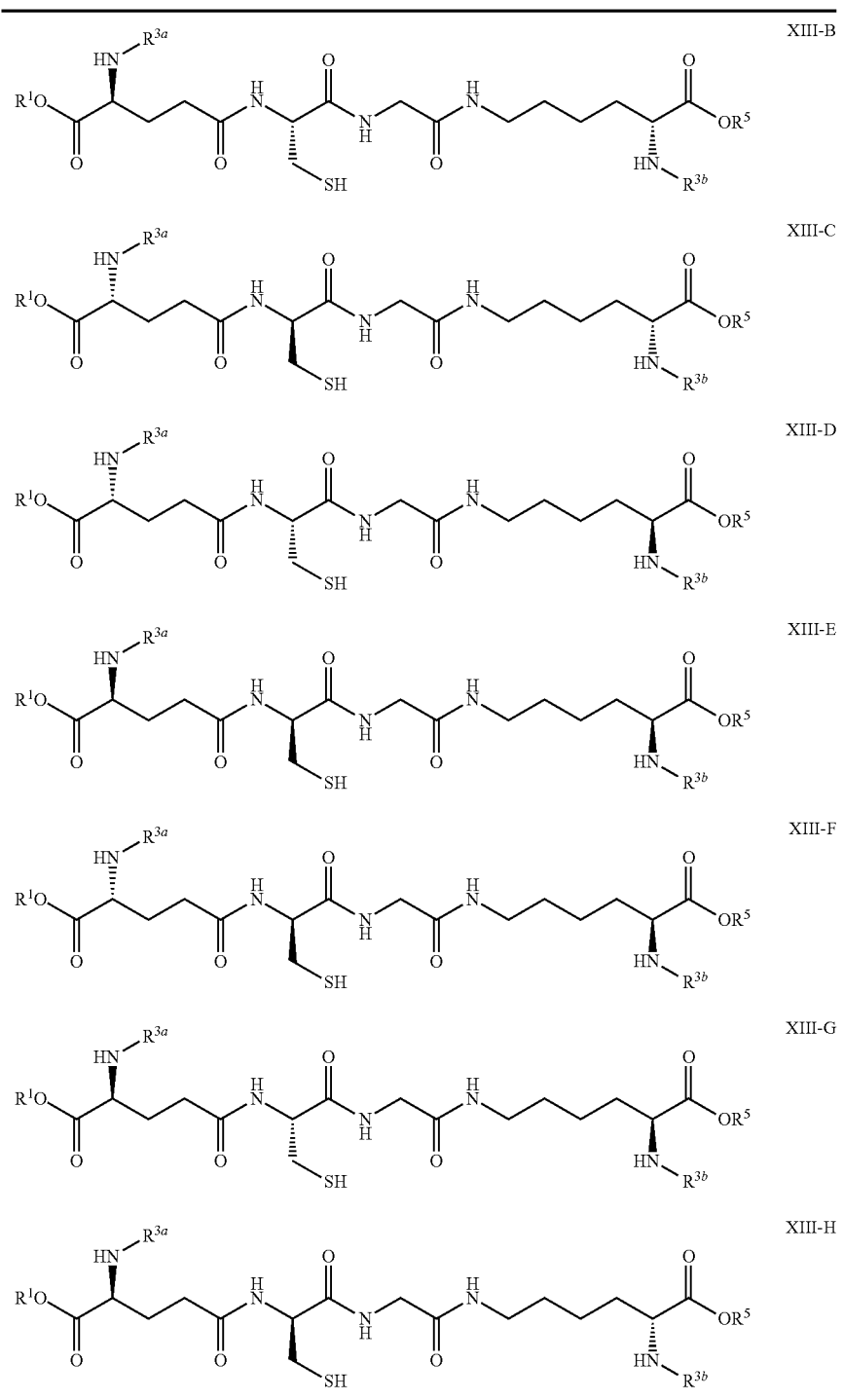

In another embodiment, a Conjugate Compound of the Disclosure is a compound having Formula XIII-A, and the pharmaceutically acceptable salts and solvates thereof. In another embodiment, a Conjugate Compound of the Disclosure is a compound having Formula XIII-B, and the pharmaceutically acceptable salts and solvates thereof. In another embodiment, a Conjugate Compound of the Disclosure is a compound having Formula XIII-C, and the pharmaceutically acceptable salts and solvates thereof. In another embodiment, a Conjugate Compound of the Disclosure is a compound having Formula XIII-D, and the pharmaceutically acceptable salts and solvates thereof. In another embodiment, a Conjugate Compound of the Disclosure is a compound having Formula XIII-E, and the pharmaceutically acceptable salts and solvates thereof. In another embodiment, a Conjugate Compound of the Disclosure is a compound having Formula XIII-F, and the pharmaceutically acceptable salts and solvates thereof. In another embodiment, a Conjugate Compound of the Disclosure is a compound having Formula XIII-G, and the pharmaceutically acceptable salts and solvates thereof. In another embodiment, a Conjugate Compound of the Disclosure is a compound having Formula XIII-H, and the pharmaceutically acceptable salts and solvates thereof.

In another embodiment, a Conjugate Compound of the Disclosure is a compound having any one or more of Formulae I, XIII, XIII-A, XIII-B, XIII-C, XIII-D, XIII-E, XIII-F, XIII-G, or XIII-H, wherein $R^1$ is hydrogen, and $R^{3a}$, $R^{3b}$, and $R^5$ are as defined in connection with Formula I. In another embodiment, $R^5$ is hydrogen.

In another embodiment, a Conjugate Compound of the Disclosure is a compound having any one or more of Formulae I, XIII, XIII-A, XIII-B, XIII-C, XIII-D, XIII-E, XIII-F, XIII-G, or XIII-H, wherein $R^5$ is hydrogen, and $R^{3a}$, $R^{3b}$, and $R^1$ are as defined in connection with Formula I. In another embodiment, $R^1$ is hydrogen.

In another embodiment, a Conjugate Compound of the Disclosure is a compound having any one or more of Formulae I, XIII, XIII-A, XIII-B, XIII-C, XIII-D, XIII-E, XIII-F, XIII-G, or XIII-H, wherein $R^1$ and $R^5$ are each hydrogen, and $R^{3a}$ and $R^{3b}$ are as defined in connection with Formula I. In another embodiment, $R^{3a}$ and $R^{3b}$ are each independently selected from the group consisting of hydrogen, BOC, FMOC, and CBZ. In another embodiment, $R^{3a}$ and $R^{3b}$ are each hydrogen.

In another embodiment, a Conjugate Compound of the Disclosure is a compound having Formula XIV:

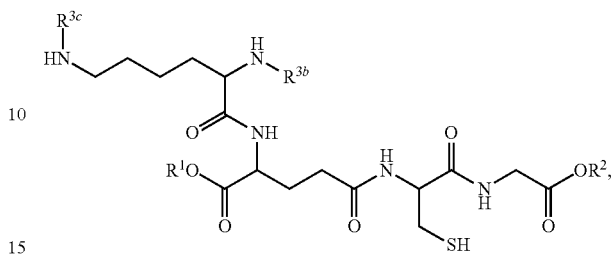

and the pharmaceutically acceptable salts and solvates thereof, wherein $R^1$, $R^2$, $R^{3b}$, and $R^{3c}$ are as defined in connection with Formula I.

In another embodiment, a Conjugate Compound of the Disclosure is an enantiomerically enriched compound having any one or more of the formulae of Table 13, and the pharmaceutically acceptable salts and solvates thereof, wherein $R^1$, $R^2$, $R^{3b}$, and $R^{3c}$ are as defined in connection with Formula I.

TABLE 13

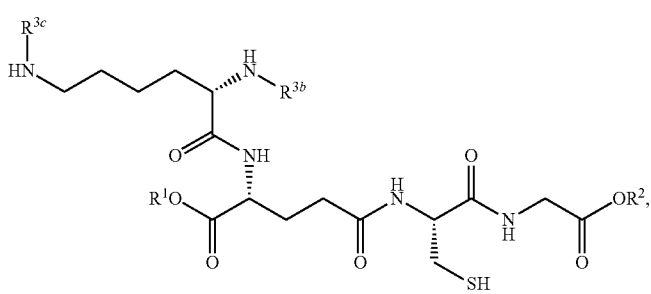

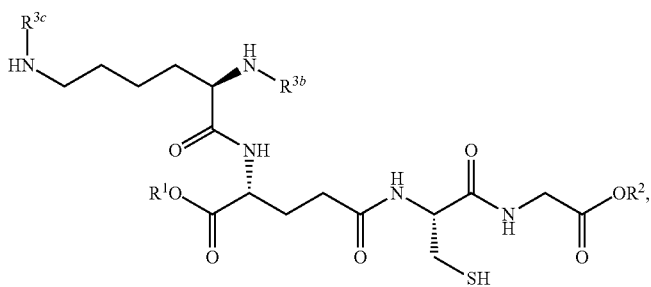

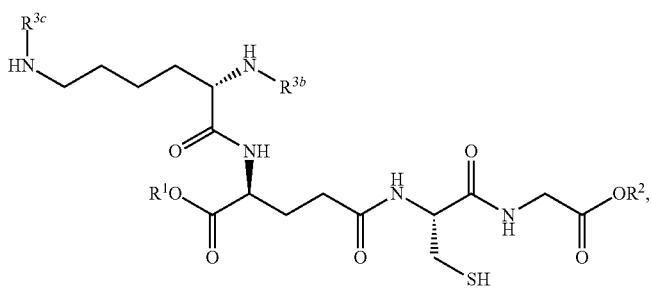

TABLE 13-continued
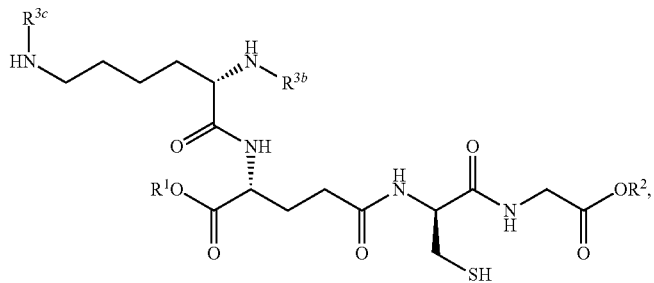
XIV-D
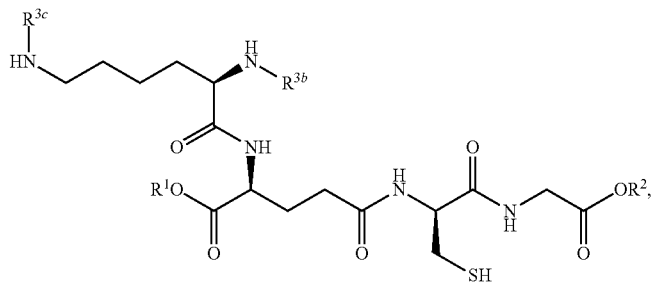
XIV-E
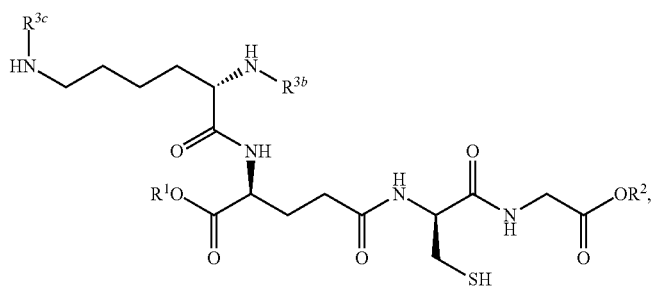
XIV-F
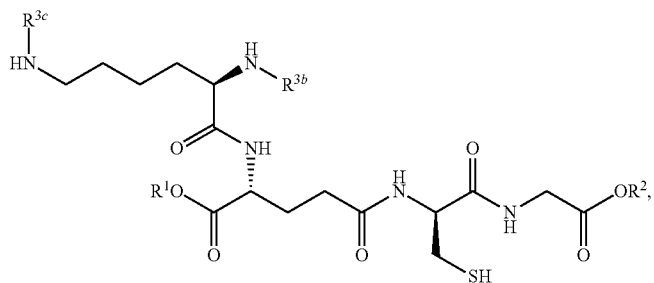
XIV-G
or
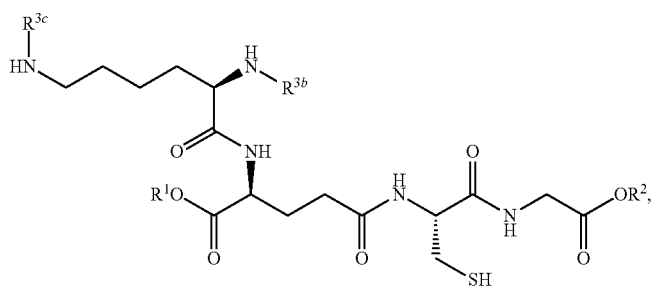
XIV-H In another embodiment, a Conjugate Compound of the Disclosure is a compound having Formula XIV-A, and the pharmaceutically acceptable salts and solvates thereof. In another embodiment, a Conjugate Compound of the Disclosure is a compound having Formula XIV-B, and the pharmaceutically acceptable salts and solvates thereof. In another embodiment, a Conjugate Compound of the Disclosure is a compound having Formula XIV-C, and the pharmaceutically acceptable salts and solvates thereof. In another embodiment, a Conjugate Compound of the Disclosure is a compound having Formula XIV-D, and the pharmaceutically acceptable salts and solvates thereof. In another embodiment, a Conjugate Compound of the Disclosure is a compound having Formula XIV-E, and the pharmaceutically acceptable salts and solvates thereof. In another embodiment, a Conjugate Compound of the Disclosure is a compound having Formula XIV-F, and the pharmaceutically acceptable salts and solvates thereof. In another embodiment, a Conjugate Compound of the Disclosure is a compound having Formula XIV-G, and the pharmaceutically acceptable salts and solvates thereof. In another embodiment, a Conjugate Compound of the Disclosure is a compound having Formula XIV-H, and the pharmaceutically acceptable salts and solvates thereof.

In another embodiment, a Conjugate Compound of the Disclosure is a compound having Formula XV:

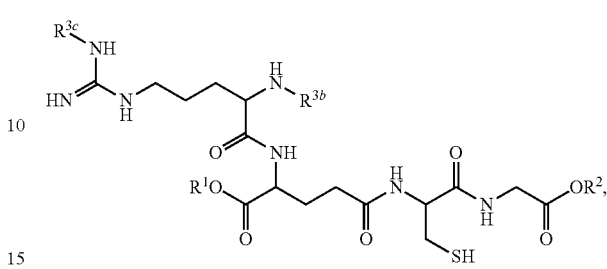

XV and the pharmaceutically acceptable salts and solvates thereof, wherein $R^1$, $R^2$, $R^{3b}$, and $R^{3c}$ are as defined in connection with Formula I.

In another embodiment, a Conjugate Compound of the Disclosure is an enantiomerically enriched compound having any one or more of the formulae of Table 14, and the pharmaceutically acceptable salts and solvates thereof, wherein $R^1$, $R^2$, $R^{3b}$, and $R^{3c}$ are as defined in connection with Formula I.

TABLE 14

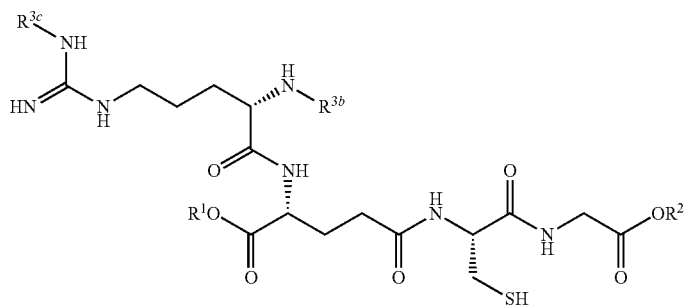

IV-A

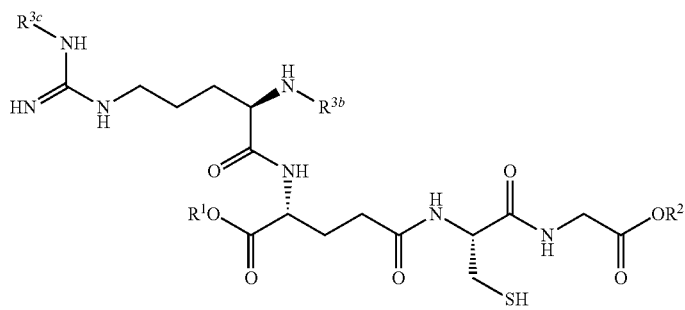

XV-B

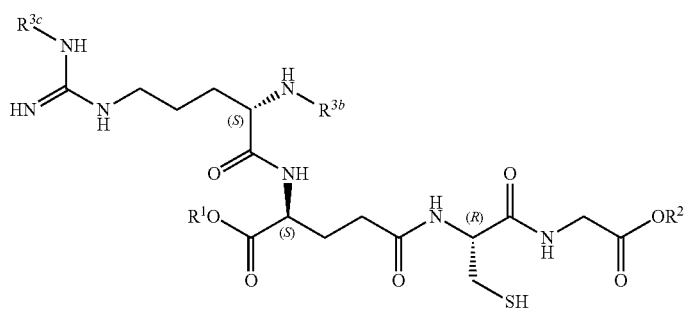

XV-C

TABLE 14-continued
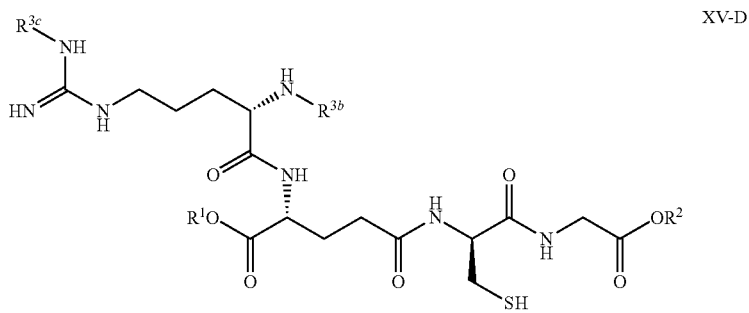
XV-D
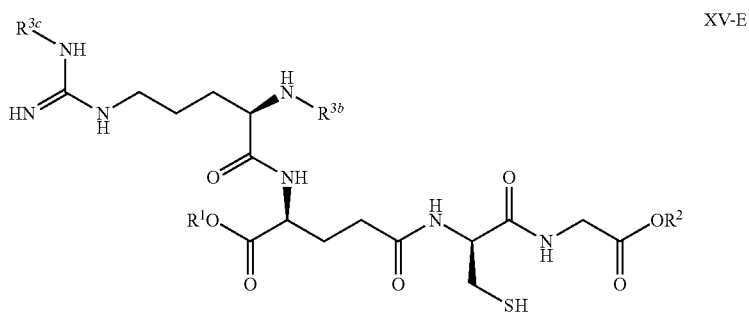
XV-E
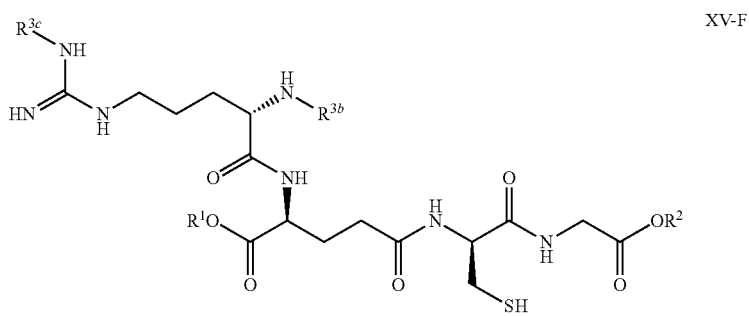
XV-F
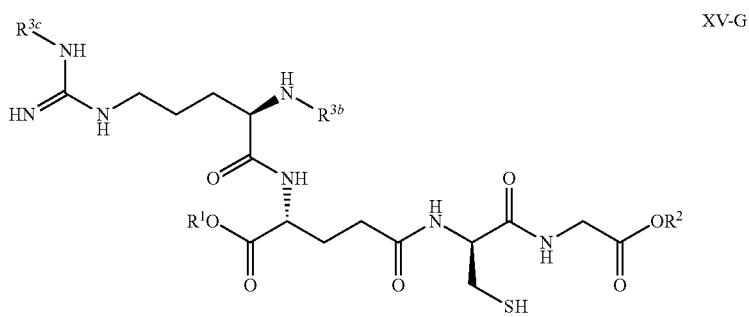
XV-G
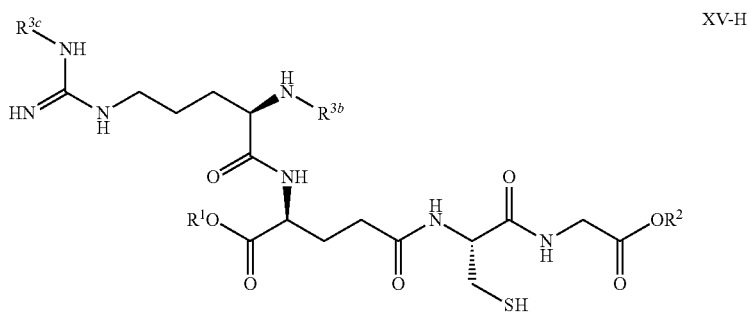
XV-H In another embodiment, a Conjugate Compound of the Disclosure is a compound having Formula XV-A, and the pharmaceutically acceptable salts and solvates thereof. In another embodiment, a Conjugate Compound of the Disclosure is a compound having Formula XV-B, and the pharmaceutically acceptable salts and solvates thereof. In another embodiment, a Conjugate Compound of the Disclosure is a compound having Formula XV-C, and the pharmaceutically acceptable salts and solvates thereof. In another embodiment, a Conjugate Compound of the Disclosure is a compound having Formula XV-D, and the pharmaceutically acceptable salts and solvates thereof. In another embodiment, a Conjugate Compound of the Disclosure is a compound having Formula XV-E, and the pharmaceutically acceptable salts and solvates thereof. In another embodiment, a Conjugate Compound of the Disclosure is a compound having Formula XV-F, and the pharmaceutically acceptable salts and solvates thereof. In another embodiment, a Conjugate Compound of the Disclosure is a compound having Formula XV-G, and the pharmaceutically acceptable salts and solvates thereof. In another embodiment, a Conjugate Compound of the Disclosure is a compound having Formula XV-H, and the pharmaceutically acceptable salts and solvates thereof.

In another embodiment, a Conjugate Compound of the Disclosure is a compound having Formula XVI:

and the pharmaceutically acceptable salts and solvates thereof, wherein $R^{3a}$, $R^{3b}$, $R^{3c}$, and X are as defined in connection with Formula I.

In another embodiment, a Conjugate Compound of the Disclosure is a compound having Formulae XVI or XVI-A, and the pharmaceutically acceptable salts and solvates thereof, wherein $R^{3a}$, $R^{3b}$, and $R^{3c}$ are each hydrogen.

In another embodiment, a Conjugate Compound of the Disclosure is a compound having Formulae XVI or XVI-A, wherein X is —O(CH$_2$)$_m$O— and m is 2 or 3, and $R^{3a}$, $R^{3b}$, and $R^{3c}$ are each hydrogen.

In another embodiment, a Conjugate Compound of the Disclosure is a compound having any one or more of Formulae I, XIV, XIV-A, XIV-B, XIV-C, XIV-D, XIV-E, XIV-F, XIV-G, XIV-H, XV, XV-A, XV-B, XV-C, XV-D, XV-E, XV-F, XV-G, or XV-H, wherein $R^1$ is hydrogen, and $R^{3b}$, $R^{3c}$, and $R^2$ are as defined in connection with Formula I. In another embodiment, $R^2$ is hydrogen.

In another embodiment, a Conjugate Compound of the Disclosure is a compound having any one or more of Formulae I, XIV, XIV-A, XIV-B, XIV-C, XIV-D, XIV-E, XIV-F, XIV-G, XIV-H, XV, XV-A, XV-B, XV-C, XV-D, XV-E, XV-F, XV-G, or XV-H, wherein $R^2$ is hydrogen, and

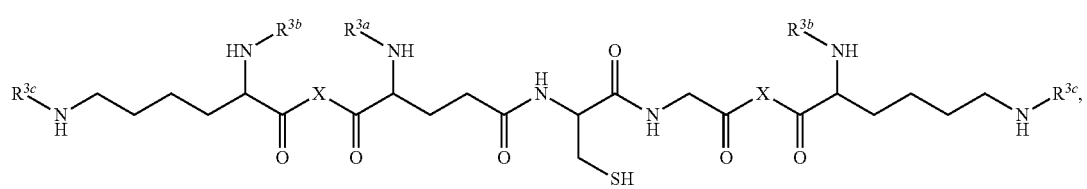

XVI or a pharmaceutically acceptable salt or solvate thereof, wherein $R^{3a}$, $R^{3b}$, $R^{3c}$, and X are as defined in connection with Formula I.

In another embodiment, a Conjugate Compound of the Disclosure is an enantiomerically enriched compound having Formula XVI-A:

$R^{3b}$, $R^{3c}$, and $R^1$ are as defined in connection with Formula I. In another embodiment, $R^1$ is hydrogen.

In another embodiment, a Conjugate Compound of the Disclosure is a compound having any one or more of Formulae I, XIV, XIV-A, XIV-B, XIV-C, XIV-D, XIV-E,

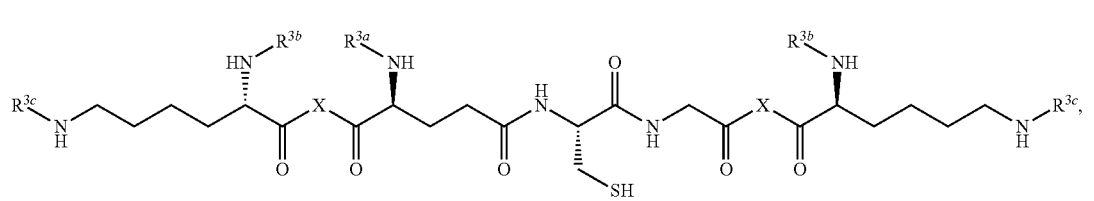

XVI-A

XIV-F, XIV-G, XIV-H, XV, XV-A, XV-B, XV-C, XV-D, XV-E, XV-F, XV-G, or XV-H, wherein $R^1$ and $R^2$ are each hydrogen, and $R^{3b}$ and $R^{3c}$ are as defined in connection with Formula I. In another embodiment, $R^{3b}$ and $R^{3b}$ are each independently selected from the group consisting of hydrogen, BOC, FMOC, and CBZ. In another embodiment, $R^{3b}$ and $R^{3c}$ are each hydrogen.

In another embodiment, Compounds of the Disclosure are compounds of Table 15, and the pharmaceutically acceptable salts and solvates thereof.

TABLE 15

| Cpd. No. | Structure |
|---|---|
| 1 | 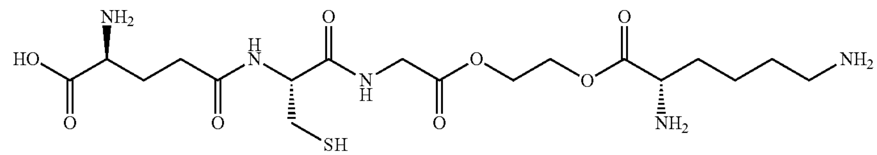 [SMILES: NCCCC[C@H](N)C(=O)OCCOC(=O)CNC(=O)[C@H](CS)NC(=O)CC[C@H](N)C(=O)O] |
| 2 | 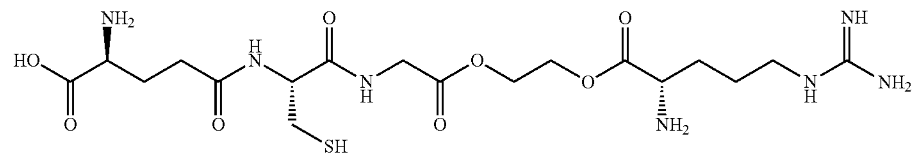 [SMILES: N=C(N)NCCC[C@H](N)C(=O)OCCOC(=O)CNC(=O)[C@H](CS)NC(=O)CC[C@H](N)C(=O)O] |
| 3 | 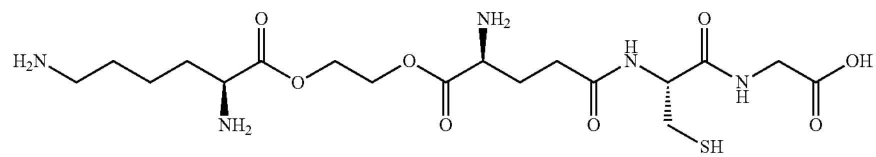 [SMILES: NCCCC[C@H](N)C(=O)OCCOC(=O)[C@@H](N)CCC(=O)N[C@@H](CS)C(=O)NCC(=O)O] |
| 4 | 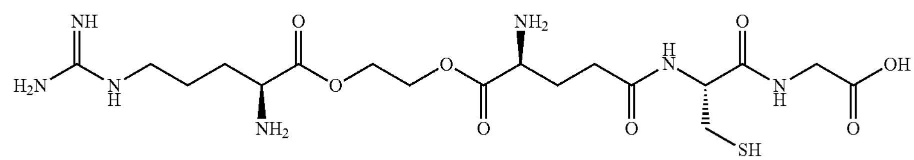 [SMILES: N=C(N)NCCC[C@H](N)C(=O)OCCOC(=O)[C@@H](N)CCC(=O)N[C@@H](CS)C(=O)NCC(=O)O] |
| 5 | 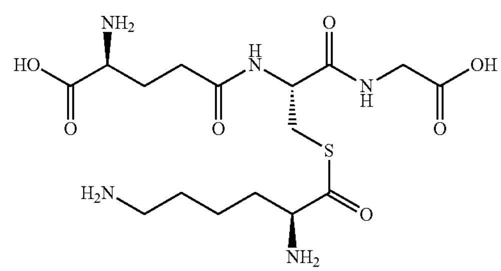 [SMILES: NCCCC[C@H](N)C(=O)SC[C@H](NC(=O)CC[C@H](N)C(=O)O)C(=O)NCC(=O)O] |
| 6 | 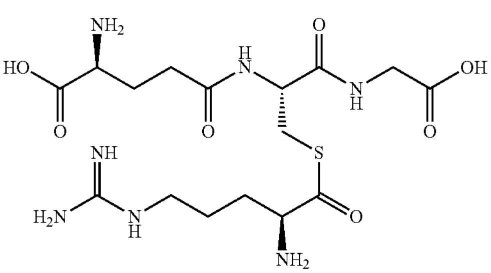 [SMILES: N=C(N)NCCC[C@H](N)C(=O)SC[C@H](NC(=O)CC[C@H](N)C(=O)O)C(=O)NCC(=O)O] |

TABLE 15-continued

| Cpd. No. | Structure |
|---|---|
| 7 | (chemical structure) |
| 8 | (chemical structure) |
| 9 | (chemical structure) |
| 10 | (chemical structure) |
| 11 | (chemical structure) |
| 12 | (chemical structure) |
| 13 | (chemical structure) |
| 14 | (chemical structure) |

TABLE 15-continued

| Cpd. No. | Structure |
|---|---|
| 15 | (chemical structure: symmetric compound with H$_2$N-lysine-O-CH$_2$CH$_2$-O-glutamate-cysteine(SH)-glycine-O-CH$_2$CH$_2$-O-lysine-NH$_2$) |

Compositions of the Disclosure

Glutathione, a glutathione derivative, a glutathione conjugate, a pharmaceutically-acceptable salt thereof, or any combination thereof can be admixed with a pharmaceutical carrier, e.g., water, and, optionally, other components to give a "Composition of the Disclosure." In some embodiments, the amount of glutathione, a glutathione derivative, a glutathione conjugate, pharmaceutically-acceptable salt thereof, or any combination thereof, e.g., reduced glutathione, in the Composition of the Disclosure is about 30-90% by weight, about 30-85% by weight, about 30-80% by weight, about 30-75% by weight, about 30-70% by weight, about 30-65% by weight, about 30-60% by weight, about 30-55% by weight, about 30-50% by weight. In some embodiments, the amount of glutathione, a glutathione derivative, a glutathione conjugate, pharmaceutically-acceptable salt thereof, or any combination thereof, e.g., reduced glutathione, in the Composition of the Disclosure is 30-50% by weight.

In some embodiments, the Composition of the Disclosure further comprises an organic acid. In some embodiments, the organic acid is selected from the group of acids consisting of ascorbic, acetic, adipic, aspartic, benzenesulfonic, benzoic, butyric, camphorsulfonic, camsylic, carbonic, chlorobenzoic, cholic, citric, edetic, edisylic, estolic, ethanesulfonic, formic, fumaric, gluceptic, gluconic, glucuronic, glutamic, glycolic, glycolylarsanilic, hippuric, 1-hydroxy-2-naphthoic, isethionic, isobutyric, isonicotinic, lactic, lactobionic, maleic, malic, malonic, mandelic, methanesulfonic, mucic, muconic, napthalenesulfonic, nicotinic, oxalic, oleic, orotic, p-nitromethanesulfonic, pamoic, pantothenic, phthalic, polygalacturonic, propionic, saccharic, salicylic, stearic, suberic, succinic, sulfanilic, tannic, tartaric, p-toluenesulfonic and any combination thereof. In some embodiments, the amount of organic acid, e.g., reduced ascorbic acid, in the Composition of the Disclosure is about 10-90% by weight, about 10-85% by weight, about 10-80% by weight, about 10-75% by weight, about 10-70% by weight, about 10-65% by weight, about 10-60% by weight, about 10-55% by weight, about 10-50% by weight, about 10-45% by weight, about 10-40% by weight, about 10-35% by weight, about 10-30% by weight, about 1-30% by weight, about 1-20% by weight, or about 1-10% by weight. In some embodiments, the amount of organic acid, e.g., reduced ascorbic acid, in the Composition of the Disclosure is 25-40% by weight.

In some embodiments, the Composition of the Disclosure further comprises a bicarbonate salt. In some embodiments, the bicarbonate salt is sodium bicarbonate. In some embodiments, the amount of bicarbonate salt, e.g., sodium bicarbonate, in the Composition of the Disclosure is about 10-90% by weight, about 10-85% by weight, about 10-80% by weight, about 10-75% by weight, about 10-70% by weight, about 10-65% by weight, about 10-60% by weight, about 10-55% by weight, about 10-50% by weight, about 10-45% by weight, about 10-40% by weight, about 10-35% by weight, about 10-30% by weight, about 1-30% by weight, about 1-20% by weight, or about 1-10% by weight. In some embodiments, the amount of bicarbonate salt, e.g., sodium bicarbonate, in the Composition of the Disclosure is about 20-30% by weight.

In some embodiments, the pH of the Composition of the Disclosure is about 6.0 to about 8. In some embodiments, the pH of the Composition of the Disclosure is greater than 5.5 or at least 6.0. (e.g., 5.6 to 14, 5.7 to 14, 5.8 to 14, 5.9 to 14, 6 to 14, 5.6 to 12, 5.7 to 12, 5.8 to 12, 5.9 to 12, 6 to 12, 5.6 to 10, 5.7 to 10, 5.8 to 10, 5.9 to 10, 6 to 10, 5.6 to 9, 5.7 to 9, 5.8 to 9, 5.9 to 9, 6 to 9, 5.6 to 8, 5.7 to 8, 5.8 to 8, 5.9 to 8, 6 to 8, 5.6 to 7.5, 5.7 to 7.5, 5.8 to 7.5, 5.9 to 7.5, 6 to 7.5, 5.6 to 7, 5.7 to 7, 5.8 to 7, 5.9 to 7, or 6 to 7).

In some embodiments, the Composition of the Disclosure is formulated to maximize formulation stability and minimize oxidation of glutathione. Oxidized glutathione is associated with the generation of protein-carbonyls via glutathionlyation. Glutathionylation occurs when oxidized glutathione dissociates and attaches to proteins. Maintaining the glutathione in the reduced state in solution prior to administration can decrease the risk of glutathionylation products that can result in clinical complications such as bronchiectasis. In some embodiments, the oxidized glutathione (e.g., % GSSG) in the Composition of the Disclosure is less than about 20%, less than about 18%, less than about 16%, less than about 15%, less than about 12%, less than about 10%, less than about 9%, less than about 8%, less than about 7%, less than about 6%, less than about 5%, less than about 4%, or less than about 3% by weight of the total glutathione in the Composition of the Disclosure after storage of the Composition of the Disclosure for 4 weeks (e.g., at 5° C. in a N$_2$ atmosphere and/or ambient atmosphere). In some embodiments, the percentage of oxidized glutathione (e.g., % GSSG) in the Composition of the Disclosure is no more than about 2% to about 20%, about 2% to about 18%, about 2% to about 16%, about 2% to about 16%, about 2% to about 10%, or about 2% to 8% by weight of the total glutathione in the Composition of the Disclosure following 4 weeks of storage (e.g., at 5° C. in a N$_2$ atmosphere and/or ambient atmosphere). In some embodiments, the percentage of oxidized glutathione (e.g., % GSSG) in the Composition of the Disclosure is less than about 20%, less than about 18%, less than about 16%, or less than about 10% by weight of the total glutathione in the Composition of the Disclosure following 4 weeks of storage (e.g., at 5° C. in a N$_2$ atmosphere and/or ambient atmosphere).

In some embodiments, the reduced glutathione in the Composition of the Disclosure is more than about 80%, more than about 82%, more than about 84%, more than about 85%, more than about 88%, more than about 90%, more than about 91%, more than about 92%, more than about 93%, more than about 94%, more than about 95%, more than about 96%, or more than about 97% by weight of the total glutathione in the Composition of the Disclosure after storage of the Composition of the Disclosure for 4 weeks at about 5° C. (e.g., in a $N_2$ or ambient atmosphere). In some embodiments, the percentage of reduced glutathione in the Composition of the Disclosure is between about 80% to about 100%, between about 80% to about 98%, between about 82% to about 98%, between about 84% to about 98%, between about 86% to about 98%, between about 88% to about 98%, between about 90% to about 98%, or between about 92% to about 98% by weight of the total glutathione in the Composition of the Disclosure following 4 weeks of storage at 5° C. (e.g., in a $N_2$ or ambient atmosphere). In some embodiments, the percentage of reduced glutathione in the Composition of the Disclosure is at least 80%, at least 82%, at least 84%, at least 86%, at least 88%, or at least 90% by weight of the total glutathione in the Composition of the Disclosure following 4 weeks of storage at 5° C. in a $N_2$ or ambient atmosphere.

In some embodiments, the Composition of the Disclosure is further formulated to maximize formulation stability and minimize oxidation of organic acid, e.g., ascorbic acid. Additionally, when ascorbic acid is oxidized into dehydroascorbate (DHA), DHA can break down and result in the formation of protein adducts in process called ascorbylation. Maintaining the organic acid, e.g., ascorbic acid, in the reduced state in solution prior to administration can decrease the risk of ascorbylation from the breakdown products of dehydroascorbate. In some embodiments, the reduced ascorbic acid (e.g., % ASC) is more than about 80%, more than about 85%, more than about 86%, more than about 87%, more than about 88%, more than about 89%, or more than about 90% by weight of the ascorbic acid in the Composition of the Disclosure after storage of the Composition of the Disclosure for 4 weeks (e.g., at 5° C. in a $N_2$ atmosphere and/or ambient atmosphere). In some embodiments, the percentage of reduced ascorbic acid (e.g., % ASC) in the Composition of the Disclosure is between about 82% to about 100% or between about 85% to about 95% by weight of the total ascorbic acid in the Composition of the Disclosure following 4 weeks of storage (e.g., at 5° C. in a $N_2$ atmosphere and/or ambient atmosphere). In some embodiments, the percentage of reduced ascorbic acid (e.g., % ASC) in the Composition of the Disclosure is at least 80%, at least 85%, at least 86%, at least 87%, at least 88%, at least 89%, or at least 90% by weight of the total ascorbic acid in the Composition of the Disclosure following 4 weeks of storage (e.g., at 5° C. in a $N_2$ atmosphere and/or ambient atmosphere).

In some embodiments, the oxidized ascorbic acid in the Composition of the Disclosure is less than about 20%, less than about 18%, less than about 16%, less than about 15%, less than about 12%, less than about 10%, or less than about 9% by weight of the total ascorbic acid in the Composition of the Disclosure after storage of the Composition of the Disclosure for 4 weeks (e.g., at 5° C. in a $N_2$ atmosphere and/or ambient atmosphere). In some embodiments, the percentage of oxidized ascorbic acid in the Composition of the Disclosure is no more than about 5% to about 20%, about 5% to about 18%, about 5% to about 10%, or about 5% to 9% by weight of the total ascorbic acid in the Composition of the Disclosure following 4 weeks of storage (e.g., at 5° C. in a $N_2$ atmosphere and/or ambient atmosphere). In some embodiments, the percentage of oxidized ascorbic acid in the Composition of the Disclosure is less than about 20%, less than about 18%, less than about 16%, or less than about 10% by weight of the total ascorbic acid in the Composition of the Disclosure following 4 weeks of storage (e.g., at 5° C. in a $N_2$ atmosphere and/or ambient atmosphere).

In certain aspects, the ratios of the components of the Composition of the Disclosure are formulated to maximize formulation stability and minimize oxidation of glutathione and organic acid, e.g., ascorbic acid. In some embodiments, glutathione and organic acid (e.g., ascorbic acid) are formulated to comprise molar equivalents in solution, e.g., about 0.5-1:1, about 0.6-1:1, 0.7-1:1, 0.8-1:1, 0.9-1:1 or about 1:1 molar ratio of glutathione to ascorbic acid. In some embodiments, the glutathione and organic acid (e.g., ascorbic acid) are formulated to comprise molar excess of organic acid (e.g., ascorbic acid) relative to glutathione in solution, e.g., about 1:1.1, about 1:1.2, about 1:3, about 1:4, about 1:5 molar ratio of glutathione to ascorbic acid.

In some embodiments, the Composition of the Disclosure further comprises a bicarbonate salt (e.g., sodium bicarbonate). In some embodiments, glutathione, organic acid (e.g., ascorbic acid), and bicarbonate salt (e.g., sodium bicarbonate) are formulated to comprise a molar ratio of about 0.1-0.5:0.5-1:1, about 0.2-0.5:0.5-1:1, about 0.3-0.5:0.5-1:1, about 0.4-0.5:0.5-1:1, about 0.49:0.5-1:1, about 0.5:0.5-1:1, about 0.1-0.5:0.6-1:1, about 0.2-0.5:0.6-1:1, about 0.3-0.5:0.6-1:1, about 0.4-0.5:0.6-1:1, about 0.49:0.6-1:1, about 0.5:0.6-1:1, about 0.1-0.5:0.7-1:1, about 0.2-0.5:0.7-1:1, about 0.3-0.5:0.7-1:1, about 0.4-0.5:0.7-1:1, about 0.49:0.7-1:1, about 0.5:0.7-1:1, about 0.1-0.5:0.8-1:1, about 0.2-0.5:0.8-1:1, about 0.3-0.5:0.8-1:1, about 0.4-0.5:0.8-1:1, about 0.49:0.8-1:1, about 0.5:0.8-1:1, about 0.1-0.5:0.9-1:1, about 0.2-0.5:0.9-1:1, about 0.3-0.5:0.9-1:1, about 0.4-0.5:0.9-1:1, about 0.49:0.9-1:1, about 0.5:0.9-1:1, about 0.1-0.5:1:1, about 0.2-0.5:1:1, about 0.3-0.5:1:1, about 0.4-0.5:1:1, about 0.49:1:1, about 0.5:1:1, molar ratio of glutathione to organic acid (e.g., ascorbic acid) to bicarbonate salt (e.g., sodium bicarbonate). In some embodiments, the molar ratio of glutathione, organic acid (e.g., ascorbic acid), and bicarbonate salt (e.g., sodium bicarbonate) is 0.1-0.5:0.5-1:1, 0.4-0.5:0.5-1:1, 0.1-0.5:0.5:1, 0.1-0.5:1:1, or 0.4-0.5:1:1. In some embodiments, the molar ratio of glutathione, organic acid (e.g., ascorbic acid), and bicarbonate salt (e.g., sodium bicarbonate) is 0.49:0.5:1, 0.5:0.5:1, 0.49:1:1, or 0.5:1:1.

In some embodiments, the bicarbonate salt (e.g., sodium bicarbonate) is less than the combined molar ratio of (a) glutathione, a glutathione derivative, a glutathione conjugate, a pharmaceutically-acceptable salt thereof, or any combination thereof and (b) organic acid (e.g., ascorbic acid). In some embodiments, the molar ratio of glutathione, organic acid (e.g., ascorbic acid), and bicarbonate salt (e.g., sodium bicarbonate) is 0.1-0.49:0.5:1, 0.2-0.49:0.5:1, 0.3-0.49:0.5:1, or 0.4-0.49:0.5:1.

In some embodiments, Composition of the Disclosure comprises or consists essentially of (a) a glutathione, a glutathione derivative, a glutathione conjugate, pharmaceutically-acceptable salt thereof, or any combination thereof, and (b) an organic acid, wherein the molar ratio of (a) to (b) is about 0.5-1:1, about 0.6-1:1, 0.7-1:1, 0.8-1:1, 0.9-1:1 or about 1:1 and the pH of the composition is about 5.5 to 14, about 6 to about 8, 7±1.5, 6±0.5, or about 6.

In some embodiments, Composition of the Disclosure comprises or consists essentially of (a) a glutathione, a glutathione derivative, a glutathione conjugate, pharmaceutically-acceptable salt thereof, or any combination thereof, (b) an organic acid, (c) a bicarbonate salt, wherein the molar ratio of (a) to (b) to (c) is about 0.1-0.5:0.5-1:1, 0.4-0.5:0.5-

1:1, 0.1-0.5:0.5:1, 0.1-0.5:1:1, 0.4-0.5:1:1, 0.1-0.49:0.5:1, 0.2-0.49:0.5:1, 0.3-0.49:0.5:1, or 0.4-0.49:0.5:1 and the pH of the composition is about 5.5 to 14, about 6 to about 8, 7±1.5, 6±0.5, or about 6.

Pharmaceutical compositions for use in the present disclosure can be formulated using one or more physiologically acceptable carriers and/or excipients that facilitate administration of glutathione, a glutathione derivative, a glutathione conjugate, a pharmaceutically-acceptable salt thereof, or any combination thereof to a subject by an intended route, e.g., delivery by inhalation. In some embodiments, the pharmaceutical composition is an aqueous solution. In some embodiments, the pharmaceutical composition is a dry powder.

Compositions of the Disclosure can be manufactured by conventional mixing, dissolving, granulating, dragee-making, emulsifying, encapsulating, entrapping, spray drying, or lyophilizing processes that are known in the art. The particular formulation depends upon the route of administration chosen. In one embodiment, glutathione, a glutathione derivative, a glutathione conjugate, a pharmaceutically-acceptable salt thereof, or any combination thereof is dissolved in a solvent, e.g., water, for administration to the airway of a subject (e.g., intranasal administration).

The term "pharmaceutically acceptable carrier" refers to a pharmaceutically-acceptable material, composition, or vehicle, such as a liquid (e.g., water), or a solid filler, diluent, excipient, solvent, or encapsulating material. A carrier is "pharmaceutically acceptable" in the sense of being compatible with the other ingredients of a pharmaceutical formulation and suitable for use in humans without toxicity, irritation, allergic response, immunogenicity, or other complications commensurate with a reasonable benefit/risk ratio. See, Remington: The Science and Practice of Pharmacy, 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, Fla., 2004).

In some embodiments, Compositions of the Disclosure comprise an excipient. In some embodiments, the excipient is selected from the group consisting of a pH adjusting agent, a preservative, a chelating agent, and any combination thereof.

In certain embodiments, the Compositions of the Disclosure can comprise a pH adjusting agent. pH adjusting agents are known in the art. See, e.g., Remington's Pharmaceutical Sciences, 18th edition, A. R Gennaro, Ed., Mack Publishing Company (1990) and Handbook of Pharmaceutical Excipients, 3rd edition, A. Kibbe, Ed., Pharmaceutical Press (2000). Suitable examples of pharmaceutically acceptable pH adjusting agents include, but are not limited to, ascorbic acid, citric acid, sodium citrate, sodium bicarbonate, potassium bicarbonate, dibasic sodium phosphate, magnesium oxide, calcium carbonate, magnesium hydroxide, buffers (e.g., acetate buffers, citrate buffers, phosphate buffers, lactic acid buffers, and borate buffers, and any combination thereof), fat-soluble fatty acid esters of ascorbic acid (vitamin C) (e.g., alone or in combination with a-hydroxy acids), oxidation-resistant saturated fatty acid esters of ascorbic acid (e.g., ascorbyllaurate, ascorbyl myristate, ascorbyl palmitate, ascorbyl stearate, and ascorbyl behenate, and any combination thereof), and any combination thereof. In some embodiments, esters can be prepared using hydrogenated oils or fats, or fractions thereof, and contain small amounts of another ester. Ascorbyl stearate prepared using canola, for example, can commonly contain about 4% ascorbyl palmitate.

In one embodiment, the pH adjusting agent, e.g., ascorbic acid, is present in a Composition of the Disclosure in an amount of about 0.01-50% by weight, about 10-90% by weight, about 10-85% by weight, about 10-80% by weight, about 10-75% by weight, about 10-70% by weight, about 10-65% by weight, about 10-60% by weight, about 10-55% by weight, about 10-50% by weight, about 10-45% by weight, about 10-40% by weight, about 10-35% by weight, about 10-30% by weight, about 1-30% by weight, about 1-20% by weight, or about 1-10% by weight. In some embodiments, the pH adjusting agent is present in a Composition of the Disclosure at an amount of about 1% by weight, about 5% by weight, about 10% by weight, about 15% by weight, about 20% by weight, about 25% by weight, about 30% by weight, about 35% by weight, about 40% by weight, about 45% by weight, or about 50% by weight of the composition.

In certain embodiments, the Compositions of the Disclosure can comprise preservatives. Pharmaceutically acceptable preservatives include, but are not limited to, various antibacterial and antifungal agents, solvents (e.g., ethanol, propylene glycol, benzyl alcohol and chlorobutanol, and any combination thereof), quaternary ammonium salts (e.g., cetylpyridinium chloride, benzalkonium chloride and parabens including, but not limited to, methyl paraben, ethyl paraben and propyl paraben), chlorhexidine, benzoic acid and the salts thereof, parahydroxybenzoic acids and the salts thereof, alkyl esters of parahydroxybenzoic acid and the salts thereof, phenylmercuric salts such as nitrate, chloride, acetate, and borate, antioxidants, EDTA, sorbitol, phenol, boric acid and the salts thereof, sorbic acid and the salts thereof, thimerosal and nitromersol, and any combinations thereof.

In one embodiment, the preservative is present in a Composition of the Disclosure in about 0.01-50% by weight, e.g., about 1-30% by weight, about 1-20% by weight, or about 1-10% by weight, e.g., about 1% by weight, about 5% by weight, about 10% by weight, about 15% by weight, about 20% by weight, about 25% by weight, about 30% by weight, about 35% by weight, about 40% by weight, about 45% by weight, or about 50% by weight of the composition.

In certain embodiments, the Compositions of the Disclosure can comprise a chelating agent. Non-limiting examples of chelating agents include lactic acid, acetic acid, oxalic acid, malonic acid, succinic acid, maleic acid, fumaric acid, aconitic acid, pimelic acid, sebacic acid, allymalonic acid, ethylmalonic acid, citric acid, malic acid, glyceric acid, tartaric acid, mevaloic acid, oxyglutaric acid, oxaloacetic acid, a-ketoglutaric acid, a-ketomalonic acid, glucuronic acid, galaceturonic acid, mannuronic acid, aspartic acid, glutamic acid, glycine, alanine, lysine, histidine, alginine, cysteine, s-aminocaproic acid, phenylalanine, phenylglycine, p-hydroxyphenylglycine, p-aminophenylalanine, y-carboxyglutamic acid, iminodiacetic acid, hydroxyethyliminodiacetic acid, ethylenediaminediacetic acid, ethylenediaminetetraacetic acid, trans-cyclohexane-diaminetetraacetic acid, diethylenediaminepentaacetic acid, alaninediacetic acid, diaminopimelic acid, phthalic acid, terephthalic acid, homophthalic acid, phenylsuccinic acid, phenylmalonic acid, oxanylic acid-o-carboxylic acid, anthralininoacetic acid, 2,4-dihydroxybenzoic acid, p-aminosalicyclic acid, phthalyglutamic acid, kynurenine, 1,2-hyroxybenzene-3,5-disulfonic acid, 4-amino-phenol-2- sulfonic acid, cysteic acid, 2-phosphoglyceric acid, glycero-3-phosphoric acid, glucose-1,6-diphosphoric acid, fructose-1,6-diphosphoric acid and phosphates (e.g., sodium phosphate, sodium aluminum phosphate, sodium acid phosphate, dipotassium phosphate, disodium phosphate, monobasic and sodium hexametaphosphate), and any combination thereof. Chelating agents can be included in the pharmaceutical compositions of this disclosure either as the parent molecule or in the salt form where appropriate. For example, compounds containing an acid function can be used in the protonated form or as a pharmaceutically acceptable inorganic or organic salt which retains the chelating activity of the parent compound In one embodiment, the chelating agent is present in a Composition of the Disclosure in about 0.01-50% by weight, e.g., about 1-30% by weight, about 1-20% by weight, or about 1-10% by weight, e.g., about 1% by weight, about 5% by weight, about 10% by weight, about 15% by weight, about 20% by weight, about 25% by weight, about 30% by weight, about 35% by weight, about 40% by weight, about 45% by weight, or about 50% by weight of the composition.

In certain embodiments, the Composition of the Disclosure comprises glutathione, a glutathione derivative, a glutathione conjugate, a pharmaceutically-acceptable salt thereof, or any combination thereof; a bicarbonate (e.g., sodium bicarbonate or potassium bicarbonate) and/or a pH modifier (e.g., ascorbic acid). In some embodiments, the Composition of the Disclosure comprises glutathione, a glutathione derivative, a glutathione conjugate, a pharmaceutically-acceptable salt thereof, or any combination thereof and/or a pH modifier such as an organic acid (e.g., ascorbic acid). In some embodiments, the composition claimed wherein the amount of each component is present such that the amount of ascorbic acid is approximately molar equivalent or in molar excess of that of glutathione, a glutathione derivative, a glutathione conjugate, a pharmaceutically-acceptable salt thereof, or any combination thereof.

In some embodiments, a Composition of the Disclosure comprises (a) glutathione, a glutathione derivative, a glutathione conjugate, a pharmaceutically-acceptable salt thereof; (b) an organic acid; and (c) a bicarbonate salt. In further embodiments, the molar ratio of (a):(b):(c) in a Composition of the Disclosure is 0.1-0.5:0.5-1:1 (e.g., 0.4-0.5:0.5-1:1, 0.1-0.5:0.5:1, 0.1-0.5:1:1, 0.4-0.5:1:1, 0.1-0.49: 0.5:1, 0.2-0.49:0.5:1, 0.3-0.49:0.5:1, or 0.4-0.49:0.5:1).

In some embodiments, the organic acid in a Composition of the Disclosure is ascorbic acid. In some embodiments, the bicarbonate salt in a Composition of the Disclosure is sodium bicarbonate. In some embodiments, the composition comprises: (a) glutathione; (b) ascorbic acid; and (c) sodium bicarbonate. In certain embodiments, the molar ratio of (a):(b):(c) is about 0.1-0.5:0.5-1:1 (e.g., about 0.49:about 0.50:about 1). In other embodiments, the molar ratio of (a):(b):(c) is about 0.1-0.5:1:1 (e.g., about 0.49:about 1:about 1).

In some embodiments, the pH of a Composition of the Disclosure is from about 5.5 to about 14 (e.g. 5.5 to 7.5). In some embodiments, the pH of a Composition of the Disclosure is from about 6 to about 14 (e.g., 6 to 7.5). In some embodiments, the pH of the composition is 7±1.5, 7±1.4, 7±1.3, 7±1.2, 7±1.1, 6±0.5, 6±0.4, 6±0.3, 6±0.2, 6±0.5, 6±0.1, or about 6.

Methods of Use

In some embodiments, the Compositions of the Disclosure are useful for inhibiting or reducing growth of a clinical isolate bacteria.

In some embodiments, the Compositions of the Disclosure are useful for inhibiting or reducing formation of a clinical isolate bacteria biofilm.

In some embodiments, the Compositions of the Disclosure are useful for treating, reducing the symptoms of, or preventing a variety of diseases, conditions, or disorders.

In some embodiments, the Compositions of the Disclosure are useful for treating or reducing symptoms in a subject suffering from or at risk for a clinical isolate bacteria infection.

In one embodiment, the subject has a pulmonary or airway disorder.

In another embodiment, the pulmonary or airway disorder can be, but is not limited to, chronic inflammatory lung disease, pulmonary fibrosis, pulmonary vasculitis, pulmonary sarcoidosis, an inflammation and/or infection associated with lung transplantation, acute or chronic lung rejection and/or dysfunction, pulmonary artery hypertension, bronchitis, sinusitis, asthma, cystic fibrosis, a bacterial infection, a fungal infection, a parasite infection, a viral infection, chronic obstructive pulmonary disease (COPD), bronchiolitis obliterans syndrome (BOS), primary ciliary dyskinesia (PCD), alveolar protienosis, idiopathic pulmonary fibrosis, eosinophilic pneumonia, eosinophilic bronchitis, acute respiratory distress syndrome (ARDS), an inflammation and/or infection associated with mechanical ventilation, ventilator-associated pneumonia, an asbestos-related airway disorder or disease, a dust-related airway disorder or disease, silicosis, and a chemical agent-related airway disease or disorder, and any combination thereof. In another embodiment, the method further comprises administering an additional therapeutic agent to the subject.

In another embodiment, the present disclosure provides methods of treating or preventing a clinical isolate bacteria infection in the airway of a subject in need thereof, the method comprising administering to the subject a therapeutically effective amount of a Composition of the Disclosure. In another embodiment, a Composition of the Disclosure is administered to the subject in combination with one or more antibiotics. The antibiotics can be administered locally to the lungs and/or systemically.

In another embodiment, the present disclosure provides methods of treating or preventing inflammation in the airway of a subject in need thereof, the method comprising administering to the subject a therapeutically amount of a Composition of the Disclosure.

In another embodiment, the present disclosure provides methods of treating or preventing a disease or disorder in mucosal tissue in a subject in need thereof, the method comprising administering to the subject a therapeutically effective amount of a Composition of the Disclosure. Non-limiting examples of mucosal tissue include the mouth, nose, eye, ear, upper respiratory tract, lower respiratory tract, gastrointestinal tract, vagina, rectum and urethra.

In another embodiment, the present disclosure provides methods of treating or preventing a disease or disorder associated with mucosal membranes, in a subject in need thereof, the method comprising administering to the subject a therapeutically amount of a Composition of the Disclosure to the appropriate mucosal membranes. In one embodiment, the mucosal membranes are the lungs, such as the deep lung (alveolar region), and in other embodiments, the mucosal membranes are one or more of the eyes, mouth, nose, rectum, and vagina.

In another embodiment, a Composition of the Disclosure can be used to treat or prevent bronchiolitis obliterans and military-related lung damage, i.e., lung damage of military personnel who have damaged airways secondary to unknown exposures.

In another embodiment, the present disclosure provides the use of a Composition of the Disclosure for the manufacture of a medicament for treatment of a pulmonary or airway disorder. In another embodiment, the use further comprises administering one or more additional therapeutic agents to the subject.

The therapeutic methods of this disclosure comprise administering a therapeutically effective amount of a Composition of the Disclosure to a subject in need thereof, e.g., a human patient. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

In one embodiment, the present disclosure provides a method for treating a pulmonary or airway disorder or disease in a subject infected with a clinical isolate bacteria or at risk for infection with a clinical isolate bacteria, the method comprising administering to the subject an effective amount of a composition comprising: (a) a Conjugate Compound of the Disclosure; and/or (b) glutathione, or a pharmaceutically acceptable salt thereof.

In another embodiment, the pulmonary or airway disorder or disease is selected from the group consisting of chronic inflammatory lung disease, an inflammation and/or infection associated with lung transplantation, acute lung rejection, asthma, cystic fibrosis, and chronic obstructive pulmonary disease (COPD), and any combination thereof.

In another embodiment, the pulmonary or airway disorder or disease is treated by inhibiting clinical isolate bacteria growth in the airway of the subject.

In another embodiment, the present disclosure provides a method of restoring homeostasis to and/or maintaining homeostasis in a mucosal membrane of a subject in need thereof, the method comprising administering to the subject an effective amount of a composition comprising: (a) a Conjugate Compound of the Disclosure; and/or (b) glutathione, or a pharmaceutically acceptable salt thereof.

In another embodiment, the subject has a pulmonary or airway disorder or disease.

In another embodiment, the pulmonary or airway disorder or disease is selected from the group consisting of chronic inflammatory lung disease, inflammation and/or infection associated with lung transplantation, acute lung rejection, asthma, cystic fibrosis, and chronic obstructive pulmonary disease (COPD), and any combination thereof.

In another embodiment, homeostasis in a mucosal membrane is restored and/or maintained by inhibiting microbial growth in the airway of the subject.

In another embodiment, the present disclosure provides a method of treating, reducing or inhibiting growth of a clinical isolate bacteria in an airway of a subject, the method comprising administering to the airway of the subject an effective amount of a composition comprising: a Conjugate Compound of the Disclosure and/or glutathione, or a pharmaceutically acceptable salt thereof.

In another embodiment, the composition further comprises: an organic acid, or a pharmaceutically acceptable salt thereof.

In another embodiment, the organic acid is ascorbic acid.

In another embodiment, the composition further comprises: a bicarbonate salt.

In another embodiment, the bicarbonate salt is sodium bicarbonate or potassium bicarbonate.

In another embodiment, the amount of each of component the Conjugate Compound of the Disclosure and/or the glutathione, or a pharmaceutically acceptable salt thereof, the organic acid, or a pharmaceutically acceptable salt thereof, and the bicarbonate salt of the composition is present such that the amount of bicarbonate salt results in a pH in a range from about 5 to about 9.

In another embodiment, the composition further comprises from about 0.01% to about 5% by weight of a pharmaceutically-acceptable thiocyanate salt.

In another embodiment, the composition is in the form of a particle.

In another embodiment, the particle is mixed with a gas or liquid propellant for use in inhalation therapy.

In another embodiment, the glutathione is oxidized glutathione.

In another embodiment, the glutathione is reduced glutathione.

In another embodiment, administration of the composition to the subject gives a concentration of about 0.1 mM to about 1.0 mM glutathione in the airway surface liquid of the subject.

In another embodiment, administration of the composition to the subject gives a concentration of about 0.5 mM to about 3.0 mM thiocyanate in the airway surface liquid of the subject.

In another embodiment, the composition is administered by inhalation to the subject.

Administration

The therapeutic methods of this disclosure can be accomplished by administering a Composition of the Disclosure to a subject. Administration of a Composition of the Disclosure can be performed before, during, or after the onset of the disease, condition, or disorder of interest. Typically, the pharmaceutical compositions are sterile, and contain no toxic, carcinogenic, or mutagenic compounds that would cause an adverse reaction when administered to the subject.

Compositions of the Disclosure are administered in a manner compatible with the dosage formulation in such an amount as will be effective for the desired result. In particular embodiments, Compositions of the Disclosure are administered to the subject in a therapeutically effective amount. A therapeutically effective amount of Compositions of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of glutathione that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, glutathione, a glutathione derivative, a glutathione conjugate, a pharmaceutically-acceptable salt thereof, or any combination thereof can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days' rest, and another five daily doses (5/2/5); or, any dose regimen determined to be appropriate for the circumstance.

Compositions of the Disclosure can be administered for a sustained period, such as for at least about one month, at least about 2 months, at least about 3 months, at least about 6 months, or at least about 12 months or longer (e.g., as a chronic life-long treatment).

Any suitable dosing schedule can be followed. For example, the dosing frequency can be a once weekly dosing. The dosing frequency can be a once daily or multiple times daily dosing. The dosing frequency can be more than once weekly dosing. The dosing frequency can be more than once daily dosing, such as any one of 2, 3, 4, 5, 6, 7, 8, 9, 10 or more than 10 daily doses. The dosing frequency can be intermittent (e.g., multiple daily dosing for 7 days followed by no doses for 7 days, repeated for any 14 day time period, such as 2 months, 4 months, 6 months or more). The dosing frequency can be continuous (e.g., one weekly dosing for continuous weeks).

Glutathione, a glutathione derivative, a glutathione conjugate, a pharmaceutically-acceptable salt thereof, or any combination thereof used in a therapeutic method of the present disclosure can be administered in an amount of about 0.005 to about 1,000 milligrams per dose, about 0.05 to about 250 milligrams per dose, or about 0.5 to about 100 milligrams per dose. For example, glutathione, a glutathione derivative, a glutathione conjugate, a pharmaceutically-acceptable salt thereof, or any combination thereof can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 1,000 milligrams.

The dosage of glutathione, a glutathione derivative, a glutathione conjugate, a pharmaceutically-acceptable salt thereof, or any combination thereof, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition can be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

In one embodiment, glutathione, a glutathione derivative, a glutathione conjugate, a pharmaceutically-acceptable salt thereof, or any combination thereof is delivered to the upper third of the nasal cavity, to the superior meatus, the olfactory region and/or the sinus region of the nose. The olfactory region is a small area that is typically about 2-10 $cm^2$ in man located in the upper third of the nasal cavity for deposition and absorption by the olfactory epithelium and subsequent transport by olfactory receptor neurons. Located on the roof of the nasal cavity, in the superior meatus, the olfactory region is useful for delivery in some embodiments, because it is the only known part of the body in which an extension of the CNS comes into contact with the environment (Bois et al. Fundamentals of Otolaryngology, p. 184, W. B. Saunders Co., Philadelphia, 1989).

In some embodiments, a Composition of the Disclosure can be administered in a single "shock" dose, for example, during a bronchoscopy. In other embodiments, the methods of the disclosure can be carried out on an as-needed basis by self-medication.

Any of the dosing frequencies can be used with any dosage amount. Further, any of the dosing frequencies and/or dosage amounts can be used with any of the Compositions of the Disclosure.

A Composition of the Disclosure can be delivered in any suitable volume of administration, In representative embodiments of the disclosure, the administration volume for intranasal delivery ranges from about 25 microliters to 200 microliters or from about 50 to 150 microliters or from about 50, 100, 250 or 500 microliters to about 1, 2, 3, 3.5 or 4 milliliters in a human. Typically, the administration volume is selected to be large enough to allow for delivery of therapeutic quantities while accounting for dilution in ASL in maintenance conditions in relatively "normal" airways (10-30 ml ASL) and in cystic fibrosis (CF) airways (40-50 ml ASL or more plus thick, tenacious, and heavily infected mucus secretions).

The Compositions of the Disclosure can find use in both veterinary and/or medical applications. Suitable subjects of the present disclosure include, but are not limited to mammals. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), etc. In some embodiments of the present disclosure, the subject is a human. Human subjects include both males and females and subjects of all ages including neonatal, infant, juvenile, adolescent, adult, and geriatric subjects.

In some embodiments, a Composition of the Disclosure is administered one or more times daily (e.g., 1, 2, 3, 4, 5, 6, 7, 8, 9, 10 or more times a day). In particular embodiments, the subject is a human.

In some embodiments of the methods of this disclosure, a Composition of the Disclosure can be administered via inhalation, intranasally, via the eye, via the ear, via sinus irrigation, or via bronchoscope, or any combination thereof.

Intranasal administration of a Composition of the Disclosure can be achieved by any known method. In particular embodiments, intranasal administration is by inhalation (e.g., using an inhaler, atomizer or nebulizer device), alternatively, by spray, tube, catheter, syringe, dropper, packtail, pipette, pledget, and the like.

As a further illustration, a Composition of the Disclosure can be administered intranasally as (1) nose drops, (2) powder or liquid sprays or aerosols, (3) liquids or semisolids by syringe, (4) liquids or semisolids by swab, pledget or other similar means of application, (5) a gel, cream or ointment, (6) an infusion, or (7) by injection, or by any means now known or later developed in the art. In particular embodiments, the method of delivery is by nasal drops, spray or aerosol. As used herein, aerosols can be used to deliver powders, liquids or dispersions (solids in liquid).

In some embodiments, the pharmaceutical formulation is directed upward during administration, so as to enhance delivery to the upper third (e.g., the olfactory epithelium in the olfactory region) and the side walls (e.g., nasal epithelium) of the nasal cavity. Further, orienting the subject's head in a tipped-back position or orienting the subject's body in Mygind's position or the praying-to-Mecca position can be used to facilitate delivery to the olfactory region.

The formulations can be provided in single or multidose form. In the latter case a means of dose metering can be provided. In the case of a dropper or pipette, this can be achieved by the patient or caregiver administering an appropriate, predetermined volume of the composition. In the case of a spray, this can be achieved, for example, by means of a metering atomizing spray pump.

In a further aspect, the present disclosure provides an intranasal spray device comprising a Composition of the Disclosure.

Many devices are known in the art for nasal delivery. Exemplary devices include particle dispersion devices, bidirectional devices, and devices that use chip-based ink jet technologies.

When a therapeutically effective amount of a Composition of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A composition for intravenous, cutaneous, or subcutaneous injection typically contains an isotonic vehicle.

Compositions of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of glutathione, a glutathione derivative, a glutathione conjugate, a pharmaceutically-acceptable salt thereof, or any combination thereof can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Glutathione, a glutathione derivative, a glutathione conjugate, a pharmaceutically-acceptable salt thereof, or any combination thereof also can be formulated in rectal compositions, such as suppositories or retention enemas, e.g., containing conventional suppository bases. In addition to the formulations described previously, glutathione, a glutathione derivative, a glutathione conjugate, a pharmaceutically-acceptable salt thereof, or any combination thereof also can be formulated as a depot preparation. Such long-acting formulations can be administered by implantation (for example, subcutaneously or intramuscularly) or by intramuscular injection. Thus, for example, glutathione, a glutathione derivative, a glutathione conjugate, a pharmaceutically-acceptable salt thereof, or any combination thereof can be formulated with suitable polymeric or hydrophobic materials (for example, as an emulsion in an acceptable oil) or ion exchange resins.

Compositions of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compositions of the Disclosure also can be injected parenterally, for example, intravenously, intramuscularly, subcutaneously, or intracoronarily. For parenteral administration, the Compositions of the Disclosure are typically used in the form of a sterile aqueous solution which can contain other substances, for example, salts or monosaccharides, such as mannitol or glucose, to make the solution isotonic with blood.

Compositions of the Disclosure can be present, for example, as a solid formulation, such as a particle formulation, or as a solution. When in a particle formulation, the particles can be mixed with gases, or liquid propellants, for use in inhalation therapy. Other solid formulations include formulations for oral administration, buccal administration or colonic administration, and suppositories for rectal or vaginal administration. Exemplary formulations include, but are not limited to, the following: eye drops, nebulizers, topical gels and ointments, dry powders, particles, sprays, liquids, anesthetic machines or vaporizers, autoinjectors, intrauterine devices, respimats, liniments, liposomes, lotions, formulations for intramuscular, intrathecal, or subcutaneous injection, douches, infusions, and face masks.

In solution form, the formulations can be in the form of sprays for intranasal administration, formulations for use in nebulizers, and formulations for rectal administration, such as enemas and colonies. Solutions that include water-miscible organic solvents, such as propylene glycol and/or glycerol, and other components normally found in vaginal and rectal lubricants, can also be used. Regardless of the solvents used, the solvent is typically present in a weight ratio of from about 15 to about 85 percent by weight, relative to the weight of the solids, and, more typically, is from about 50 to about 85% by weight.

The compositions and/or formulations of this invention can be used to treat disorders associated with a mucosal membrane, by delivering the compositions and/or formulations to the mucosal membrane(s) to be treated. In some embodiments, the mucosal membrane can be in or near the lungs, such as the deep lung (alveolar region), and in other embodiments, the mucosal membrane(s) can be in or near one or more of the eyes, mouth, nose, rectum, and/or vagina.

Additional Therapeutic Agents

In another embodiment, the present disclosure provides a method comprising administering to the subject an effective amount of an additional therapeutic agent.

Compositions comprising glutathione, a glutathione derivative, a glutathione conjugate, a pharmaceutically-acceptable salt thereof, or any combination thereof can also be combined with antibiotics to increase efficacy of treatment.

In another embodiment, one object of the invention is to identify clinical isolates in a patient sample and test efficacy of treatment in vitro by treatment with a composition comprising glutathione, a glutathione derivative, a glutathione conjugate, a pharmaceutically-acceptable salt thereof, or any combination thereof.

Drugs administered to the lungs are often associated with certain side effects, in some cases because of dosage, and in other cases because they damage the lung tissue. In some embodiments, therapeutic agents combined with the compositions disclosed herein are effective at lower doses, and at such lower doses, the incidence of side effects can be reduced. In other embodiments, where the therapeutic agent interacts unfavorably with lung tissue, the compositions described herein can help to restore homeostasis to the lung tissue, and thus help minimize or eliminate damage caused by the therapeutic agents.

In another embodiment, the present disclosure provides a the therapeutic agent is selected from the group consisting of Fluticasone, Budesonide, Mometasone, Ciclesonide, Flunisolide, Beclomethasone, Albuterol, Levalbuterol, Ipratropium, Tiotropium, Formoterol, Arformoterol, Indacaterol, Aclidinium, and Pirbuterol, penicillins such as Amoxicillin, Ampicillin, Azlocillin, Carbenicillin, Cloxacillin, Cayston, Dicloxacillin, Flucloxacillin, Mezlocillin, Methicillin, Nafcillin, Oxacillin, Penicillin G, Penicillin V, Piperacillin, Penicillin G, Temocillin, and Ticarcillin, and combinations of penicillins with other therapeutic agents, such as Amoxicillin/clavulanate, Ampicillin/sulbactam, Piperacillin/tazobactam, Ticarcillin/clavulanate, and any combination thereof.

In one embodiment, the therapeutic agent is selected from the group consisting of Fluticasone, Budesonide, Mometasone, Ciclesonide, Flunisolide, Beclomethasone, Albuterol, Levalbuterol, Ipratropium, Tiotropium, Formoterol, Arformoterol, Indacaterol, Aclidinium, Cayston, Pirbuterol, and any combination thereof.

Additional therapeutic agents that can be combined with the compositions and formulations of this invention include, but are not limited to, Fluticasone (for example, sold as Flovent diskus 50 or as Flonase, GlaxoSmithKline), Budesonide (for example, sold as Pulmicort respules or Rhinocort by Astra Zeneca ("AZ"), Mometasone (sold as Nasonex as a spray, or as Asmanex Twisthaler by Merck/S-P), Ciclesonide (sold as Alvesco or Onmaris by Takeda Pharmaceuticals), Flunisolide (sold as Aerobid by Roche Palo or by Aerospan HFA by GSK), Beclomethasone (sold as Qvar or Onasl by Teva Pharmaceuticals), Albuterol (sold as ProAir HFA by Teva and as Ventolin HFA by GSK), Levalbuterol (sold as Xopenex by Sunovion), Ipratropium (sold as Atrovent by BI), Tiotropium (sold as Spiriva by BI), Salmeterol (sold as Serevent by GSK), Formoterol (sold as Foradil by Novartis and as Perforomist by Dey Pharma), Arformoterol (sold as Brovana by Sunovion), Indacaterol (sold as Arcapta by Novartis), Aclidinium (sold as Tudorza by Forest Labs), Pirbuterol (sold as Maxair by Medicis), and any combination thereof.

The present methods encompass administering one or more additional therapeutic agents to the subject in combination with a Composition of the Disclosure. In one embodiment, a Composition of the Disclosure further comprises, or the Composition is administered in combination or in alternation with, an additional therapeutic agent. That is, in some embodiments, the composition and further therapeutic agents are directed to the same locus in the same formulation, and in other embodiments, the composition can be administered via one pathway, and the further therapeutic agent(s) can be administered via a different pathway.

The additional therapeutic agent is typically selected from drugs known as useful in treating the disease, condition, or disorder afflicting the subject in need thereof. The choice of additional therapeutic agent(s) will depend on the disease, condition, or disorder to be treated or prevented in a subject. This determination is within the capability of those skilled in the art, especially in light of the present disclosure.

In one embodiment, one additional therapeutic agent is administered to the subject. In another embodiment, two additional therapeutic agents are administered to the subject. In another embodiment, three additional therapeutic agents are administered to the subject. In another embodiment, four additional therapeutic agents are administered to the subject. In another embodiment, five additional therapeutic agents are administered to the subject. In another embodiment, five or more additional therapeutic agents are administered to the subject. Non-limiting exemplary therapeutic agents are anti-fungal agents, antiviral agents, antibacterial agents, anti-inflammatory agents, immunosuppressive agents, bronchodilators, airway modulators, alpha lipoic acid, alpha tocopherol, docosahexanic acid, proline, glycine, curcumin, arginine, thiocyanate, glutathione, oxidized glutathione, reduced glutathione, cysteine, hypothiocyanate, lactoferrin, and lactoperoxidase, and any combination thereof. In another embodiment, the one or more therapeutic agents are glutathione, oxidized glutathione, or reduced glutathione.

A Composition of the Disclosure and an additional therapeutic agent can be administered together as a single-unit dose or separately as multi-unit doses, wherein the Composition of the Disclosure is administered before the additional therapeutic agent, after the additional therapeutic agent, or concurrently with the additional therapeutic agent. One or more doses of the Composition of the Disclosure and/or one or more doses of the additional therapeutic agent can be administered to the subject.

In another embodiment, the additional therapeutic agent treats the desired disorder for which it is administered, but can cause certain side effects, e.g., drying of the mucosal membranes that results in discomfort and/or injury that can be addressed by administering a Composition of the Disclosure.

In another embodiment, a Composition of the Disclosure treats the desired disorder for which it is administered, but can cause certain side effects, e.g., drying of the mucosal membranes that results in discomfort and/or injury that can be addressed by administering an additional therapeutic agent.

In some embodiments, the one or more additional therapeutic agent(s) and the Composition of the Disclosure both treat the underlying disorder, though via different means, such that an additive or synergistic effect can be achieved. As a result, in some aspects of this embodiment, lower doses of the additional therapeutic agent can be effective, which lower doses can result in fewer side effects, or provide other benefits to the subject.

When a Composition of the Disclosure and one or more additional therapeutic agents are not administered concurrently, it is understood that they can be administered in any order to a subject in need thereof. For example, a Composition of the Disclosure can be administered prior to, e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before, concomitantly with, or subsequent to, e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after, the administration of one or more additional therapeutic agents to a subject in need thereof. In some embodiments, a Composition of the Disclosure and the one or more additional therapeutic agents are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart. In one embodiment, the components of the combination therapies are administered at about 1 minute to about 24 hours apart.

In another embodiment, the additional therapeutic agent is an inhaled corticosteroid (ICS) or bronchodilator.

Prophylaxis

In addition to providing methods of treatment, the Compositions of the Disclosure can also be used to reduce the symptoms of or provide prevention of various diseases and disorders associated with a bacterial clinical isolate infection.

Embodiments of the present disclosure can be further defined by reference to the following non-limiting examples, which describe in detail preparation of certain compositions of the present disclosure and methods for using compositions of the present disclosure. It will be apparent to those skilled in the art that many modifications, both to materials and methods, can be practiced without departing from the scope of the present disclosure.

In Vitro Analysis of Clinical Isolate Bacteria

Clinical isolate samples from a subject can include, but are not limited to, sputum, airway samples, surgical tissue samples, autopsy samples, and blood. Samples can be fixed and/or stored at −20° C. or −80° C.

Isolation of CI species of clinical isolate bacteria can be accomplished by any technique known in the art. Species of CIs can be isolated from pure cultures (i.e., having only one CI species) or from a sample with multiple bacteria. Common methods to isolate species of CIs include, but are not limited to, serial dilution of initial clinical sample, centrifugation, plate-streaking with or without an initial growth step in liquid medium, and growth of individual colonies of bacteria on a solid or liquid medium. CIs are grown using any media known in the art, including but not limited to, planktonic and solid media.

Clinical isolate bacteria can be identified using any technique known in the art including, but not limited to morphological techniques (e.g., Gram staining, acid fast stains); biochemical, serological, or protein expression tests (e.g., interaction with antibodies, slide agglutination, ELISA, Western blotting, immunohistochemistry, immunofluorescence, flow cytometry); phage typing; and DNA- and/or RNA-based methods (e.g., DNA sequencing, G+C comparisons, gPCR, RT-PCR, qPCR, rRNA sequencing, DNA fingerprinting by restriction fragment length polymorphisms (RFLPs), nucleic acid hybridization (e.g., Northern blotting, Southern blotting), microarrays, in situ hybridization, including FISH).

Growth of clinical isolates in the presence of a drug (e.g., an antibiotic) with or without the composition of the disclosure, in the absence of a drug with or without the composition of the disclosure, or a placebo with or without the composition of the disclosure can be tested using any technique known in the art including, but not limited to, dilution and time-lapsed growth of CIs; identification of minimum inhibitory concentrations (MICs); determination of minimum biofilm eliminating concentration (MBC); and other methods known in the art (e.g., disk diffusion method, E-test (AB Biodisk, Solna, Sweden), any commercially available automated susceptibility testing system (e.g., the Vitek System (bioMerieux, France), the Walk-Away System (Dade International, Sacramento, Calif.), enzyme (e.g., beta lactamase)). Growth of CIs is tested in planktonic or biofilm cultures.

In some aspects, the present disclosure includes measurement of the minimum inhibitory concentrations (MICs). MICs can be determined on Miller-Hinton (MH) agar plates or in planktonic cultures by broth microdilution in MH. MICs can be determined for clinical isolate strains and/or lab-type reference strain PAO1. In some embodiments, the clinically efficacious MIC range of the composition is about 1%-50%, about 1%-40%, about 5%-50%, about 5%-40%, about 5%-35%, about 10%-50%, about 10%-40%, about 10%-35%, or about 12%-32%.

In some aspects, the present disclosure includes measurement of biofilm formation in vitro for clinical isolate bacteria. In some embodiments, an overnight culture of bacteria is grown in LB with and without the composition of the disclosure with shaking. The culture is then diluted 1:100, and 100-L aliquots added to a 96-well plate, which are incubated for 72 h at 37° C. to allow for the adequate growth of the clinical isolates. After two to three washes with water, crystal violet is added for 15 min followed by three rinses with water then the addition of 95% ethanol. The materials are then transferred to a fresh 96-well plate, and absorbance at 540 nm determined.

In some aspects, the present disclosure includes measurement of the minimum biofilm eliminating concentration (MBC) of CIs. For the minimum biofilm concentrations (MBC), a protocol similar to the MIC protocol can be used except the bacteria is seeded on a plate used for bacterial adherence. In some embodiments, optical densities are measured to determine the MBC for bacterial isolate. In some embodiments, the assay involves the formation of 96 identical biofilms on plastic pegs on the lid of an MBC device. Biofilms are then exposed to test antibiotics for a defined time period, then placed in fresh bacteriologic medium in a second 96-well plate and incubated overnight. The MBC value is the lowest dilution that prevents regrowth of bacteria from the treated biofilm.

The present disclosure allows for any of the above techniques in the presence or absence of nitrate.

The present disclosure allows for any of the above techniques in the presence or absence of oxygen.

The present disclosure allows for any of the above techniques in the presence or absence of one or more antibiotics.

EXAMPLES

It is understood that the examples and embodiments described herein are for illustrative purposes only and that various modifications or changes in light thereof will be suggested to persons skilled in the art and are to be included within the spirit and purview of this application.

Example 1: In Vitro Minimal Inhibitory Concentration (MIC) of Glutathione Compositions Against Bacterial Clinical Isolates Composition 1 was prepared with 150 mg/ml glutathione, 88 mg/ml ascorbic acid and 84 mg/ml sodium bicarb based on 322 total mg/ml weight, which corresponds to % total weight of about 46.6%, 27.3% and 26.1%, respectively. The molar ratio of the components in Composition 1 were 0.49 M glutathione, 0.50 M ascorbic acid, and 1 M HCO$_3$.

The MICs of Composition 1 (glutathione, ascorbic acid, and HCO$_3$); glutathione and ascorbic acid; and HCO$_3$ were tested against clinical isolates, including *Burkholderia cepacia, Pseudomonas aeruginosa* (Schroeter) Migula (ATCC 27853), *Pseudomonas aeruginosa* (Schroeter) Migula (ATCC 9027), *Pseudomonas aeruginosa* (Schroeter) Migula (ATCC BAA-2114), *Klebsiella pneumonia*, methicillin resistant *Staphylococcus aureus*; laboratory strains of *Moraxella catarrhalis, Stenotrophomonas maltophilia, Acinetobacter baumannii*; and eight samples of mucoid and nonmucoid *Pseudomonas aeruginosa* clinical isolates from human lung. The MIC for laboratory clinical isolate *Pseudomonas aeruginosa* (Schroeter) Migula (ATCC BAA-47 (PAO1)) was also tested. The MICs were determined under anaerobic conditions on media supplemented with nitrate, under aerobic conditions supplemented with nitrate, or under ambient conditions.

The clinical isolates were inoculated in duplicate on agar plates overnight under anaerobic conditions at 36° C.±1.0° C. in a 96-well plate. Laboratory isolates of *Burkholderia cepacia* were also grown in duplicate overnight under aerobic conditions at 36° C.±1.0° C. in a 96-well plate. Colonies from each clinical isolate grown on the agar plates then were chosen to inoculate 96-well plates in duplicate and were tested under three test solution conditions: Composition 1 (glutathione, ascorbic acid, and HCO$_3$); glutathione and ascorbic acid; and HCO$_3$ were diluted and added to the media. Ten dilutions for each test solution were examined: 50%, 25%, 12.5%, 6.25%, 3.13%, 1.57%, 0.78%, 0.39%, 0.2%, and 0.1%. The colony isolates were incubated for 12 hours or 24 hours at 36° C.±1.0° C. under anaerobic conditions in media comprising Luria Agar/Broth and nitrate with one of the three test solutions. In an additional test, *Burkholderia cepacia* and *Klebsiella pneumoniae* were grown in aerobic media comprising only Luria Agar/Broth with Composition 1. The MIC of Composition 1 was also determined for certain *Pseudomonas aeruginosa* lab and clinical isolates, *Moraxella catarrhalis, Stenotrophomonas maltophilia, Acinetobacter baumannii*, and *Burkholderia cepacia* grown under aerobic conditions comprising 1% nitrate. MICs were determined via visual inspection and OD$_{620}$. The MICs at 12, 24, and/or 48 hours in the clinical isolates tested are listed in Table 16.

TABLE 16

| Organism | Anaerobic (+nitrate) | | | Aerobic (+nitrate) | Aerobic (Ambient) |
| --- | --- | --- | --- | --- | --- |
| | Composition 1 | GSH + ASC | HCO3 | Composition 1 | Composition 1 |
| Bc 25416 | 25% (24 hrs); 6.25% (48 hours) | | | 6.25% (12 hours) | 3.13% (12 hrs); 25% (24 hrs) |
| Kp 4352 | 25% (12 hrs); 25% (24 hrs) | | | | 50% (12 hrs); 50% 12 hrs) |
| Pa 27853 | 12.5% (12 hrs); 12.5% (24 hrs) | | | | |
| Pa 9027 | 6.25% (12 hrs); 25% (24 hrs) | 6.25% (12 hrs) | | | |
| Pa BAA-2114 | 3.13% (12 hrs) | 0.39% (12 hrs) | | | |
| Pa BAA-47 (PAO1) | 6.25% (12 hrs) | 0.39% (12 hrs) | 12.5% (12 hrs) | 6.25% (12 hours) | |
| Pa UAB-NM-1 | 12.5% (12 hrs) | 0.78%(12 hrs) | 12.5%(12 hrs) | 1.56% (12 hours) | |
| Pa UAB-M-2 | 6.25% (12 hrs) | 0.39%(12 hrs) | 12.5%(12 hrs) | 3.13% (12 hours) | |
| Pa UAB-NM-3 | 6.25% (12 hrs) | 0.78% (12 hrs) | 12.5% (12 hrs) | | |
| Pa UAB-4 | 6.25% (12 hrs) | | | | |
| Pa UAB-NM-5 | 6.25% (12 hrs) | 0.78% (12 hrs) | 12.5% (12 hrs) | | |
| MRSA UAB-1 | 12.5% (12 hrs) | 0.39% (12 hrs) | 25% (12 hrs) | | |
| MRSA UAB-2 | 25% (12 hrs) | 0.39% (12 hrs) | | | |
| MRSA UAB-3 | 6.25% (12 hrs) | 0.39% (12 hrs) | 25% (12 hrs) | | |
| MRSA UAB-4 | 25% (12 hrs) | 0.39% (12 hrs) | | | |
| Mc ATCC 25238 | | | | 1.56% (12 hours) | |
| Sm ATCC 13636 | | | | 6.25% (12 hours) | |
| Ab ATCC 19606 | | | | 6.25% (12 hours) | |

Bc: *Burkholderia cepacia*
Kp: *Klebsiella pneumonia*
Pa: *Pseudomonas aeruginosa*
Pa UAB: *P. aeruginosa* clinical isolates from lung
MRSA: Methicillin-resistant *Staphylococcus aureus*
Mc: *Moraxella catarrhalis*
Sm: *Stenotrophomonas maltophilia*
Ab: *Acinetobacter baumannii*
NM: Nonmucoidy
M: Mucoidy An in vitro assay for MIC, i.e., the lowest concentration of a test substance or drug that inhibits bacterial growth, can be measured by optical density or visualization of no growth. MIC is often used to indicate the efficacy of an antibacterial drug. A lower MIC generally corresponds to a more potent drug.

The results show that Composition 1 inhibits bacteria even though the bicarbonate in the solution decreased the efficacy of glutathione in vitro. MIC for bicarbonate alone was measured for representative bacterial isolates to determine the contribution of bicarbonate to the inhibition in vitro.

The results show that Composition 1 was clinically efficacious against *Pseudomonas aeruginosa* lab and clinical isolates, *Burkholderia cepacia, Klebsiella pneumoniae*, methicillin resistant *Staphylococcus aureus, Moraxella catarrhalis, Stenotrophomonas maltophilia*, and *Acinetobacter baumannii*. Notably, lab and clinical isolate *Pseudomonas aeruginosa* phenotypes can vary dramatically based on the conditions under which they are maintained, their passage number and the environment from which they were isolated. Therefore, PAO1 is not predictive of how other lab or clinical isolates will be inhibited.

The anaerobic and aerobic effects on *B. cepacia* and *K. pneumoniae* were also assessed in vitro. Both of these bacteria are especially tenacious and are difficult to inhibit, even at high concentrations of antibacterial agents. They are both associated with clinical decline in chronic inflammatory airways diseases. For *B. cepacia*, the inhibitory effect lasted over a 48 hour period.

Composition 1 was also able to effectively inhibit MRSA in vitro. This was unexpected due to the high salt concentration of Composition 1 because MRSA generally thrives under high salt concentrations.

Composition 1 was also able to effectively inhibit a mucoid clinical isolate of *Pseudomonas aeruginosa* (Pa UAB-M-4). A mucoid phenotype is associated with multidrug resistance and clinical decline in patients with chronic inflammatory airways diseases.

Composition 1 was also able to effectively inhibit *Burkholderia cepacia, Moraxella catarrhalis, Stenotrophomonas maltophilia*, and *Acinetobacter baumannii* under aerobic conditions with 1% nitrate. Each of these bacteria has been recognized as an emerging pathogen.

Example 2: Stability: Measuring Reduced Glutathione and Reduced Ascorbic Acid Levels Composition 1 (as described in Example 1) was prepared with 150 mg/ml glutathione, 88 mg/ml ascorbic acid and 84 mg/ml sodium bicarbonate based on 322 total mg/ml weight, which corresponds to % total weight of about 46.6%, 27.3% and 26.1%, respectively. The molar ratio of the components in Composition 1 were 0.49 M glutathione, 0.50 M ascorbic acid, and 1 M $HCO_3$.

Composition 2 was prepared with 150 mg/ml glutathione, 126 mg/ml ascorbic acid and 84 mg/ml sodium bicarbonate based on 360 total mg/ml weight, which corresponds to % total weight of about 33%, 38.9% and 28.9%, respectively. The molar ratio of the components in Composition 1 were 0.49 M glutathione, 1 M ascorbic acid, and 1 M $HCO_3$.

The amount of glutathione and ascorbic acid oxidization were determined for Composition 1 at pH 5.5, 6.0, and 6.5. Oxidized glutathione is associated with the generation of protein-carbonyls via glutathionlyation, which occurs when oxidized glutathione dissociates and attaches to proteins. The % oxidized glutathione (% GSSG) was determined after 4 weeks of storage of Composition 1 at pH 5.5, 6.0, and 6.5 under $N_2$-sparged and ambient conditions. Additionally, when ascorbic acid is oxidized into dehydroascorbate (DHA), DHA can break down and result in the formation of protein adducts in process called ascorbylation (Simpson et al., Biochim biophys Acta 2000; 1501:12-24). The % reduced ascorbic acid maintained in Composition 1 (% ASC) was determined after 4 weeks of storage of Composition 1 at pH 5.5, 6.0, and 6.5 under $N_2$-sparged (anaerobic) and ambient conditions. Specifically, nitrogen-sparged samples were mixed under anaerobic conditions sparged with nitrogen, and the samples were packaged using nitrogen bubbling. Ambient samples were mixed under room air conditions and were not bubbled with nitrogen. The formulations were stored at 5° C. for 4 weeks, and the percent of oxidized glutathione (GSSG) and ascorbic acid (ASC) was measured for each sample according to standard techniques.

As shown in Table 17, oxidation of glutathione and ascorbic acid is pH- and oxygen-dependent, and the presence of glutathione increases the concentration of reduced ascorbic acid after 4 weeks of storage at 5° C. Moreover, when oxygen is present in solution, reduced glutathione (GSH) helped maintain ascorbic acid concentration, but the GSH is itself oxidized to GSSG in greater concentrations. These results demonstrate that the pH of Composition 1 is important for maintaining glutathione and ascorbic acid in their reduced state, and that the molar ratios of glutathione and ascorbic acid in Composition 1 further stabilizes the oxidation rates of both glutathione and ascorbic acid.

TABLE 17

| Formulation | pH | Atmosphere | % GSSG | % ASC |
| --- | --- | --- | --- | --- |
| Formulation 1 | 5.5 | N2-sparged | 2.86 | 89.47 |
| Formulation 2 | 6.0 | N2-sparged | 6.54 | 91.20 |
| Formulation 3 | 6.5 | N2-sparged | 9.11 | 91.27 |
| Formulation 4 | 5.5 | Ambient | 6.44 | 90.66 |
| Formulation 5 | 6.0 | Ambient | 15.97 | 90.25 |
| Formulation 6 | 6.5 | Ambient | 19.94 | 91.25 |
| Ascorbic Acid Only | | Ambient | | 77.88 |

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of treating or reducing symptoms in a subject suffering from bronchiectasis, wherein a clinical isolate bacteria chronic colonization infection occurs in the subject's airway, comprising administering to the subject's airway a composition comprising (i) glutathione, a glutathione conjugate, a pharmaceutically-acceptable salt thereof, or any combination thereof, and (ii) ascorbic acid, thereby contacting the clinical isolate, wherein the clinical isolate is *Staphylococcus aureus*, Methicillin-resistant *Staphylococcus aureus* (MRSA), or both, wherein the pH of the composition is about 6 to about 8; and wherein the subject is thereby treated or the symptoms reduced.

2. The method of claim 1, wherein the clinical isolate comprises two or more clinical isolates.

3. The method of claim 1, wherein the clinical isolate is *Staphylococcus aureus* and Methicillin-resistant *Staphylococcus aureus*.

4. The method of claim 1, wherein the clinical isolate is sensitized to an antibiotic to which the clinical isolate was tolerant or resistant prior to contact with the composition.

5. The method of claim 1, wherein the clinical isolate comprises Methicillin-resistant *Staphylococcus aureus* (MRSA).

6. The method of claim 1, wherein the glutathione comprises more than about 80% reduced glutathione by weight of total glutathione in the composition.

7. The method of claim 1, wherein the ascorbic acid comprises more than about 80% reduced ascorbic acid by weight of total ascorbic acid in the composition.

8. The method of claim 1, wherein the composition is administered to the subject twice daily.

9. The method of claim 1, wherein the composition is an aqueous solution.

10. The method of claim 1, wherein the pH of the composition is $7\pm1.5$.

11. The method of claim 10, wherein the composition is an aqueous solution.

* * * * *